United States Patent
Imran et al.

(10) Patent No.: US 12,263,325 B2
(45) Date of Patent: Apr. 1, 2025

(54) DEVICE, SYSTEM AND METHODS FOR THE ORAL DELIVERY OF THERAPEUTIC COMPOUNDS

(71) Applicant: Rani Therapeutics, LLC, San Jose, CA (US)

(72) Inventors: Mir Imran, Los Altos Hills, CA (US); Peter Herrmann, San Jose, CA (US); Baber Syed, Palo Alto, CA (US); Timothy H. Williams, Campbell, CA (US); Chang Jin Ong, Fremont, CA (US); Greg Method, San Jose, CA (US)

(73) Assignee: Rani Therapeutics, LLC, San Jose, CA (US)

( * ) Notice: Subject to any disclaimer, the term of this patent is extended or adjusted under 35 U.S.C. 154(b) by 0 days.

(21) Appl. No.: 18/481,857

(22) Filed: Oct. 5, 2023

(65) Prior Publication Data

US 2024/0082488 A1  Mar. 14, 2024

Related U.S. Application Data

(63) Continuation of application No. 16/828,914, filed on Mar. 24, 2020, now Pat. No. 11,806,504, which is a
(Continued)

(51) Int. Cl.
*A61M 5/155* (2006.01)
*A61K 38/13* (2006.01)
(Continued)

(52) U.S. Cl.
CPC ............ *A61M 5/155* (2013.01); *A61K 38/13* (2013.01); *A61K 38/21* (2013.01); *A61K 38/26* (2013.01);
(Continued)

(58) Field of Classification Search
CPC ............ A61M 3/0237; A61M 5/14526; A61M 5/155; A61M 5/2046; A61M 2005/14204;
(Continued)

(56) References Cited

U.S. PATENT DOCUMENTS 3,788,322 A    1/1974 Michaels
4,055,641 A    10/1977 Benson et al.
(Continued)

FOREIGN PATENT DOCUMENTS

CN    2860501 Y    1/2007
JP    S60-129057 A    7/1985
(Continued)

OTHER PUBLICATIONS

U.S. Appl. No. 18/481,875, filed Oct. 5, 2023, Rani Therapeutics, LLC.
(Continued)

*Primary Examiner* — Kami A Bosworth
(74) *Attorney, Agent, or Firm* — Foley & Lardner LLP

(57) ABSTRACT

Embodiments of the invention provide swallowable devices, preparations and methods for delivering drugs and other therapeutic agents within the GI tract. Particular embodiments provide a swallowable device such as a capsule for delivering drugs into the intestinal wall or other GI lumen. Embodiments also provide various drug preparations that are configured to be contained within the capsule, advanced from the capsule into the intestinal wall and degrade within the wall to release the drug to produce a therapeutic effect. The preparation can be coupled to a delivery mechanism having one or more balloons or other expandable devices which are expandable responsive to a condition in the small intestine or other GI lumen to advance the preparation out of the capsule into the intestinal wall. Embodiments of the invention are particularly useful for the delivery of drugs
(Continued)

which are poorly absorbed, tolerated and/or degraded within the GI tract.

20 Claims, 43 Drawing Sheets

Related U.S. Application Data continuation of application No. 15/674,421, filed on Aug. 10, 2017, now Pat. No. 10,632,251, which is a continuation of application No. 14/244,673, filed on Apr. 3, 2014, now Pat. No. 9,757,514, which is a continuation of application No. 13/837,025, filed on Mar. 15, 2013, now Pat. No. 8,734,429, which is a continuation-in-part of application No. 13/532,589, filed on Jun. 25, 2012, now Pat. No. 9,149,617, which is a continuation-in-part of application No. 12/978,301, filed on Dec. 23, 2010, now Pat. No. 8,562,589, and a continuation-in-part of application No. 12/978,233, filed on Dec. 23, 2010, now Pat. No. 8,721,620.

(60) Provisional application No. 61/571,641, filed on Jun. 29, 2011.

(51) Int. Cl.

| | | |
|---|---|---|
| *A61K 38/21* | (2006.01) | |
| *A61K 38/26* | (2006.01) | |
| *A61K 38/27* | (2006.01) | |
| *A61K 38/28* | (2006.01) | |
| *A61K 38/29* | (2006.01) | |
| *A61K 38/30* | (2006.01) | |
| *A61K 38/55* | (2006.01) | |
| *A61M 5/142* | (2006.01) | |
| *A61M 31/00* | (2006.01) | |
| *A61K 9/48* | (2006.01) | |
| *A61M 37/00* | (2006.01) | |

(52) U.S. Cl.
CPC .............. *A61K 38/27* (2013.01); *A61K 38/28* (2013.01); *A61K 38/29* (2013.01); *A61K 38/30* (2013.01); *A61K 38/55* (2013.01); *A61M 5/14244* (2013.01); *A61M 31/002* (2013.01); *A61K 9/4808* (2013.01); *A61M 37/0069* (2013.01); *A61M 2205/3331* (2013.01); *A61M 2210/1042* (2013.01)

(58) Field of Classification Search
CPC ................ A61M 31/00; A61M 31/002; A61M 2210/1042; A61M 2210/1053; A61M 2210/1057; A61M 2210/106; A61M 2210/1064

See application file for complete search history.

(56) References Cited

U.S. PATENT DOCUMENTS

| | | | |
|---|---|---|---|
| 4,249,531 A | 2/1981 | Heller et al. | |
| 4,425,117 A | 1/1984 | Hugemann et al. | |
| 4,596,819 A | 6/1986 | Nicolaides et al. | |
| 4,612,302 A | 9/1986 | Szabo et al. | |
| 4,663,308 A | 5/1987 | Saffran et al. | |
| 4,781,685 A | 11/1988 | Lehmann et al. | |
| 5,129,915 A | 7/1992 | Cantenys | |
| 5,137,669 A | 8/1992 | Leonard et al. | |
| 5,217,449 A | 6/1993 | Yuda et al. | |
| 5,271,945 A | 12/1993 | Yoshioka et al. | |
| 5,279,607 A | 1/1994 | Schentag et al. | |
| 5,318,557 A | 6/1994 | Gross | |
| 5,474,785 A | 12/1995 | Wright et al. | |
| 5,652,216 A | 7/1997 | Kornfelt et al. | |
| 5,674,205 A | 10/1997 | Pasricha et al. | |
| 5,683,435 A | 11/1997 | Truex et al. | |
| 5,750,926 A | 5/1998 | Schulman et al. | |
| 5,795,591 A | 8/1998 | Lee et al. | |
| 5,849,327 A | 12/1998 | Berliner et al. | |
| 5,904,935 A | 5/1999 | Eckenhoff et al. | |
| 5,987,358 A | 11/1999 | Sosebee et al. | |
| 6,369,073 B1 | 4/2002 | Giannessi et al. | |
| 6,413,238 B1 * | 7/2002 | Maget ............... | A61M 5/14526 604/67 |
| 6,632,216 B2 | 10/2003 | Houzego et al. | |
| 6,645,988 B2 | 11/2003 | Phillips | |
| 6,656,155 B2 | 12/2003 | Freyman | |
| 6,663,864 B1 | 12/2003 | Kink et al. | |
| 6,743,211 B1 | 6/2004 | Prausnitz et al. | |
| 6,975,906 B2 | 12/2005 | Rusin et al. | |
| 7,083,578 B2 | 8/2006 | Lewkowicz et al. | |
| 7,083,579 B2 | 8/2006 | Yokoi et al. | |
| 7,160,258 B2 | 1/2007 | Imran et al. | |
| 7,393,827 B2 | 7/2008 | Nadler | |
| 7,396,265 B2 | 7/2008 | Darley et al. | |
| 7,396,809 B1 | 7/2008 | Lu et al. | |
| 7,502,649 B2 | 3/2009 | Ben-Haim et al. | |
| 7,569,032 B2 | 8/2009 | Naimark et al. | |
| 7,658,736 B2 | 2/2010 | von Alten | |
| 7,785,291 B2 | 8/2010 | Marco et al. | |
| 7,854,745 B2 | 12/2010 | Brister et al. | |
| 8,021,357 B2 | 9/2011 | Tanaka et al. | |
| 8,353,863 B2 | 1/2013 | Imran | |
| 8,517,961 B2 | 8/2013 | Imran et al. | |
| 8,562,589 B2 | 10/2013 | Imran | |
| 8,579,883 B2 | 11/2013 | Tanaka et al. | |
| 8,682,440 B2 | 3/2014 | Imran et al. | |
| 8,721,620 B2 | 5/2014 | Imran | |
| 8,734,429 B2 | 5/2014 | Imran et al. | |
| 8,759,284 B2 | 6/2014 | Imran | |
| 8,764,733 B2 | 7/2014 | Imran | |
| 8,781,591 B2 | 7/2014 | Imran et al. | |
| 8,809,269 B2 | 8/2014 | Imran | |
| 8,809,271 B2 | 8/2014 | Imran | |
| 8,846,040 B2 | 9/2014 | Imran | |
| 8,852,151 B2 | 10/2014 | Imran | |
| 8,948,870 B2 | 2/2015 | Imran | |
| 8,958,879 B2 | 2/2015 | Imran et al. | |
| 8,969,293 B2 | 3/2015 | Imran | |
| 8,980,822 B2 | 3/2015 | Imran | |
| 9,149,617 B2 | 10/2015 | Imran | |
| 9,186,412 B2 | 11/2015 | Kidron et al. | |
| 9,205,127 B2 | 12/2015 | Imran | |
| 9,259,386 B2 | 2/2016 | Imran | |
| 9,283,179 B2 | 3/2016 | Imran | |
| 9,284,367 B2 | 3/2016 | Imran | |
| 9,402,806 B2 | 8/2016 | Imran | |
| 9,402,807 B2 | 8/2016 | Imran | |
| 9,403,002 B2 | 8/2016 | Imran et al. | |
| 9,415,004 B2 | 8/2016 | Imran | |
| 9,456,988 B2 | 10/2016 | Imran | |
| 9,457,065 B2 | 10/2016 | Imran | |
| 9,486,414 B2 | 11/2016 | Imran | |
| 9,492,378 B2 | 11/2016 | Imran | |
| 9,511,121 B2 | 12/2016 | Imran | |
| 9,539,207 B2 | 1/2017 | Imran | |
| 9,629,799 B2 | 4/2017 | Imran | |
| 9,643,005 B2 | 5/2017 | Imran et al. | |
| 9,757,514 B2 | 9/2017 | Imran et al. | |
| 9,757,548 B2 | 9/2017 | Imran | |
| 9,808,510 B2 | 11/2017 | Imran | |
| 9,814,763 B2 | 11/2017 | Imran | |
| 9,844,505 B2 | 12/2017 | Imran | |
| 9,844,655 B2 | 12/2017 | Imran | |
| 9,861,683 B2 | 1/2018 | Imran | |
| 9,907,747 B2 | 3/2018 | Imran | |
| 9,956,178 B2 | 5/2018 | Imran | |
| 9,987,487 B2 | 6/2018 | Imran et al. | |
| 10,004,783 B2 | 6/2018 | Imran | |
| 10,029,080 B2 | 7/2018 | Imran | |
| 10,039,908 B2 | 8/2018 | Imran | |
| 10,058,595 B2 | 8/2018 | Morales et al. | |

(56) References Cited

U.S. PATENT DOCUMENTS

| | | |
|---|---|---|
| 10,098,931 B2 | 10/2018 | Morales et al. |
| 10,179,228 B2 | 1/2019 | Imran |
| 10,220,076 B2 | 3/2019 | Morales et al. |
| 10,227,403 B2 | 3/2019 | Imran et al. |
| 10,252,039 B2 | 4/2019 | Mran |
| 10,300,010 B2 | 5/2019 | Imran |
| 10,307,579 B2 | 6/2019 | Imran |
| 10,314,891 B2 | 6/2019 | Imran |
| 10,314,892 B2 | 6/2019 | Imran |
| 10,322,167 B2 | 6/2019 | Imran |
| 10,335,463 B2 | 7/2019 | Imran |
| 10,350,163 B2 | 7/2019 | Imran |
| 10,478,396 B2 | 11/2019 | Imran |
| 10,487,145 B2 | 11/2019 | Imran |
| 10,493,253 B2 | 12/2019 | Imran |
| 10,548,850 B2 | 2/2020 | Imran |
| 10,596,359 B2 | 3/2020 | Imran |
| 10,603,275 B2 | 3/2020 | Imran et al. |
| 10,603,475 B2 | 3/2020 | Imran |
| 10,632,251 B2 | 4/2020 | Imran et al. |
| 10,639,272 B2 | 5/2020 | Imran |
| 10,689,460 B2 | 6/2020 | Imran et al. |
| 10,752,681 B2 | 8/2020 | Imran |
| 10,864,254 B2 | 12/2020 | Imran |
| 10,874,840 B2 | 12/2020 | Imran |
| 10,888,517 B2 | 1/2021 | Imran |
| 10,926,073 B2 | 2/2021 | Imran |
| 10,953,075 B2 | 3/2021 | Morales et al. |
| 10,953,077 B2 | 3/2021 | Imran |
| 10,967,050 B2 | 4/2021 | Imran |
| 10,980,749 B2 | 4/2021 | Imran |
| 10,987,499 B2 | 4/2021 | Imran |
| 11,026,998 B2 | 6/2021 | Morales et al. |
| 11,103,187 B2 | 8/2021 | Imran |
| 11,229,684 B2 | 1/2022 | Imran |
| 11,253,686 B2 | 2/2022 | Imran |
| 11,291,709 B2 | 4/2022 | Morales et al. |
| 11,304,895 B2 | 4/2022 | Imran |
| 11,304,993 B2 | 4/2022 | Morales et al. |
| 11,338,118 B2 | 5/2022 | Imran |
| 11,376,405 B2 | 7/2022 | Imran |
| 11,419,812 B2 | 8/2022 | Imran |
| 11,555,068 B2 | 1/2023 | Imran |
| 11,638,690 B2 | 5/2023 | Imran |
| 11,654,182 B2 | 5/2023 | Imran |
| 11,684,761 B2 | 6/2023 | Imran |
| 11,771,879 B2 | 10/2023 | Imran |
| 11,806,504 B2 | 11/2023 | Imran et al. |
| 11,813,314 B2 | 11/2023 | Imran |
| 11,814,427 B2 | 11/2023 | Imran |
| 11,844,867 B2 | 12/2023 | Imran |
| 2002/0107504 A1 | 8/2002 | Gordon |
| 2002/0198470 A1 | 12/2002 | Imran et al. |
| 2003/0003516 A1 | 1/2003 | Robinson et al. |
| 2003/0186892 A1 | 10/2003 | Taneja |
| 2003/0226155 A1 | 12/2003 | Sadeghi et al. |
| 2004/0093039 A1 | 5/2004 | Schumert |
| 2004/0106904 A1 | 6/2004 | Gonnelli et al. |
| 2004/0122315 A1 | 6/2004 | Krill |
| 2004/0143221 A1 | 7/2004 | Shadduck |
| 2004/0253304 A1 | 12/2004 | Gross et al. |
| 2004/0267240 A1 | 12/2004 | Gross et al. |
| 2005/0032183 A1 | 2/2005 | Osslund et al. |
| 2005/0038415 A1 | 2/2005 | Rohr et al. |
| 2005/0058701 A1 | 3/2005 | Gross et al. |
| 2005/0065463 A1 | 3/2005 | Tobinaga et al. |
| 2005/0095246 A1 | 5/2005 | Shafer |
| 2005/0124875 A1 | 6/2005 | Kawano et al. |
| 2005/0181059 A1 | 8/2005 | Jacob et al. |
| 2005/0183733 A1 | 8/2005 | Kawano et al. |
| 2005/0267414 A1 | 12/2005 | Abraham-Fuchs et al. |
| 2005/0283045 A1 | 12/2005 | Yamamoto et al. |
| 2006/0063719 A1 | 3/2006 | Jesson et al. |
| 2006/0167339 A1 | 7/2006 | Gilad et al. |
| 2006/0229529 A1 | 10/2006 | Wright |
| 2006/0229592 A1 | 10/2006 | Yokoi et al. |
| 2007/0010709 A1 | 1/2007 | Reinschke |
| 2007/0016262 A1 | 1/2007 | Gross et al. |
| 2007/0066557 A1 | 3/2007 | Monia et al. |
| 2007/0100378 A1 | 5/2007 | Maschino |
| 2007/0123809 A1 | 5/2007 | Weiss et al. |
| 2007/0123973 A1 | 5/2007 | Roth et al. |
| 2007/0155664 A1 | 7/2007 | Ranklove et al. |
| 2007/0156211 A1 | 7/2007 | Ferren et al. |
| 2007/0161851 A1 | 7/2007 | Takizawa et al. |
| 2007/0191811 A1 | 8/2007 | Berglund |
| 2007/0207141 A1 | 9/2007 | Lieberburg |
| 2007/0265598 A1 | 11/2007 | Karasik |
| 2007/0277374 A1 | 12/2007 | Suaning |
| 2007/0288033 A1 | 12/2007 | Murature et al. |
| 2008/0065181 A1 | 3/2008 | Stevenson |
| 2008/0108562 A1 | 5/2008 | Riviere et al. |
| 2008/0160079 A1 | 7/2008 | Takizawa et al. |
| 2008/0188837 A1 | 8/2008 | Belsky et al. |
| 2008/0195171 A1 | 8/2008 | Sharma |
| 2008/0200883 A1 | 8/2008 | Tomono |
| 2008/0214919 A1 | 9/2008 | Harmon et al. |
| 2008/0242928 A1 | 10/2008 | Kawano et al. |
| 2008/0255543 A1 | 10/2008 | Tanaka et al. |
| 2008/0260820 A1 | 10/2008 | Borrelly et al. |
| 2008/0260840 A1 | 10/2008 | Alessi et al. |
| 2008/0275430 A1 | 11/2008 | Belsky et al. |
| 2009/0004266 A1 | 1/2009 | Sung et al. |
| 2009/0030473 A1 | 1/2009 | Khawaled et al. |
| 2009/0030743 A1 | 1/2009 | Tussy |
| 2009/0041849 A1 | 2/2009 | New |
| 2009/0088387 A1 | 4/2009 | Castillo et al. |
| 2009/0187167 A1 | 7/2009 | Sexton et al. |
| 2009/0187229 A1 | 7/2009 | Lavie |
| 2009/0239796 A1 | 9/2009 | Fineman et al. |
| 2009/0258519 A1 | 10/2009 | Dilmaghanian et al. |
| 2009/0275638 A1 | 11/2009 | Fitzgerald et al. |
| 2009/0306473 A1 | 12/2009 | Tanaka et al. |
| 2009/0306633 A1 | 12/2009 | Trovato et al. |
| 2009/0317372 A1 | 12/2009 | Kiss |
| 2010/0021536 A1 | 1/2010 | Gross |
| 2010/0034823 A1 | 2/2010 | Borhani et al. |
| 2010/0049120 A1 | 2/2010 | Dijksman et al. |
| 2010/0056948 A1 | 3/2010 | Hornby et al. |
| 2010/0076027 A1 | 3/2010 | Benson et al. |
| 2010/0094256 A1 | 4/2010 | Kassab et al. |
| 2010/0100117 A1 | 4/2010 | Brister et al. |
| 2010/0105627 A1 | 4/2010 | Salama et al. |
| 2010/0131043 A1 | 5/2010 | Casas et al. |
| 2010/0179381 A1 | 7/2010 | Kawano et al. |
| 2010/0286668 A1 | 11/2010 | Tanaka et al. |
| 2011/0046053 A1 | 2/2011 | Kidron |
| 2011/0097401 A1 | 4/2011 | Phillips et al. |
| 2011/0098651 A1 | 4/2011 | Falo et al. |
| 2011/0183898 A1 | 7/2011 | Dinh |
| 2011/0206766 A1 | 8/2011 | Friedl et al. |
| 2012/0041069 A1 | 2/2012 | Sesha |
| 2013/0280324 A1 | 10/2013 | Jain et al. |
| 2014/0065232 A1 | 3/2014 | Shlieout et al. |
| 2019/0211094 A1 | 7/2019 | Imran et al. |
| 2020/0093740 A1 | 3/2020 | Imran |
| 2020/0095312 A1 | 3/2020 | Imran |
| 2020/0139095 A1 | 5/2020 | Imran |
| 2020/0171287 A1 | 6/2020 | Imran |
| 2020/0206132 A1 | 7/2020 | Imran et al. |
| 2020/0222318 A1 | 7/2020 | Imran et al. |
| 2020/0247906 A1 | 8/2020 | Imran et al. |
| 2020/0276425 A1 | 9/2020 | Imran |
| 2020/0276426 A1 | 9/2020 | Imran |
| 2020/0289620 A1 | 9/2020 | Hashim et al. |
| 2020/0308268 A1 | 10/2020 | Imran |
| 2021/0038873 A1 | 2/2021 | Imran |
| 2021/0069298 A1 | 3/2021 | Imran |
| 2021/0085600 A1 | 3/2021 | Imran |
| 2021/0138216 A1 | 5/2021 | Imran |
| 2021/0162016 A1 | 6/2021 | Imran |
| 2021/0196639 A1 | 7/2021 | Imran |
| 2022/0008013 A1 | 1/2022 | Imran |
| 2022/0118056 A1 | 4/2022 | Imran et al. |

(56) References Cited

U.S. PATENT DOCUMENTS

| | | |
|---|---|---|
| 2022/0175890 A1 | 6/2022 | Imran |
| 2022/0202707 A1 | 6/2022 | Imran |
| 2022/0202910 A1 | 6/2022 | Morales et al. |
| 2022/0296510 A1 | 9/2022 | Imran |
| 2022/0323733 A1 | 10/2022 | Imran |
| 2022/0339095 A1 | 10/2022 | Imran |
| 2023/0203148 A1 | 6/2023 | Imran |
| 2023/0310313 A1 | 10/2023 | Imran |
| 2023/0355717 A1 | 11/2023 | Imran |
| 2024/0001094 A1 | 1/2024 | Imran |
| 2024/0017048 A1 | 1/2024 | Imran |

FOREIGN PATENT DOCUMENTS

| | | |
|---|---|---|
| JP | 2002-186672 A | 7/2002 |
| JP | 2004-504120 A | 2/2004 |
| JP | 2005-021677 A | 1/2005 |
| JP | 2005-185644 A | 7/2005 |
| JP | 2007-007414 A | 1/2007 |
| JP | 2010-273936 A | 12/2010 |
| WO | WO-94/22423 A1 | 10/1994 |
| WO | WO-00/47219 A2 | 8/2000 |
| WO | WO-00/62759 A1 | 10/2000 |
| WO | WO-02/07813 A1 | 1/2002 |
| WO | WO-03/028653 A2 | 4/2003 |
| WO | WO-03/068061 A1 | 8/2003 |
| WO | WO-2004/000389 A2 | 12/2003 |
| WO | WO-2004/024224 A1 | 3/2004 |
| WO | WO-2004/058041 A2 | 7/2004 |
| WO | WO-2004/066903 A2 | 8/2004 |
| WO | WO-2005/051451 A2 | 6/2005 |
| WO | WO-2005/099776 A2 | 10/2005 |
| WO | WO-2005/105053 A2 | 11/2005 |
| WO | WO-2006/064502 A2 | 6/2006 |
| WO | WO-2006/077528 A2 | 7/2006 |
| WO | WO-2007/013059 A2 | 2/2007 |
| WO | WO-2007/069696 A1 | 6/2007 |
| WO | WO-2007/093806 A1 | 8/2007 |
| WO | WO-2007/136735 A2 | 11/2007 |
| WO | WO-2008/065144 A2 | 6/2008 |
| WO | WO-2009/041525 A1 | 4/2009 |
| WO | WO-2010/045482 A2 | 4/2010 |
| WO | WO-2010/093834 A2 | 8/2010 |
| WO | WO-2010/098384 A2 | 9/2010 |
| WO | WO-2011/079302 A2 | 6/2011 |
| WO | WO-2011/112229 A2 | 9/2011 |
| WO | WO-2013/003487 A1 | 1/2013 |
| WO | WO-2013/003824 A1 | 1/2013 |
| WO | WO-2014/159604 A1 | 10/2014 |
| WO | WO-2016/183040 A1 | 11/2016 |
| WO | WO-2017/004623 A1 | 1/2017 |

OTHER PUBLICATIONS

U.S. Appl. No. 18/481,893, filed Oct. 5, 2023, Rani Therapeutics, LLC.
Bauer, K.H. et al., "Pharmazeutische Technologie", (Gustav Fischer, Verlag, Germany) (Jan. 1997) (5th ed.), pp. 337-349.
Betancourt, T. et al., "Micro- and nanofabrication methods in nanotechnological medical and pharmaceutical devices", International Journal of Nanomedicine, 1(4), Dec. 2006, pp. 483-495.
Borchard, G. et al., "A Novel Peroral Peptide Drug Delivery System Based on Superporous Hydrogel Polymers", Carrier-Based Drug Delivery, Ch. 21, pp. 296-316, ACS Symposium Series, vol. 879, May 2004.
Cho, J. and Feldman, M., "Heterogeneity of autoimmune diseases: pathophysiologic insights from genetics and implications for new therapies", Nature Medicine, 21, 2015, pp. 730-738.
Fallingborg, J., "Intraluminal pH of the human gastrointestinal tract", Danish Medical Bulletin, 46 (3), Jun. 1999.
Ferrua, M. et al., "Understanding the fluid dynamics of gastric digestion using computational modeling," Procedia Food Science, 11th International Congress on Engineering and Food ICEF11.
Frandsen, G. et al., "Abrams' Clinical Drug Therapy", 2013, Lippincott Williams & Wilkins, 3 pages.
Gordon, F.H., et al., "A pilot study of treatment of active ulcerative colitis with natalizumab, a humanized monoclonal antibody to alpha-4 integrin", Alimentary Pharmacology and Therapeutics, vol. 16, Issue 4, Apr. 2002, pp. 699-705.
Gregersen, P. and Behrens, T., "Genetics of autoimmune diseases—disorders of immune homeostasis", Nature Reviews Genetics, 7, 2006, pp. 917-928.
Hosny, E. et al., "Oral delivery of insulin from enteric-coated capsules containing sodium salicylate: effect on relative hypoglycemia of diabetic beagle dogs", International Journal of Pharmaceutics, 237(1-2), Apr. 2002, pp. 71-76.
Irons, et al., "Bioadhesives in Drug Delivery", Taylor and Francis Group, LLC, 2003, Ch. 48.
Jain, R., "The manufacturing techniques of various drug loaded biodegradable poly(lactide-co-glycolide) (PLGA) devices", Biomaterials, vol. 21, Issue 23, Dec. 2000, pp. 2475-2490.
Jambhekar, S. et al., "Basic Pharmacokinetics", Pharmaceutical Press, Royal Pharmaceutical Society, 2nd ed., published Mar. 2012, Chapter 6, 22 pages, retrieved online Oct. 25, 2013 from http://www.pharmpress.com/files/docs/Basic%20Pharmacokinetics%20sample.pdf.
Jin, C. et al., "A new orally available glucagon-like peptide-1 receptor agonist, biotinylated exendin-4, displays improved hypoglycemic effects in db/db mice", Journal of Controlled Release, 133(3), Feb. 2009, pp. 172-177.
Pfeffer, L.M. et al., "Biological Properties of Recombinant Alpha-Interferons: 40th Anniversary of the Discovery of the Interferons", Cancer Research, vol. 58, Issue 12, Jun. 1998, pp. 2489-2499.
Roberts, F. et al., "Pharmacokinetics and anaesthesia", Continuing Education in Anaesthesia Critical Care & Pain, vol. 7, Issue 1, Feb. 2007, pp. 25-29.
Tao, S. et al., "Gastrointestinal patch systems for oral drug delivery", Drug Discovery Today, 10(13), Jul. 2005, pp. 909-915.
Whitehead, K. et al., "Oral delivery of macromolecules using intestinal patches: applications for insulin delivery", Journal of Controlled Release, 98(1), Jul. 2004, pp. 37-45.
Wikipedia article entitled "Small intestine" printed Apr. 16, 2020.
Yoncheva, K. et al., "Pegylated nanoparticles based on poly(methyl vinyl ether-co-maleic anhydride): preparation and evaluation of their bioadhesive properties", European Journal of Pharmaceutical Sciences, vol. 24, Issue 5, Apr. 2005, pp. 411-419.

* cited by examiner

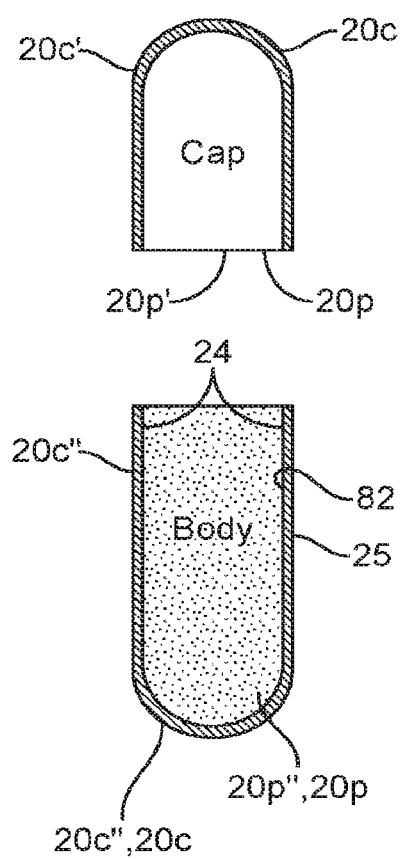
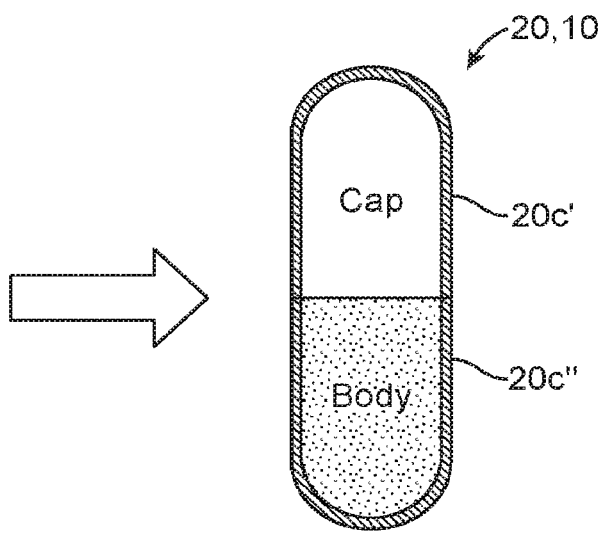
FIG. 2A
FIG. 2B

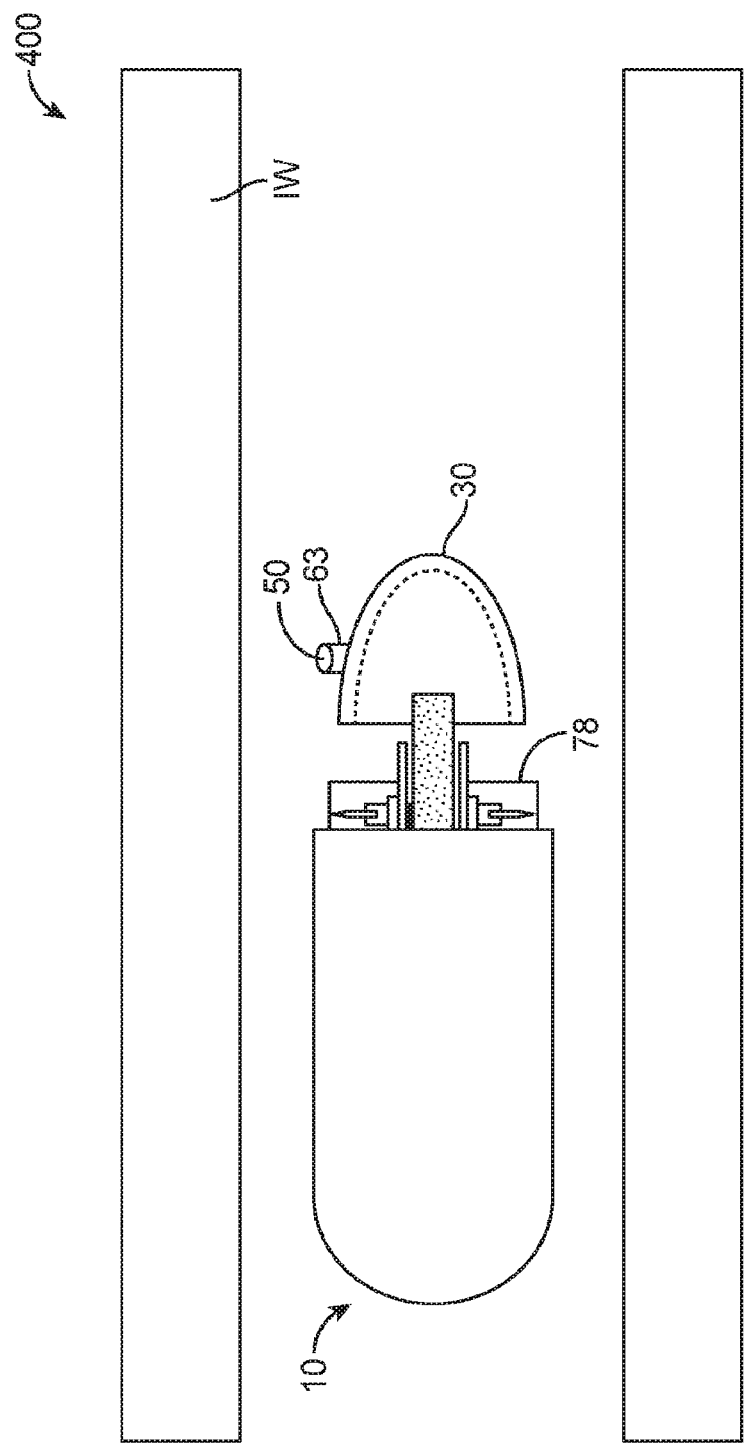

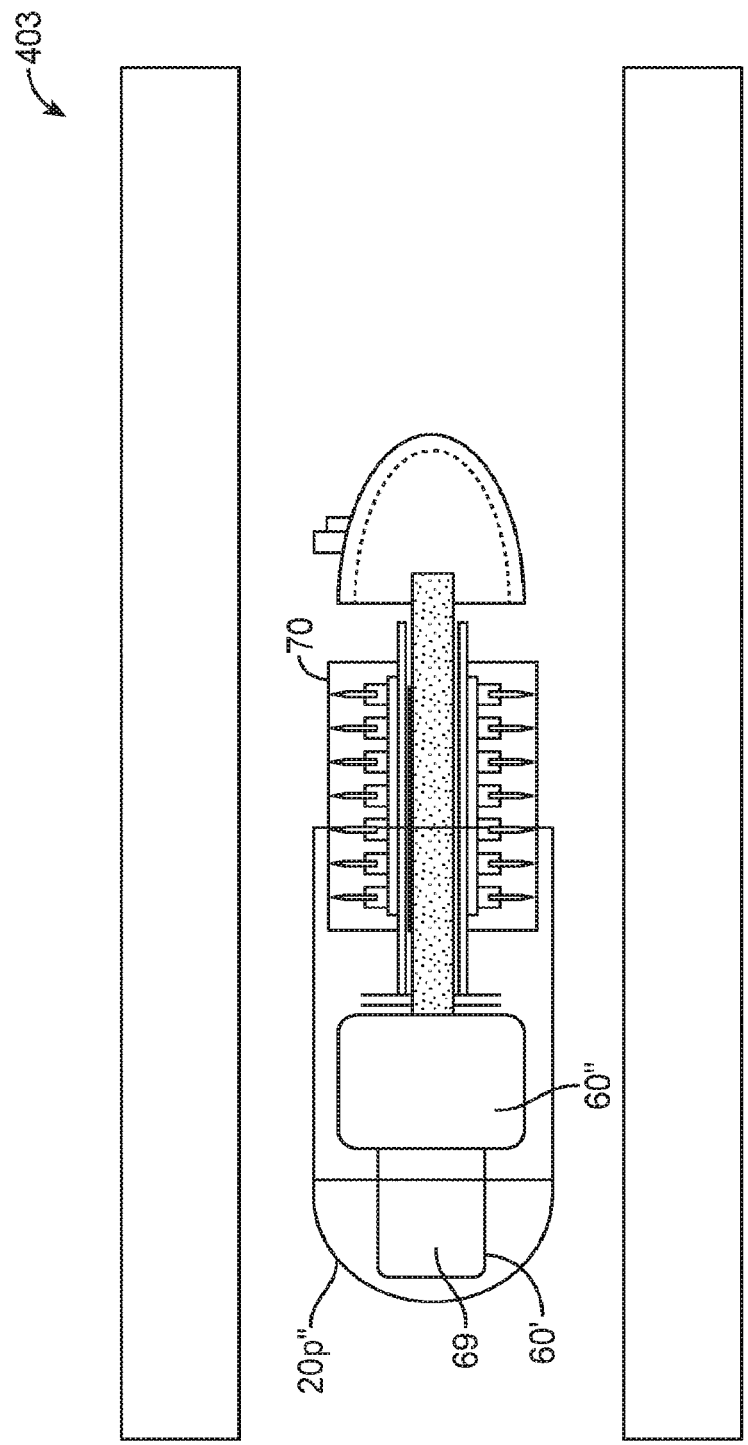

↓ Deglutition

DEVICE, SYSTEM AND METHODS FOR THE ORAL DELIVERY OF THERAPEUTIC COMPOUNDS

CROSS-REFERENCE TO RELATED APPLICATION

This application is a continuation of U.S. patent Ser. No. 16/828,914, filed Mar. 24, 2020, now U.S. Pat. No. 11,806,504; which is a continuation of U.S. patent Ser. No. 15/674,421, filed Aug. 10, 2017, now U.S. Pat. No. 10,632,251; which is a continuation of U.S. patent application Ser. No. 14/244,673, filed Apr. 3, 2014, now U.S. Pat. No. 9,757,514; which is a continuation of U.S. patent application Ser. No. 13/837,025, filed Mar. 15, 2013, now U.S. Pat. No. 8,734,429; which is a continuation-in-part of U.S. patent application Ser. No. 13/532,589, filed on Jun. 25, 2012, now U.S. Pat. No. 9,149,617; which claims the benefit of U.S. Provisional Patent Application Ser. No. 61/571,641, filed Jun. 29, 2011, and is also a continuation-in-part of U.S. patent application Ser. Nos. 12/978,233 and 12/978,301, both filed on Dec. 23, 2010; the contents of which are hereby incorporated by herein by reference in their entirety.

BACKGROUND OF THE INVENTION

Embodiments of the invention relate to swallowable drug delivery devices. More specifically, embodiments of the invention relate to swallowable delivery devices for delivering therapeutic agents to the small intestine.

While there has been an increasing development of new drugs in recent years for the treatment of a variety of diseases, many including proteins, antibodies and peptides have limited application because they cannot be given orally. This is due to a number of reasons including: poor oral toleration with complications including gastric irritation and bleeding; breakdown/degradation of the drug compounds in the stomach; and poor, slow or erratic absorption of the drug. Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery. Thus, there is a need for an improved method for delivery of drugs and other therapeutic agents.

BRIEF SUMMARY OF THE INVENTION

Embodiments provide devices, systems, kits and methods for delivering drugs and other therapeutic agents to various locations in the body. Many embodiments provide a swallowable device for delivering drugs and other therapeutic agents within the GI tract. Particular embodiments provide a swallowable device such as a capsule for delivering drugs and other therapeutic agents into the wall of the small intestine, large intestine or other GI organ wall. Embodiments of the invention are particularly useful for the delivery of drugs and other therapeutic agents which are poorly absorbed, poorly tolerated and/or degraded within the GI tract. Further, embodiments of the invention can be used to deliver drugs and other therapeutics such as proteins, polypeptides and antibodies which were previously only capable of or preferably delivered by intravenous or other form of parenteral administration (e.g., intramuscular, etc.). Additionally, embodiments of the invention are useful for achieving rapid release of a drug into the blood stream via oral delivery.

In one aspect, a swallowable device is provided for delivering drugs or other therapeutic agents into the wall of the small or large intestine or other organ of the gastrointestinal tract. The device comprises a capsule sized to be swallowed and pass through the gastro-intestinal tract, a deployable aligner positioned within the capsule for aligning a longitudinal axis of the capsule with the longitudinal axis of the small intestine, a delivery mechanism for delivering the therapeutic agent into the intestinal wall and a deployment member for deploying at least one of the aligner or the delivery mechanism. The capsule wall is degradable by contact with liquids in the GI tract but also may include an outer coating or layer which only degrades in the higher pH's found in the small intestine, and serves to protect the underlying capsule wall from degradation within the stomach before the capsule reaches the small intestine at which point the drug delivery is initiated by degradation of the coating. In use, such materials allow for the targeted delivery of a therapeutic agent in a selected portion of the intestinal tract such as the small intestine. Suitable outer coatings can include various enteric coatings such as various co-polymers of Methacrylic Acid and Ethyl Acrylate.

In many embodiments, the capsule is formed from two portions such as a body and a cap, where the cap which fits onto the body, e.g., by sliding over or under the body. One portion such as the cap can be configured to degrade above a first pH (e.g., pH 5.5) and the second portion can be configured to degrade above a second higher pH (e.g. 6.5). This allows for triggers and/or mechanisms in one portion of the capsule to be actuated before those in the other portion of the capsule because intestinal fluids will first enter those portions where the lower pH coating has degraded thus actuating triggers which are responsive to such fluids (e.g., degradable valves). In use, such embodiments provide several benefits to the drug delivery process, including an enhanced degree of locational specificity for drug delivery and improved reliability for such delivery. This is due to the fact that deployment of a particular sub-mechanism, such as the aligner, can begin in the upper area of the small intestine SI allowing the capsule to be aligned within the intestine for optimal delivery as well as allowing sufficient time for deployment/actuation of other mechanisms to achieve drug delivery into the intestinal wall while the capsule is still in the small intestine or other selected location.

In addition to having degradable cap and body section, selectable portions of the capsule can be configured to allow the entire device to controllably degrade into smaller pieces. Such embodiments facilitate passage and excretion of the devices through GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The seams can also be so treated to allow the capsule to be broken apart into smaller pieces by the forces applied from expansion of the balloon or other expandable member. In other embodiments for producing capsule degradation after deployment of the tissue penetrating members, the capsule can be comprise two halves or other fractional sections which are mechanically fit together, e.g., by a snap fit and thus readily separated by the forces applied from balloon inflation.

The aligner will typically comprise an expandable balloon known as an aligning balloon which can be fabricated from various polymers known in the medical device arts. The aligning balloon serves to extend the length of the capsule when the aligning balloon is inflated such that the capsule aligns in a parallel fashion with the longitudinal axis of the small intestine. Further, the aligning balloon can have an inflated shape and length such that when inflated, forces exerted by the peristaltic contractions of the intestine on the extended capsule serve to align the capsule in a parallel fashion with the longitudinal axis of the small intestine. Suitable shapes can include an elongated hotdog-like shape. Suitable lengths can include a range between about ½ to two times the length of the capsule. For embodiments where the deployment engine includes use of a deploying balloon and chemical reactants, the aligning balloon is fluidically coupled to the deployment balloon such that expansion of the deploying balloon serves to expand the aligning balloon. In some embodiments, the aligning balloon can contain the chemical reactants which react upon mixture with water or other liquid from the deploying balloon. In addition to performing an alignment function, inflation of the aligning balloon can also serve to push out various components of the device contained within capsule such as the delivery. In use, such configurations improve the reliability for delivery of the therapeutic agent since it is not necessary to wait for particular portions of the capsule overlying the delivery mechanism to be degraded before drug delivery can occur.

In many embodiments, the deployment member will comprise an expandable balloon, known as the deployment balloon, that is fluidically coupled to the aligner balloon by means of a connector tube and a pH degradable valve which is responsive to the higher pH's found in the intestinal fluids. In this application when the term "fluidically coupled" is applied to two or more elements it means that those two or more elements are connected in such a way that fluid transport is possible between the elements is possible, for example, by active pumping or passive flow. In the deployed state, the deployment balloon can have a dome shape which corresponds to the shape of an end of the capsule. In many embodiments, the deployment balloon in combination with the aligner balloon can comprise a deployment engine, where the deployment balloon contains liquid water and the aligner balloon contains at least one chemical reactant that reacts to produce a gas in the presence of water, which in turn expands the aligner balloon. The reactants will typically include at least two reactants for example, an acid such as citric acid and a base such as sodium hydroxide or potassium hydroxide, which can have about a 1:2 ratio, though other ratios are also contemplated. Other reactants including other acids, e.g., ascetic acid and bases are also contemplated. When the valve or other separation means opens, the reactants mix in the liquid and produce a gas such as carbon dioxide which expands the aligner balloon or other expandable member.

In one alternative embodiment, the deployment balloon can actually comprise two balloons connected by a connecting tube or other connection means having a degradable valve that is pH responsive. The two balloons can each have a half dome shape allowing them to fit into the end portion of the capsule when in the expanded state. One balloon can contain the chemical reactant(s) (e.g., sodium bicarbonate, citric acid, etc.) and the other the liquid water, so that when the valve is degraded the two components mix to form a gas (e.g., carbon dioxide) which inflates both balloons/compartments and in turn, the aligning balloon. In these embodiments the deployment engine comprises the two deployment balloons. In yet another alternative embodiment, the deployment balloon can include at least a first and a second portion or compartment which are separated by a separation valve or other separation means. Water, can be disposed within the first compartment and the chemical reactants in the other. When the valve or other separation means opens, the reactants mix in the liquid and produce a gas which is used to expand the aligning balloon and the deployment balloon. In various embodiments using chemical reactants, the chemical reactants alone in combination with the deployment balloon can comprise a deployment engine for deploying one or both of the aligning balloon (or other aligner) or the delivery mechanism. Other forms of a deployment engine are also contemplated such as use of expandable piezo-electric materials (that expand by application of a voltage), springs and other shape memory materials and various thermally expandable materials.

Various embodiments of the valve which separates the aligning balloon from the deployment balloon can be configured to open in a number of ways and responsive to a number of conditions. Typically, the valve will be configured to open by having one or more portions degrade in response to the higher pH found in intestinal fluids and may be fabricated from various enteric materials known in the art such as various co-polymers of methacylic acid and co-ethyl acrylate described herein. In other embodiments, including those where the deployment balloon contains the chemical reactants, the valve can be configured to open in response to a selected pressure so as to allow the gas from the deployment balloon to inflate the aligning balloon. Similarly, the same or related embodiments of such a pressure sensitive valve can be used to provide for inflation of the delivery balloon upon the development of sufficient pressure in the aligning balloon so that a serial inflation effect is achieved. In an alternative or additional embodiment, the valve may also be configured to open in response to compressive forces applied by a peristaltic contraction within the small intestine. In still another approach, the valve may be a time release valve configured to open after a certain period of time after an activation step initiated by the patient such as the pealing of a tab or pressing of a button.

Embodiments of the delivery mechanism will typically comprise an expandable member such as an expandable balloon (known as the delivery balloon) that is fluidically coupled to the aligning balloon and a delivery assembly that is coupled to a wall of the delivery balloon. At least one tissue penetrating member (TPM) is coupled to the delivery device. In various embodiments, the delivery balloon can have an elongated shape with two relatively flat faces connected by an articulated accordion-like body. The flat faces can be configured to press against the intestinal wall upon expansion of the balloon so as to insert the TPM into the intestinal wall. TPM's can be positioned on one or both faces to allow insertion of drug containing TPMs on opposite sides of the intestinal wall. The faces may have sufficient surface area to allow for placement of a number of drug containing tissue penetrating members on each face.

The TPM contains the drug or other therapeutic agent and is configured to be inserted into the intestinal wall by expansion of the delivery balloon or other expandable delivery means. The TPM typically comprises a shaft including a proximal portion detachably coupled to the delivery device, a tissue penetrating distal portion and a retaining feature for retaining the tissue penetrating member within the intestinal wall. However, in some embodiments the TPM need not include the retaining feature, but instead can have shape or otherwise be configured to be retained in the intestinal wall without the retaining feature. The TPM is described in further detail below.

In many embodiments, the delivery mechanism device comprises a delivery structure coupled to delivery balloon or other expandable deploying member. In one embodiment, the delivery structure has an open box structure including side walls and a bottom wall which collectively defines a cavity. The delivery balloon or other delivery member may include multiple carrying structures so as to place TPMs in multiple locations of the intestinal wall. In embodiments of the delivery balloon having an accordion-like shape on or more carrying structures can be placed on each of face of the delivery balloon. The carrying structure can have a unitary construction and may be fabricated using vacuum forming. The bottom wall is attached to the expandable member for example by an adhesive. An advancement structure is positioned in the cavity and includes one or more tissue penetrating members detachably coupled to the advancement structure. A protective penetrable film is coupled to the side walls and covering the cavity. The protective film seals the tissue penetrating members inside the advancement structure and serves as a protective barrier for the TPM to protect them from exposure to humidity and oxidation. In use, this film provides an additional level of protection for preventing the therapeutic agent from being degraded within the intestinal tract before it is delivered into the intestinal wall. The film also serves to extend the shelf life of the therapeutic agent preparation by protecting the preparation from exposure to moisture and oxidation.

The TPM is formed at least in part from a therapeutic agent preparation including a drug or other therapeutic agent that is configured to dissolve or otherwise be absorbed within the intestinal wall so as to deliver the therapeutic agent preparation to the patient's blood stream. The therapeutic agent preparation may also include one or more pharmaceutical excipients known in the art, e.g., disintegrants, binders, etc. The TPM is desirably configured to penetrate a selected distance into the intestinal wall so as to deliver therapeutic agent to a particular tissue layer of the intestinal wall, for example the mucosal layer, submucosal layer, etc. This can be achieved through the use of stops positioned on the TPM shaft and/or configuring the TPM shaft to bend or even shear once it penetrates a selected distance in the intestinal wall.

Typically, the drug or other therapeutic agent delivered by the TPM will be mixed in with a biodegradable polymer such as PLGA (polylactic-co-glycolic acid) and/or a sugar such as maltose. In such embodiments, the TPM may comprise a substantially heterogeneous mixture of drug and biodegradable polymer. Alternatively, the penetrating member may include a portion formed substantially from a biodegradable polymer and a separate section or compartment that is formed from or contains the drug or other therapeutic agent. For example, in one embodiment the TPM may comprise an outer shell of biodegradable material with a hollow core which is fitted with a slug (e.g., cylinder shape) of the therapeutic agent. The tip or tissue penetrating portion of the TPM can include a harder material such as a sugar so as to be able to readily penetrate tissue. Once placed in intestinal wall, the tissue penetrating member is degraded by the interstitial fluids within the wall tissue, the drug dissolves in those fluids and is absorbed into the blood stream by the capillaries in or around the intestinal wall tissue. The TPM will also typically include one or more tissue retaining features such as a barb or hook to retain the penetrating member within the tissue of the intestinal wall after advancement. The retaining features can be arranged in various patterns to enhance tissue retention such as two or more barbs symmetrically distributed around the member shaft. However, the TPM can also be retained in the intestinal through other means such as by a reverse taper or other shape. The reverse taper shape may also be combined with one or more retaining features to further enhance retention.

The drug or other therapeutic agent can be in solid form and then formed into the shape of the tissue penetrating member using molding or other like method or may be in solid or liquid form and then added to the biodegradable polymer in liquid form with the mixture then formed into the TPM using molding or other forming method known in the polymer arts. Desirably, embodiments of the tissue penetrating member comprising a drug and degradable polymer are formed (e.g., cured) at temperatures which do not produce any substantial thermal degradation of the drug including drugs such as various peptides and proteins. This can be achieved through the use of room temperature curing polymers and room temperature molding and solvent evaporation techniques known in the art. In particular embodiments, the amount of thermally degraded drug within the tissue penetrating member is desirably less than about 10% by weight, more preferably less than 5% and still more preferably, less than 1%. The thermal degradation temperatures for a particular drug are known or can be determined using methods known in the art and then this temperature can be used to select and adjust the particular polymer processing methods (e.g., molding, curing, solvent evaporation etc.).

For various embodiments of the invention wherein one or more of the aligner, deployment member, delivery member comprises an expandable balloon, the balloon can have material properties and dimensions (e.g., wall thickness) allowing the balloon to be wrapped (or otherwise disposed in the capsule) so as to occupy reduced/minimal space. Accordingly, various embodiments of expandable balloons used by the invention can be thin walled e.g., less than about 0.001 inches and can comprise various non-compliant polymers known in the art such as PET (polyethylene terephthalate), polyethylene and polyimide.

One or more embodiments of the expandable balloons will also typically include a deflation valve which serves to deflate the balloon after inflation. The deflation valve can comprise biodegradable materials which are configured to degrade upon exposure to the fluids in the small intestine and/or liquid in one of the compartments of the balloon so as to create an opening or channel for escape of gas within balloon. In particular embodiments, the deflation valve comprises a tube valve attached to the end of the delivery balloon (opposite to the end which is coupled to the aligner balloon). The tube valve comprises a hollow tube having an end portion filled with a material such as maltose that degrades upon exposure to fluid such as the fluid in the small intestine. The positioning of the obstructing material in the tube valve is configured to provide sufficient time for the delivery balloon to inflate and deliver the tissue penetrating members into the intestinal wall before the obstructing material dissolves to open the tube valve. According to one or more embodiments, once the deflation valve opens, it not only serves to deflate the delivery balloon but also the aligner balloon and deployment balloon since in many embodiments, all three are fluidically connected. Opening of the deflation valve can be facilitated by placing it on the end of the delivery balloon that is forced out of the capsule by inflation of the aligner balloon so that it has good exposure to liquids in the small intestine. Similar tube deflation valves can also be positioned on one or both of aligner balloon and the deployment balloon. In these later two cases, the obstructing material in the tube valve can be configured to degrade over a time period to allow sufficient time for inflation of the delivery balloon.

Additionally, as further backup for insuring balloon deflation, one or more puncture elements can be attached to the inside surface of the capsule wall such that when one or more balloons used in embodiments of the invention fully inflate they contact and be punctured by the puncture element. In another alternative or additional embodiment of a means for deflation of the delivery balloon, one or more of the tissue penetrating members can be directly coupled to the delivery balloon and are configured to tear away from the balloon when they detach, tearing the balloon wall in the process. In yet another alternative one or more tissue penetrating members on the delivery assembly and/or otherwise attached to the delivery balloon can be configured to puncture one or both of the delivery balloon and the aligner balloon upon inflation of the delivery balloon.

Another aspect of the inventions provides therapeutic agent preparations for delivery into the wall of the small intestine (or other wall of a lumen in the intestinal tract) using embodiments of the swallowable device described herein. The preparation comprises a therapeutically effective dose of at least one therapeutic agent (e.g., insulin, incretin, an anti-seizure compound, NSAIDs, an antibiotic, etc.). The preparation may comprise a solid, liquid, gel and combinations thereof and can include one or more pharmaceutical excipients. The preparation has a shape and material consistency to be contained in the swallowable capsule, delivered from the capsule into the lumen wall and degrade within the lumen wall to release the dose of therapeutic agent. Typically, this shape and material consistency are achieved by placing or forming the preparation into one or more embodiments of the tissue penetrating members described herein. The preparation may also have a selectable surface area to volume ratio so as enhance or otherwise control the rate of degradation of the preparation in the wall of the small intestine or other body lumen. The dose of the drug or other therapeutic agent in the preparation can be titrated downward from that which would be required for conventional oral delivery methods so that potential side effects from the drug can be reduced.

One embodiment of the invention is directed to a swallowable device for delivering a therapeutic agent into an intestinal wall of a patient's intestinal tract. The swallowable device comprises a swallowable capsule sized to pass through the intestinal tract, the capsule having a capsule wall, at least a portion of which degrades upon exposure to a selected pH in an intestine while protecting the capsule wall from degradation in a stomach of the patient. The swallowable device also comprises at least one expandable member assembly disposed within the capsule comprising a first compartment and a second compartment separated by a degradable valve. The degradable valve typically comprises an O-ring positioned over a dissolvable pinch valve. The dis solvable pinch valve typically comprises a disk or a volume of a degradable valve material. The degradable valve material is typically configured to dissolve at a selected pH in the intestine. The force of the O-ring coupled with the presence of the degradable valve material pinches the expandable member assembly to separate the first and the second compartments. Dissolving or degrading the degradable valve material in the intestine stops the valve from pinching the expandable member assembly. The first compartment may be initially in at least a partially non expanded state. The second compartment may be initially in at least a partially non expanded state. The expandable member assembly may be a balloon. Compartments of the expandable member assembly may be portions of the balloon. For the purposes of this application the terms "balloon" and "expandable member" may be used interchangeably. Typically a liquid will be disposed in one of the compartments for the expandable member assembly while a reactant is disposed in the other compartment of the expandable member assembly. When the valve degrades the liquid and the reactant are allowed to mix. The liquid itself may be a reactant. As described in other embodiments the liquid and reactant may comprise and acid and base citric acid and as potassium bicarbonate. Upon mixing of the liquid and the reactant a chemical reaction takes place that produces a gas. The gas may be $CO_2$ or another inert or otherwise biocompatible gas. The gas inflates at least the second compartment of the expandable member assembly. The gas may also inflate the other compartment(s) of the expandable member assembly. The swallowable device further comprises a delivery mechanism. The delivery mechanism is typically coupled to the wall of the second compartment. The swallowable device also comprises at least one tissue penetrating member. The tissue penetrating member comprises at least a proximal portion detachably coupled to the delivery mechanism, a tissue penetrating distal portion, and a therapeutic preparation for delivery into the intestinal wall of the patient. The tissue penetrating member may be configured to be retained in the intestinal wall. The tissue penetrating member is typically also configured to degrade in intestinal wall, thereby releasing a therapeutic agent composition. Upon expansion of the second compartment the at least one tissue penetrating member is advanced into the intestinal wall by the delivery mechanism where it is retained in the intestinal wall so as to deliver the therapeutic agent into the intestine. The delivery mechanism may comprise at least one piston-cylinder assembly. The at least one piston-cylinder assembly is typically disposed inside the second compartment of the expandable member assembly.

A piston-cylinder assembly typically comprises a piston slidably disposed in a cylinder. The cylinder may be coupled to the wall of a compartment of the expandable member assembly. Typically the cylinder is coupled to the wall of the second compartment of the expandable member assembly. An adhesive joint can be used to couple the cylinder to the wall of the expandable member assembly. The interface between the piston and cylinder is typically sealed with a piston O-ring. The piston typically has a proximal face exposed to an interior of the second compartment. Typically the cylinder has a distal portion coupled to the wall of the second compartment such that a lumen of the cylinder is in communication with an exterior of the second compartment and such that the lumen of the cylinder is sealed off from the interior of the second compartment by the piston O-ring. The lumen of the cylinder may be in communication with the exterior of the second compartment via a needle lumen typically sized with a diameter less than that of the cylinder. The needle lumen provides access to the exterior of the second compartment. The piston is adapted to slide inside the cylinder towards the wall of the second compartment. The piston is configured to advance the tissue penetrating member into the intestinal wall as it slides inside the cylinder. In some embodiments the tissue penetrating member is disposed inside the needle lumen and coupled to the piston via a piston rod sized to slide inside the needle lumen. Sliding motion of the piston advances the tissue penetrating member out of the needle lumen into the exterior of the expandable member assembly and into the intestinal wall.

Typically, the gas produced by the mixture of the liquid and the reactant drives the piston through the cylinder.

The piston-cylinder assembly may further comprise a pressure sensitive release or latch. The pressure sensitive release (or latch) is configured to prevent the piston from sliding inside the cylinder until a specified pressure is reached inside the second compartment (e.g., by generation of the gas or other pressure generating means).

The swallowable device may further comprise a means of alignment configured to align a long axis of the balloon with a long axis of the intestine. Such a means of alignment may comprise a deployable aligner such as those described elsewhere in this application. The means of alignment may also be a shape of the swallowable device. The shape may be that of an elongate pill or a hot dog shape, the shape having an aspect ratio and size scale sufficient to naturally align the swallowable device long axis with the long axis of the intestine as the swallowable device proceeds through the patient's intestinal tract.

The swallowable device may further comprise a means of piston-cylinder assembly alignment, configured to align the piston-cylinder assembly such that the long axis of the cylinder is oriented perpendicular to the surface of the intestinal wall so that the tissue penetrating member is advanced perpendicularly into the intestinal wall. In some embodiments, a long axis of the piston-cylinder assembly defined by the long axis of the cylinder is initially aligned with the long axis of the swallowable device. Upon inflation of the second compartment of the expandable member assembly the piston-cylinder assembly is realigned such that the long axis of the piston cylinder assembly is perpendicular to the long axis of the swallowable device. In this alignment the long axis of the piston-cylinder assembly is also perpendicular to the intestinal wall. Such means for piston-cylinder assembly alignment may comprise aligner balloons described elsewhere in this application. In some embodiments such means for piston-cylinder assembly alignment comprise a pre-stressed portion of the wall of the second compartment of the expandable member assembly to which the piston-cylinder assembly is coupled to via an adhesive joint. When the adhesive joint is made the second compartment may be inflated and the alignment of the piston-cylinder assembly long axis may be perpendicular to the wall of the second compartment. After the joint is made the piston cylinder assembly is forced into alignment with the long axis of the swallow able device and the second compartment of the expandable member is deflated. In the deflated condition the piston-cylinder assembly lacks the freedom of mobility to align itself perpendicularly to the long axis of the swallowable device. Thereby, a pre-stressed condition is created such that when the second compartment is inflated later during use the piston-cylinder assembly will naturally re-align itself in a perpendicular fashion to the long axis of the swallowable device and the intestinal wall.

In some embodiments, the needle lumen providing access to the exterior of the second compartment of the expandable member assembly may have a covering or a film. This covering or film prevents the tissue penetrating member disposed within from advancing out of the delivery mechanism until sufficient pressure has been achieved inside the second compartment of the expandable member, such that the piston supplies enough force to advance the tissue penetrating member through the film or covering.

In some embodiment the delivery mechanism comprises an array of piston-cylinder assemblies each configured to advance a tissue penetrating member into the intestinal wall. The array of piston-cylinder assemblies may share a common inflation manifold configured to direct gas to each piston of the array of piston-cylinder assemblies. The common manifold may have a central lumen in communication with each piston of the array. The central lumen of the common inflation manifold may be coupled to a dedicated inflation balloon wherein, a chemical reaction produces a gas to pressurize the common inflation manifold thereby driving each cylinder of the array, in order to advance multiple tissue penetrating members. Each piston-cylinder assembly of the array may have an independent pressure release latch, each configured to prevent movement of the piston in the cylinder until a specified pressure is reached in the common inflation manifold. The pressure-release latches may permit movement of the piston at different specified pressures in order to control the timing of advancement of the tissue penetrating members.

Embodiments of the swallowable device may further comprise a deflation valve assembly configure to deflate the expandable member assembly after delivery of the therapeutic agent. The deflation valve assembly may comprise an O-ring surrounding a dissolvable pinch valve. The pinch valve isolates an opening in the expandable member assembly that would allow gas trapped therein to escape. The dissolvable pinch valve is configured to dissolve in the intestinal tract at a point in time after the delivery of the therapeutic agent. Upon dissolution of the pinch valve the opening in the expandable member assembly is no longer isolated and the gas trapped within the expandable member assembly is free to escape, thereby deflating the expandable member assembly.

In some embodiment, the delivery mechanism comprises a delivery compartment coupled to a delivery balloon or an expandable member assembly. In the above embodiments the delivery balloon is equivalent to the second compartment of the expandable member assembly. It should be understood that this embodiment of the delivery mechanism may be combined with any of the embodiments of the swallowable device presented herewith. It should be understood that "delivery balloon" is interchangeable with "expandable member assembly" or any portion thereof such as the "second compartment of the expandable member assembly." The delivery balloon is inflated by a chemical reaction producing a gas within. The delivery compartment comprises an upper portion facing a lower portion. The upper portion is typically in an abutted condition with the intestinal wall. The lower portion being coupled to the delivery balloon and having one or more tissue penetrating members disposed thereon directed towards the upper portion of the delivery compartment. The upper portion of the delivery compartment has one or more puncture needles disposed thereon directed towards the lower portion of the delivery compartment. Upon inflation of the delivery balloon, the pressure inside the delivery balloon forces the upper portion and the lower portion of the delivery compartment towards each other. The one or more tissue penetrating members are driven through the upper portion into the intestinal wall. The penetrating members may have distal portions containing the therapeutic agent preparation configured to break away and remain in the intestinal wall. The upper portion of the delivery compartment may have one or more apertures arranged to allow passage of the tissue penetrating members. The puncture needles penetrate the lower portion of the delivery compartment and the delivery balloon, thereby facilitating the deflation of the delivery balloon. Typically, the one or more tissue penetrating members have lengths that are longer than the penetrating members. Preferably, the one or more tissue penetrating members are long enough relative to the one or more puncture members such that the one or more tissue penetrating members are driven into the intestinal wall before the delivery balloon is inflated. The lower portion of the delivery compartment may be fabricated to only allow puncture by the one or more puncture members after a desired pressure has been achieved in the delivery balloon. This may be done by fabricating the lower portion of the delivery compartment with a material of appropriate puncture resistance or by adjusting a thickness of the lower portion.

One aspect of the invention pertains to a method for delivering a therapeutic agent preparation into an intestinal wall of a patient's intestinal tract. The method comprises providing a swallowable capsule sized to pass through the intestinal tract. The capsule having a capsule wall at least a portion of which degrades upon exposure to a selected pH in an intestine while protecting the capsule wall from degradation in a stomach of the patient. The swallow able capsule may also have at least one expandable member assembly disposed within the capsule. The expandable member assembly comprises a first compartment in at least a partially non-expanded state, a second compartment in at least a partially non-expanded state, wherein the first and second compartments are fluidically separated by a degradable valve which degrades upon exposure to fluid in the intestinal tract. The method further comprises degrading the degradable valve with fluid in the intestinal tract thereby allowing a liquid contained in one of the compartments to mix with a reactant contained in the other compartment. A gas is the produced by the reaction of the liquid and the reactant. An example reaction would involve combining citric acid (liquid) and potassium bicarbonate (reactant) to produce $CO_2$ gas. The gas inflates at least the second compartment of the expandable member assembly. The method then further comprises orienting a cylinder piston assembly disposed inside the expandable member assembly, the cylinder-piston assembly comprising: a piston slidably disposed inside a cylinder, an interface between the piston and cylinder sealed with an O-ring. The cylinder may be coupled to the wall of the second compartment and may be in communication with a needle lumen. The needle lumen provides access to the exterior of the second compartment. The cylinder-piston assembly is oriented such that the needle lumen is perpendicular to the intestinal wall. The needle lumen, being in communication with the cylinder is typically aligned with the cylinder. The piston is driven inside the cylinder towards the exterior of the second compartment with pressure from the gas. This drives a tissue penetrating member disposed in the needle lumen into the intestinal wall. The driving is accomplished by coupling the piston to the tissue penetrating member with a piston rod, the piston rod sized to be slidable inside the needle lumen. The tissue penetrating member comprises at least the therapeutic agent preparation.

Another aspect of the invention provides methods for the delivery of drugs and the therapeutic agents into the walls of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection due to chemical breakdown in the stomach e.g., growth hormone, parathyroid hormone, insulin, interferons (for treatment of MS and other conditions) and other like compounds. Suitable drugs and other therapeutic agents which can be delivered by embodiments of invention include various antibodies (e.g., HER 2 antibodies), chemotherapeutic agents (e.g., interferon), insulin and related compounds for treating diabetes, glucagon like peptides (e.g., GLP-1, exenatide), parathyroid hormones, growth hormones (e.g., IFG (insulin-like growth factor) and other growth factors), immune suppression agents (e.g., cyclosporines, cortisones, etc.), vaccines and anti-parasitic agents such as various anti-malarial agents. In specific embodiments, embodiments of the swallowable capsule can be used to delivery therapeutically effective amounts of the monoclonal antibody adalimumab for the treatment of various autoimmune related disorders such as rheumatoid arthritis. The dosage of this or particular therapeutic agent can be titrated for the patient's weight, age, condition or other parameter.

In various method embodiments of the invention, embodiments of the swallowable drug delivery device can be used to deliver a plurality of drugs for the treatment of multiple conditions or for the treatment of a particular condition (e.g., a mixture of protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc., drugs can be absorbed through the intestinal wall at different rates, resulting in different pharmacokinetic distribution curves. Embodiments of the invention address this issue by injecting the desired drug mixtures at about the same time. This in turn, improves the pharmacokinetics and thus, the efficacy of the selected mixture of drugs.

Another aspect of the invention provides therapeutic agent preparations for delivery into the wall of the small intestine (or other luminal wall in the intestinal tract) using embodiments of the swallowable device described herein. The preparation comprises a therapeutically effective dose of at least one therapeutic agent (e.g., insulin, an anti-seizure compound, NSAIDs, an antibiotic, etc.). It may comprise a solid, liquid or combination of both and can include one or more pharmaceutical excipients. The preparation has a shape and material consistency to be contained in embodiments of the swallowable capsule, delivered from the capsule into the lumen wall and degrade within the lumen wall to release the dose of therapeutic agent. The preparation may also have a selectable surface area to volume ratio so as enhance or otherwise control the rate of degradation of the preparation in the wall of the small intestine or other body lumen. In many embodiments, the release element comprises a material configured to degrade upon exposure to chemical conditions in the small or large intestine such as pH. Further details of these and other embodiments and aspects of the invention are described more fully below, with reference to the attached drawing figures.

BRIEF DESCRIPTION OF THE DRAWINGS

FIGS. 2A and 2B are lateral view illustrating an embodiment of a capsule for the swallowable drug delivery device including a cap and a body coated with pH sensitive bio-degradable coatings, FIG. 2A shows the capsule in an unassembled state and FIG. 2B in an assembled state.

FIG. 3A shows an embodiment of the assembly for a single dome configuration of the deployment balloon; and FIG. 3B shows an embodiment of the assembly for dual dome configuration of the deployment balloon;

FIG. 4A shows the balloon in a non-inflated state with the separation valve closed; FIG. 4B shows the balloon with valve open and mixing of the chemical reactants; and FIG. 4C shows the balloon in an inflated state.

FIG. 5D, pertains to the final folding step unique to dual dome configurations; FIG. 5E, pertains to a folding step unique to single dome configurations; and FIGS. 5F and 5G are orthogonal views pertaining to the final folding step unique to single dome configurations.

FIG. 8E shows the tissue penetrating member and shaped drug section prior to assembly; and FIG. 8F after assembly.

FIGS. 10A-10I provides assorted views illustrating a method of operation of swallow able device to deliver medication to the intestinal wall.

FIG. 15A shows the capsule prior to inflation and FIG. 15B shows the capsule broken into pieces by the inflation of the balloon.

DETAILED DESCRIPTION OF THE INVENTION

Figure 1A:
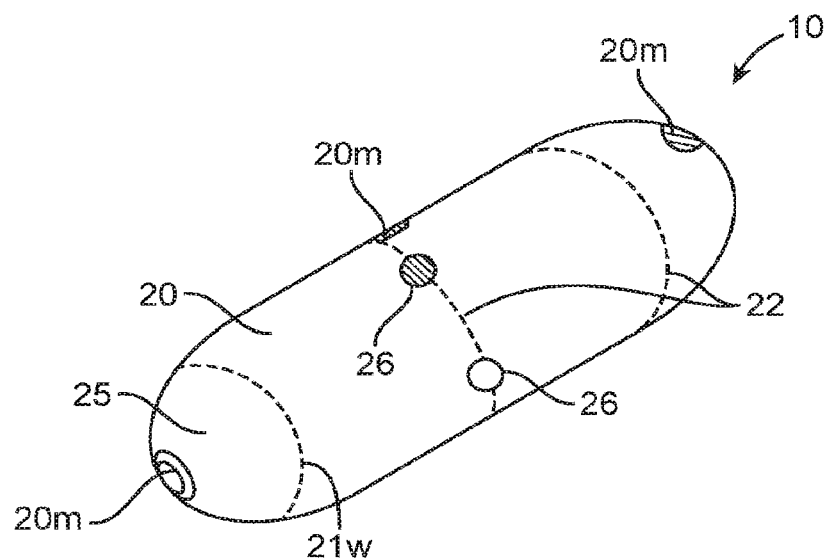
FIG. 1A is a lateral viewing showing an embodiment of a swallowable drug delivery device.

Embodiments of the invention provide devices, systems and methods for delivering medications in to various locations in the body. As used herein, the term "medication" refers to a medicinal preparation in any form which can include drugs or other therapeutic agents as well as one or more pharmaceutical excipients. Many embodiments provide a swallowable device for delivering medication within the GI tract. Particular embodiments provide a swallowable device such as a capsule for delivering medications to the wall of the small intestine or other GI organ.

Referring now to FIGS. 1-9, an embodiment of a device 10 for the delivery of medication 100 to a delivery site DS in the gastro-intestinal (GI) tract, comprises a capsule 20 sized to be swallowed and pass through the intestinal tract, a deployment member 30, one or more tissue penetrating members 40 containing medication 100, a deployable aligner 60 and a delivery mechanism 70. The deployable aligner 60 is positioned within the capsule and configured to align the capsule with the intestine such as the small intestine. Typically, this will entail aligning a longitudinal axis of the capsule with a longitudinal axis of the intestine; however, other alignments are also contemplated. The delivery mechanism 70 is configured for delivering medication 100 into the intestinal wall and will typically include a delivery member 72 such as an expandable member. The deployment member 30 is configured for deploying at least one of the aligner 60 or the delivery mechanism 70. As will be described further herein, all or a portion of the capsule wall is degradable by contact with liquids in the GI tract so as to allow those liquids to trigger the delivery of medication 100 by device 10. As used herein, "GI tract" refers to the esophagus, stomach, small intestine, large intestine and anus, while "Intestinal tract" refers to the small and large intestine. Various embodiments of the invention can be configured and arranged for delivery of medication 100 into both the intestinal tract as well as the entire GI tract.

Device 10 including tissue penetrating member 40 can be configured for the delivery of liquid, semi-liquid or solid forms of medication 100 or combinations of all three. Whatever the form, medication 100 desirably has a material consistency allowing the medication to be advanced out of device 10, into the intestinal wall (small or large intestine) or other luminal wall in the GI tract and then degrade within the intestinal wall to release the drug or other therapeutic agent 101. The material consistency of medication 100 can include one or more of the hardness, porosity and solubility of the preparation (in body fluids). The material consistency can be achieved by selection and use of one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art.

Figure 1B:
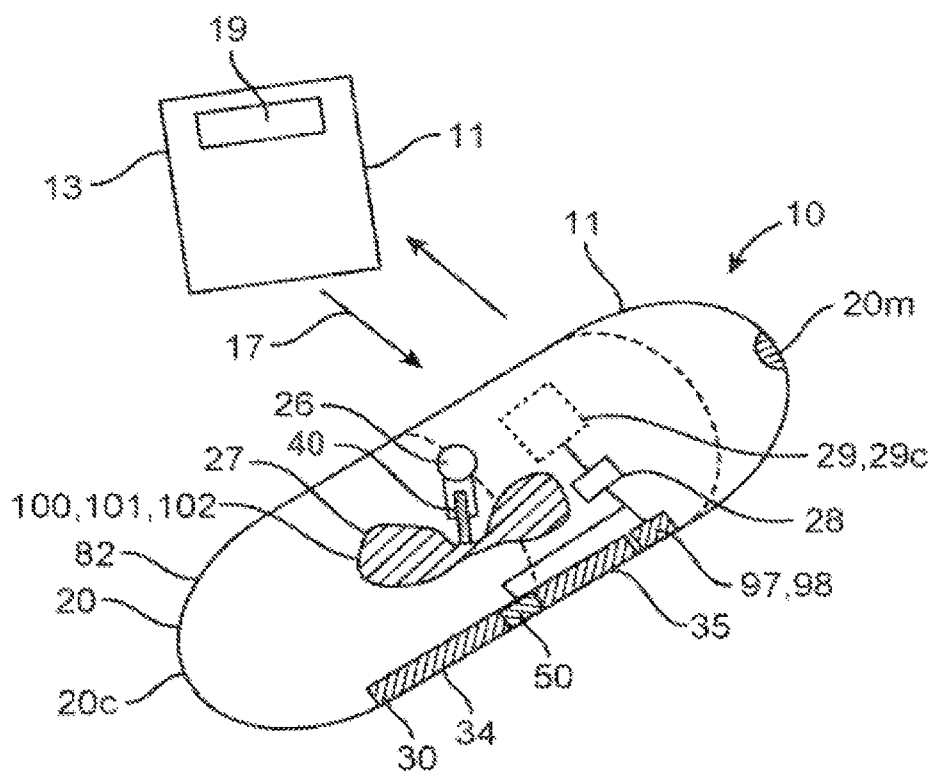
FIG. 1B is a lateral viewing showing an embodiment of a system including a swallowable drug delivery device.
Figure 1C:
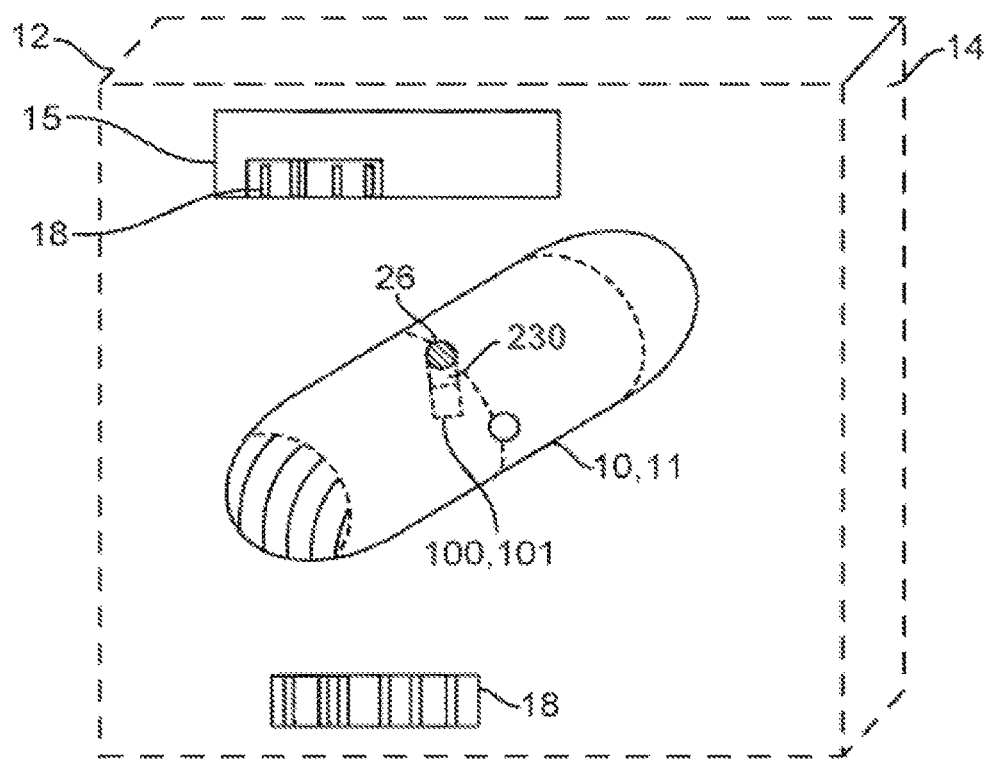
FIG. 1C is a lateral viewing showing an embodiment of a kit including a swallowable drug delivery device and a set of instructions for use.
Figure 1D:
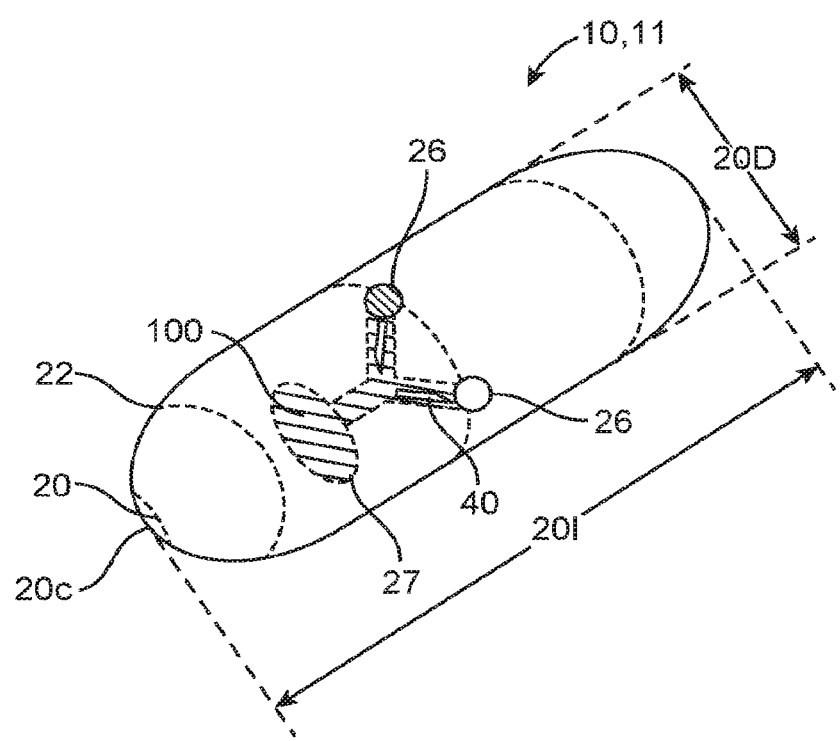
FIG. 1D is a lateral viewing showing an embodiment of a swallowable drug delivery device including a drug reservoir.
Figure 1E:
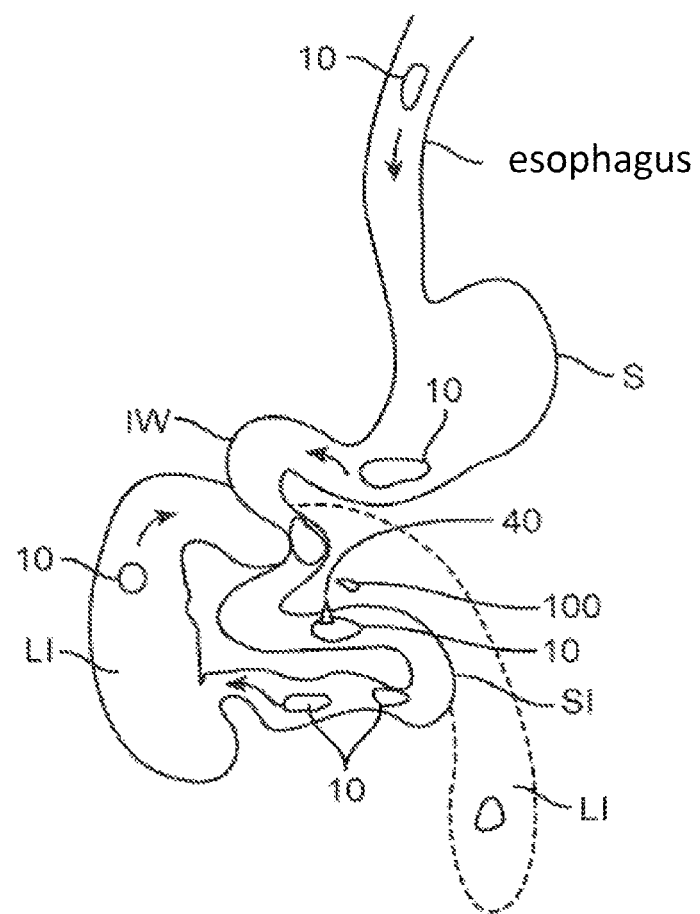
FIG. 1E is a lateral viewing illustrating use of an embodiment of a swallowable drug delivery device including transit of device in the GI tract and operation of the device to deliver drug.

A system 11 for delivery of medication 100 into the wall of the small intestine or other location within the intestinal tract or GI tract, may comprise device 10 which contains one or more medications 100 for the treatment of a selected condition or conditions. In some embodiments, the system may include a hand held device 13, described herein for communicating with device 10 as is shown in the embodiment of FIG. 1B. In many embodiments, system 11 may also be configured as a kit 14 including system 11 and a set of instructions for use 15 which are packaged in packaging 12 as is shown in the embodiment of FIG. 1C. The instructions can indicate to the patient when to take the device 10 relative to one or more events such as the ingestion of a meal or a physiological measurement such as blood glucose, cholesterol, etc. In such embodiments, kit 14 can include multiple devices 10 containing a regimen of medications 100 for a selected period of administration, e.g., a day, week, or multiple weeks depending upon the condition to be treated (e.g., treatment of cancer by a course of interferon treatment, treatment of an autoimmune disease such as or psoriasis, multiple sclerosis or arthritis by immune suppression agents).

Capsule 20 is sized to be swallowed and pass through the intestinal tract. The size can also be adjusted depending upon the amount of drug to be delivered as well as the patient's weight and adult vs. pediatric applications. Typically, the capsule will have a tubular shape with curved ends similar to a vitamin. In these and related embodiments, capsule lengths 20L can be in the range of 0.5 to 2 inches and diameters 20D in the range of 0.1 to 0.5 inches with other dimensions contemplated. The capsule 20 includes a capsule wall 21 w, having an exterior surface 25 and an interior surface 24 defining an interior space or volume 24v. In some embodiments, the capsule wall 21 w can include one or more apertures 26 sized for the outward advancement of tissue penetrating members 40 via needle lumen 230. In addition to the other components of device 10, (e.g., the expandable member etc.), the interior volume can include one or more compartments or reservoirs 27.

The capsule can be fabricated from various biodegradable gelatin materials known in the pharmaceutical arts, but can also include various enteric coatings 20c, configured to protect the cap from degradation in the stomach (due to acids etc.), and then subsequently degrade in the in higher pH's found in the small intestine or other area of the intestinal tract. In various embodiments, the capsule 20 can be formed from multiple portions one or more of which may be biodegradable. In many embodiments, capsule 20 can be formed from two portions 20p such as a body portion 20p" (herein body 20p") and a cap portion 20p' (herein cap 20p'), where the cap fits onto the body, e.g., by sliding over or under the body (with other arrangements also contemplated). One portion such as the cap 20p' can include a first coating 20c' configured to degrade above a first pH (e.g., pH 5.5) and the second portion such as the body 20p" can include a second coating 20c" configured to degrade above a second higher pH (e.g. 6.5). Both the interior 24 and exterior 25 surfaces of capsule 20 are coated with coatings 20c' and 20c" so that that either portion of the capsule will be substantially preserved until it contacts fluid having the selected pH. For the case of body 20p" this allows the structural integrity of the body 20p" to be maintained so as to keep balloon 72 inside the body portion and not deployed until balloon 30 has expanded. Coatings 20c' and 20c" can include various methacrylate and ethyl acrylate based coatings such as those manufactured by Evonik Industries under the trade name EUDRAGIT. These and other dual coating configurations of the capsule 20 allows for mechanisms in one portion of capsule 20 to be actuated before those in the other portion of the capsule. This is due to the fact that intestinal fluids will first enter those portions where the lower pH coating has degraded thus actuating triggers which are responsive to such fluids (e.g., degradable valves). In use, such dual coating embodiments for capsule 20 provide for targeted drug delivery to a particular location in the small intestine (or other location in the GI tract), as well as improved reliability in the delivery process. This is due to the fact that deployment of a particular component, such as aligner 60, can be configured to begin in the upper area of the small intestine (e.g., the duodenum) allowing the capsule to be aligned within the intestine for optimal delivery of the drug (e.g., into the intestinal wall) as well as providing sufficient time for deployment/actuation of other components to achieve drug delivery into the intestinal wall while the capsule is still in the small intestine or other selected location.

As is discussed above, one or more portions of capsule 20 can be fabricated from various biocompatible polymers known in the art, including various biodegradable polymers which in a preferred embodiment can comprise cellulose, gelatin materials PLGA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

Use of biodegradable materials for capsule 20, including biodegradable enteric materials allows the capsule to degrade in whole or part to facilitate passage through the GI system before, during or after drug delivery. As is described in further detail herein, in various embodiments, capsule 20 can include seams 22 of bio-degradable material so as to controllably degrade into smaller pieces 23 which are more easily passed through the intestinal tract.

In various embodiments, the wall 20w of the capsule is degradable by contact with liquids in the GI tract for example liquids in the small intestine. In preferred embodiments, the capsule wall is configured to remain intact during passage through the stomach, but then to be degraded in the small intestine. In one or more embodiments, this can be achieved by the use of an outer coating or layer 20c on the capsule wall 20w, which only degrades in the higher pH's found in the small intestine and serves to protect the underlying capsule wall from degradation within the stomach before the capsule reaches the small intestine (at which point the drug delivery process is initiated by degradation of the coating as is described herein). In use, such coatings allow for the targeted delivery of a therapeutic agent in a selected portion of the intestinal tract such as the small intestine.

In various embodiments, capsule 20 can include various radio-opaque, echogenic or other materials for location of the device using one or more medical imaging modalities such as fluoroscopy, ultrasound, MRI, etc. In specific embodiments, all or a portion of the capsule can include radio-opaque/echogenic markers 20m as is shown in the embodiment of FIGS. 1a and 1b. Suitable materials for radio-opaque markers 20m include barium sulfate, compounds, titanium dioxide and compounds thereof. In use, such materials allow for the location of device 10 in the GI tract, as well as its state of deployment (e.g., a distinctive marker can be positioned on cap 20p' and another on body 20p'' allowing for determination if the deployment balloon 30 (discussed below) has inflated but the delivery balloon 72 has not). They can also be used allow for the determination of transit times of the device through the GI tract. Such information can be used to titrate dosages of drug for a particular patient, as well as provide information on when they should take a particular drug after an event such as ingestion of a meal in the case of insulin taken for treatment of diabetes. Markers 20m can also be positioned on the capsule 20 to allow the physician to determine if the capsule is intact, or has broken up.

As is discussed further herein, in many embodiments, one or more of the deployment member 30, delivery member 72 or deployable aligner 60, may correspond to an expandable balloon that is shaped and sized to fit within capsule 20. Accordingly, for ease of discussion, deployment member 30, delivery member 72 and deployable aligner 60 will now be referred to as balloon 30, 60 and 72; however, it should be appreciated that other devices including various expandable devices are also contemplated for these elements and may include for example, various shape memory devices (e.g., an expandable basket made from shape memory biodegradable polymer spires), expandable piezo electric devices, and/or chemically expandable devices having an expanded shape and size corresponding to the interior volume 24v of the capsule 20.

One or more of balloons 30, 60 and 72 can comprise various polymers known in the medical device arts. In preferred embodiments such polymers can comprise one or more types of polyethylene (PE) which may correspond to low density PE(LDPE), linear low density PE (LLDPE), medium density PE (HDPE) and high density PE (HDPE) and other forms of polyethylene known in the art. In one more embodiments using polyethylene, the material may be cross-linked using polymer irradiation methods known in the art. In particular embodiments, radiation-based cross-linking may be used as to control the inflated diameter and shape of the balloon by decreasing the compliance of the balloon material. The amount or radiation may be selected to achieve a particular amount of cross linking to in turn produce a particular amount of compliance for a given balloon, e.g., increased irradiation can be used to produce stiffer less compliant balloon material. Other suitable polymers can include PET (polyethylene terephthalate), silicone and polyurethane. In various embodiments, balloons 30, 60 and 72 may also include various radio-opaque materials known in the art such as barium sulfate to allow the physician to ascertain the position and physical state of the balloon (e.g., un-inflated, inflated or punctures). Balloons 30, 60 and 72 can be fabricated using various balloon blowing methods known in the balloon catheters arts (e.g., mold blowing, free blowing, etc.) to have a shape and size which corresponds approximately to the interior volume 24v of capsule 20. In various embodiments one or more of balloons 30, 60 and 72 and various connecting features (e.g., connecting tubes) can have a unitary construction being formed from a single mold. Embodiments employing such unitary construction provide the benefit of improved manufacturability and reliability since fewer joints must be made between one or more components of device 10.

Figure 3A:
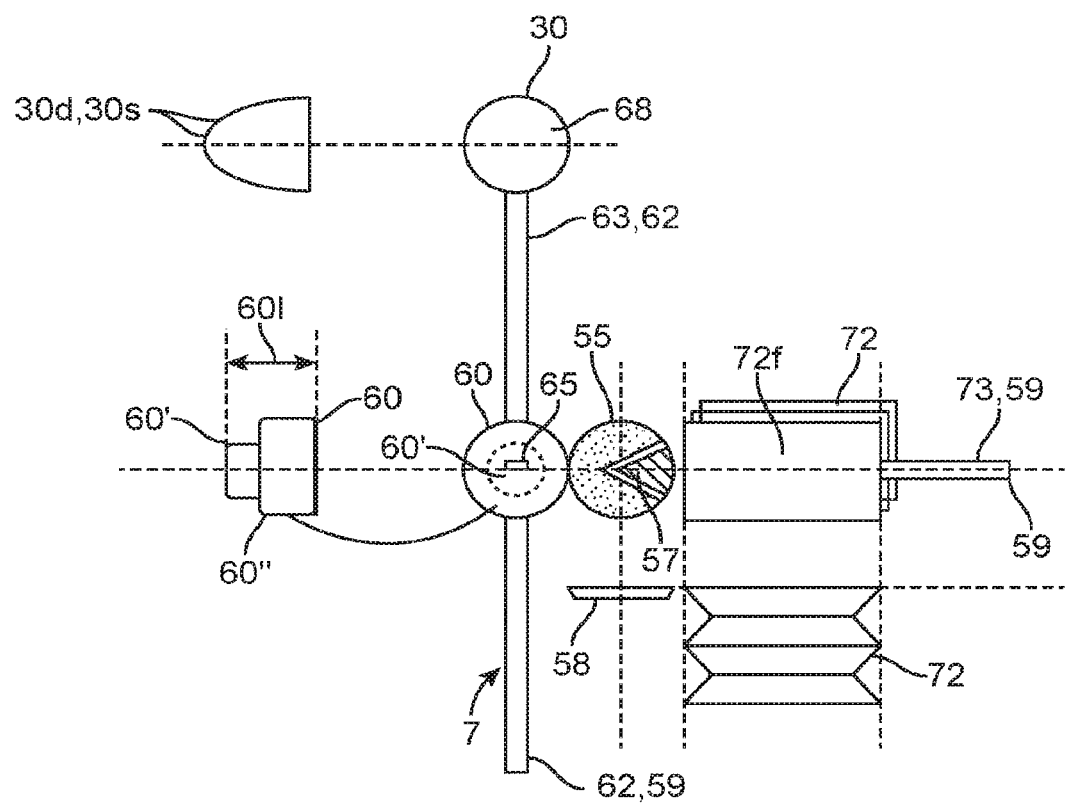
FIGS. 3A and 3B illustrate embodiments of unfolded multi balloon assemblies containing a deployment balloon, an aligner balloon, a delivery balloon and assorted connecting tubes.
Figure 3B:
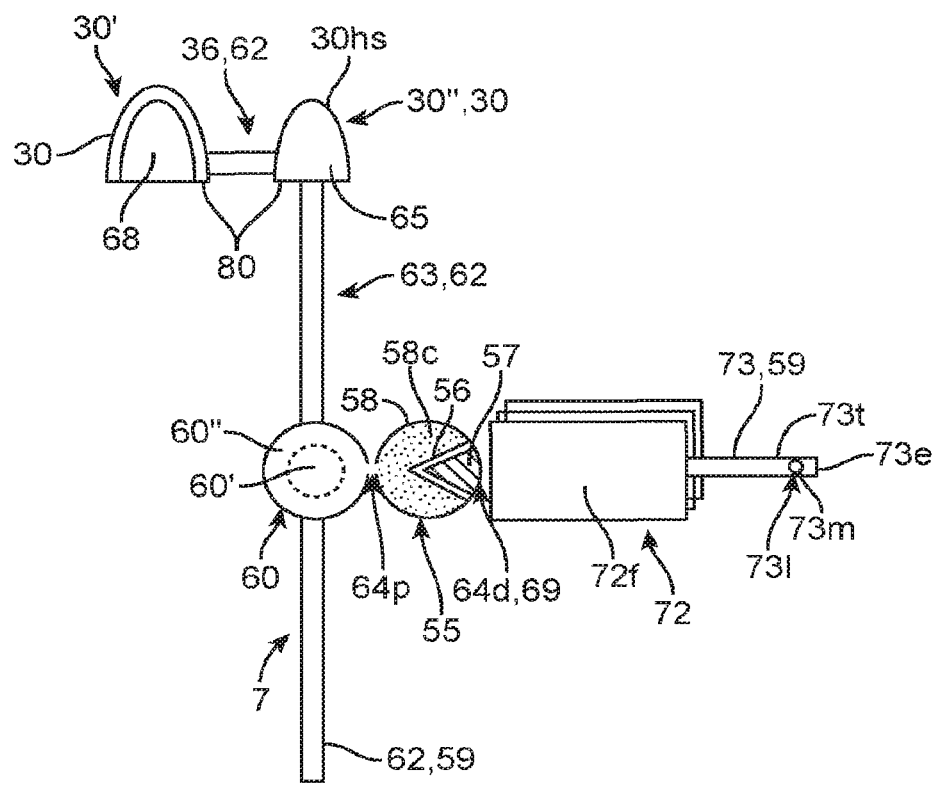
Figure 3C:
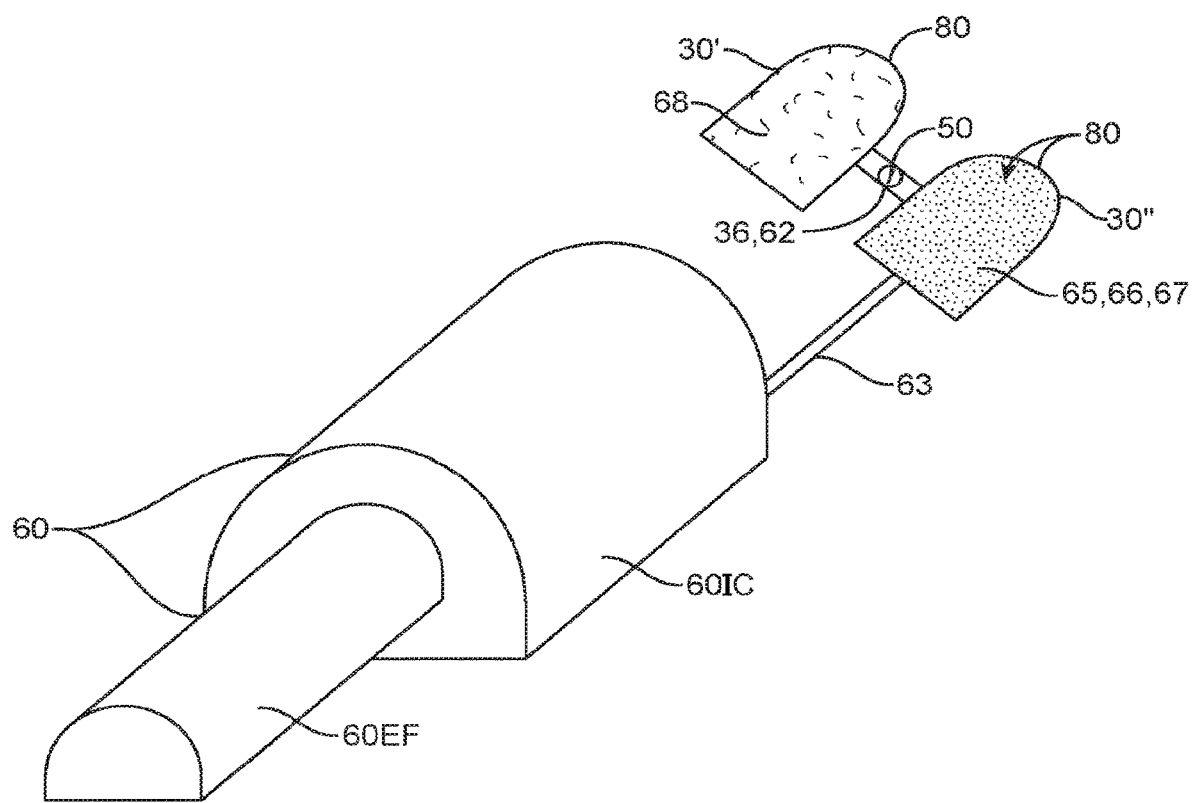
FIG. 3C is a perspective views illustrating embodiments of a nested balloon configuration which can be used for one or more embodiments of the balloons described herein including the aligner balloon.

Suitable shapes for balloons 30, 60 and 72 include various cylindrical shapes having tapered or curved end portions (an example of such a shape including a hot dog). In some embodiments, the inflated size (e.g., diameter) of one or more of balloons 30, 60 and 72, can be larger than capsule 20 so as to cause the capsule to come apart from the force of inflation, (e.g., due to hoop stress). In other related embodiments, the inflated size of one or more of balloons 30, 60 and 72 can be such that when inflated, i) the capsule 20 has sufficient contact with the walls of the small intestine so as to elicit a peristaltic contraction causing contraction of the small intestine around the capsule, and/or ii) the folds of the small intestine are effaced to allow contact. Both of these results allow for improved contact between the capsule/balloon surface and the intestinal wall so as deliver tissue penetrating members 40 over a selected area of the capsule and/or delivery balloon 72. Desirably, the walls of balloons 30, 60 and 72 will be thin and can have a wall thickness in the range of 0.005 to 0.0001" more preferably, in the range of 0.005 to 0.0001, with specific embodiments of 0.004, 0.003, 0.002, 0.001, and 0.0005). Additionally in various embodiments, one or more of balloon 30, 60 or 72 can have a nested balloon configuration having an inflation chamber 60IC and extended finger 60EF as is shown in the embodiments of FIG. 3C. The connecting tubing 63, connecting the inflation chamber 60IC can be narrow to only allow the passage of gas 68, while the connecting tubing 36 coupling the two halves of balloon 30 can be larger to allow the passage of water.

As indicated above, the aligner 60 will typically comprise an expandable balloon and for ease of discussion, will now be referred to as aligner balloon 60 or balloon 60. Balloon 60 can be fabricated using materials and methods described above. It has an unexpanded and expanded state (also referred to as a deployed state). In its expanded or deployed state, balloon 60 extends the length of capsule 20 such that forces exerted by the peristaltic contractions of the small intestine SI on capsule 20 serve to align the longitudinal axis 20LA of the capsule 20 in a parallel fashion with the longitudinal axis LAI of the small intestine SI. This in turn serves to align the shafts of tissue penetrating members 40 in a perpendicular fashion with the surface of the intestinal wall IW to enhance and optimize the penetration of tissue penetrating members 40 into the intestinal wall IW. In addition to serving to align capsule 20 in the small intestine, aligner 60 is also configured to push delivery mechanism 70 out of capsule 20 prior to inflation of delivery balloon 72 so that the delivery balloon and/or mechanism is not encumbered by the capsule. In use, this push out function of aligner 60 improves the reliability for delivery of the therapeutic agent since it is not necessary to wait for particular portions of the capsule (e.g., those overlying the delivery mechanism) to be degraded before drug delivery can occur.

Balloon 60 may be fluidically coupled to one or more components of device 10 including balloons 30 and 72 by means of polymer tube or other fluidic couplings 62 which may include a tube 63 for coupling balloons 60 and 30 and a tube 64 for coupling balloon 60 and balloon 72. Tube 63 is configured to allow balloon 60 to be expanded/inflated by pressure from balloon 30 (e.g., pressure generated the mixture of chemical reactants within balloon 30) and/or otherwise allow the passage of liquid between balloons 30 and 60 to initiate a gas generating chemical reaction for inflation of one or both of balloons 30 and 60. Tube 64 connects balloon 60 to 72 so as to allow for the inflation of balloon 72 by balloon 60. In many embodiments, tube 64 includes or is coupled to a control valve 55 which is configured to open at a selected pressure so as to control the inflation of balloon 72 by balloon 60. Tube 64 may thus comprise a proximal portion 64p connecting to the valve and a distal portion 64d leading from the valve. Typically, proximal and distal portions 64p and 64d will be connected to a valve housing 58 as is described below.

Valve 55 may comprise a triangular or other shaped section 56 of a material 57 which is placed within a chamber 58c of a valve housing 58 (alternately, it may be placed directly within tubing 64). Section 57 is configured to mechanically degrade (e.g., tears, shears, delaminates, etc.) at a selected pressure so as to allow the passage of gas through tube 64 and/or valve chamber 58c. Suitable materials 57 for valve 55 can include bees wax or other form of wax and various adhesives known in the medical arts which have a selectable sealing force/burst pressure. Valve fitting 58 will typically comprise a thin cylindrical compartment (made from biodegradable materials) in which section 56 of material 57 is placed (as is shown in the embodiment of FIG. 3B) so as to seal the walls of chamber 58c together or otherwise obstruct passage of fluid through the chamber. The release pressure of valve 55 can be controlled through selection of one or more of the size and shape of section 56 as well as the selection of material 57 (e.g., for properties such as adhesive strength, shear strength etc.). In use, control valve 55 allows for a sequenced inflation of balloon 60 and 72 such that balloon 60 is fully or otherwise substantially inflated before balloon 72 is inflated. This, in turn, allows balloon 60 to push balloon 72 along with the rest of delivery mechanism 70 out of capsule 20 (typically from body portion 20p') before balloon 72 inflates so that deployment of tissue penetrating members 40 is not obstructed by capsule 20 In use, such an approach improves the reliability of the penetration of tissue penetrating members 40 into intestinal wall IW both in terms of achieving a desired penetration depth and delivering greater numbers of the penetrating members 40 contained in capsule 20 since the advancement of the members into intestinal wall IW is not obstructed by capsule wall 20w.

As is describe above, the inflated length 60l of the aligner balloon 60 is sufficient to have the capsule 20 become aligned with the lateral axis of the small intestine from peristaltic contractions of the intestine. Suitable inflated lengths 60l for aligner 60 can include a range between about ½ to two times the length 20l of the capsule 20 before inflation of aligner 60. Suitable shapes for aligner balloon 60 can include various elongated shapes such as a hotdog like shape. In specific embodiments, balloon 60 can include a first section 60' and a second section 60", where expansion of first section 60' is configured to advance delivery mechanism 70 out of capsule 20 (typically out of and second section 60" is used to inflate delivery balloon 72. In these and related embodiments, first and second sections 60' and 60" can be configured to have a telescope-style inflation where first section 60' inflates first to push mechanism 70 out of the capsule (typically from body portion 20p') and second section 60" inflates to inflate delivery member 72. This can be achieved by configuring first section 60' to have smaller diameter and volume than second section 60" such that first section 60' inflates first (because of its smaller volume) and with second section 60" not inflating until first section 60' has substantially inflated. In one embodiment, this can be facilitated by use of a control valve 55 (described above) connecting sections 60' and 60" which does not allow passage of gas into section 60" until a minimum pressure has been reached in section 60'. In some embodiments, the aligner balloon can contain the chemical reactants which react upon mixture with water or other liquid from the deploying balloon.

In many embodiments, the deployment member 30 will comprise an expandable balloon, known as the deployment balloon 30. In various embodiments, deployment balloon 30 is configured to facilitate deployment/expansion of aligner balloon 60 by use of a gas, for example, generation of a gas 69 from a chemical. The gas may be generated by the reaction of solid chemical reactants 65, such as an acid 66 (e.g., citric acid) and a base 67 (e.g., potassium bicarbonate, sodium bicarbonate and the like) which are then mixed with water or other aqueous liquid 68. The amount of reactants may be chosen using stoichiometric methods to produce a selected pressure in one or more of balloons 30, 60 and 72. The reactants 65 and liquids can be stored separately in balloon 30 and 60 and then brought together in response to a trigger event, such as the pH conditions in the small intestine. The reactants 65 and liquids 68 can be stored in either balloon, however in preferred embodiments, liquid 68 is stored in balloon 30 and reactants 65 in balloon 60. To allow for passage of the liquid 68 to start the reaction and/or the resulting gas 69, balloon 30 may be coupled to aligner balloon 60 by means of a connector tube 63 which also typically includes a separation means 50 such as a degradable valve 50 described below. For embodiments where balloon 30 contains the liquid, tube 63 has sufficient diameter to allow for the passage of sufficient water from balloon 30 to balloon 60 to produce the desired amount of gas to inflate balloon 60 as well inflate balloon 72. Also when balloon 30 contains the liquid, one or both of balloon 30 and tube 63 are configured to allow for the passage of liquid to balloon 60 by one or more of the following: i) the compressive forced applied to balloon 30 by peristaltic contractions of the small intestine on the exposed balloon 30; and ii) wicking of liquid through tube 63 by capillary action.

Figure 6A:
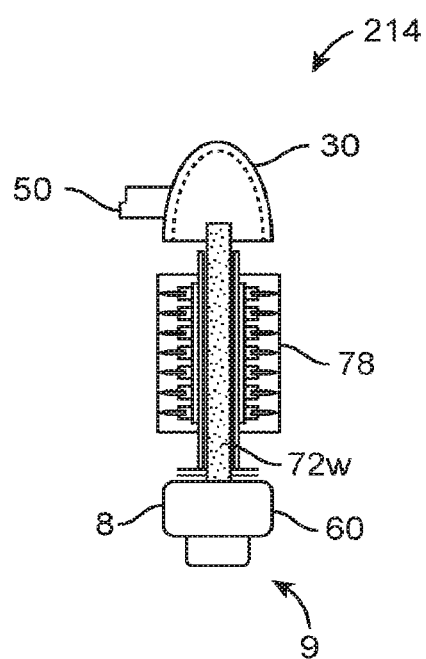
FIGS. 6A and 6B are orthogonal views illustrating embodiments of the final folded multi balloon assembly with the attached delivery assembly.
Figure 6B:
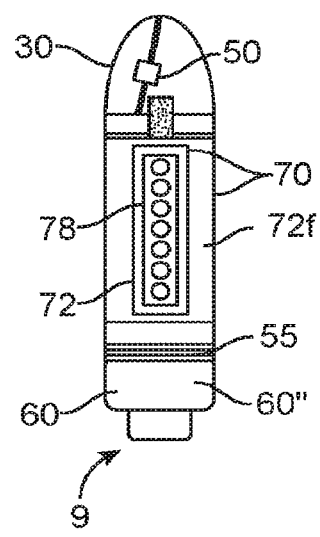
Figures 7A, 7B:
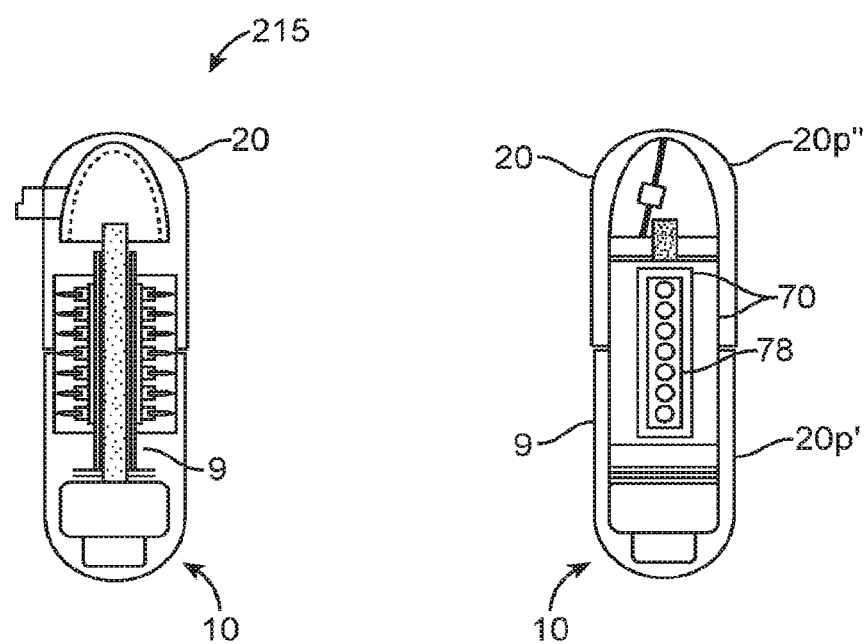
FIGS. 7A and 7B are orthogonal transparent views illustrating embodiments of the final folded multi balloon assembly inserted into the capsule.

Tube 63 will typically include a degradable separation valve or other separation means 50 which separates the contents of balloon 30, (e.g., water 58) from those of balloon 60 (e.g., reactants 65) until the valve degrades. Valve 50 can be fabricated from a material such as maltose, which is degradable by liquid water so that the valve opens upon exposure to water along with the various liquids in the digestive tract. It may also be made from materials that are degradable responsive to the higher pH's found in the intestinal fluids such as methacrylate based coatings. The valve is desirably positioned at location on tube 63 which protrudes above balloon 30 and/or is otherwise sufficient exposed such that when cap 20p' degrades the valve 50 is exposed to the intestinal liquids which enter the capsule. In various embodiments, valve 50 can be positioned to lie on the surface of balloon 30 or even protrude above it (as is shown in the embodiments of FIGS. 6A and 6B), so that is has clear exposure to intestinal fluids once cap 20p' degrades. Various embodiments of the invention provide a number of structures for a separation valve 50, for example, a beam like structure (where the valve comprises a beam that presses down on tube 63 and/or connecting section 36), or collar type structure (where the valve comprises a collar lying over tube 63 and/or connecting section 36). Still other valve structures are also contemplated.

Balloon 30 has a deployed and a non-deployed state. In the deployed state, the deployment balloon 30 can have a dome shape 30d which corresponds to the shape of an end of the capsule. Other shapes 30s for the deployed balloon 30 are also contemplated, such as spherical, tube-shape, etc. The reactants 65 will typically include at least two reactants 66 and 67, for example, an acid such as citric acid and a base such as sodium bicarbonate, which can have about a 1:2 ratio. Other reactants 65 including other acids, e.g., ascetic acid and bases, e.g., sodium hydroxide are also contemplated. When the valve or other separation means 50 opens, the reactants mix in the liquid and produce a gas such as carbon dioxide which expands the aligner balloon 60 or other expandable member.

In an alternative embodiment shown in FIG. 3B, the deployment balloon 30 can actually comprise a first and second balloon 30' and 30" connected by a tube 36 or other connection means 36 (e.g., a connecting section). Connecting tube 36 will typically include a separation valve 50 that is degradable by a liquid as described above and/or a liquid having a particular pH such as basic pH found in the small intestine (e.g., 5.5 or 6.5). The two balloons 30' and 30" can each have a half dome shape 30hs allowing them to fit into the end portion of the capsule when in the expanded state. One balloon can contain the chemical reactant(s) 65 (e.g., sodium bicarbonate, citric acid, etc.) the other the liquid water 68, so that when the valve is degraded the two components mix to form a gas which inflates one or both balloons 30' and 30" and in turn, the aligner balloon 60.

Figure 4A:
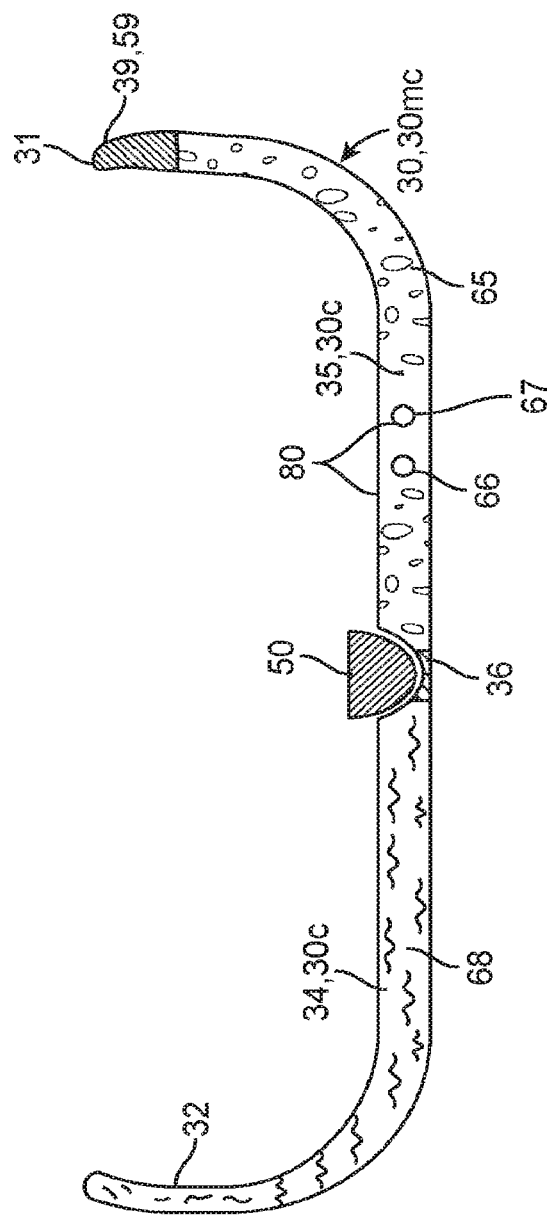
FIGS. 4A-4C are lateral views illustrating embodiments of a multi compartment deployment balloon.
Figure 4B:
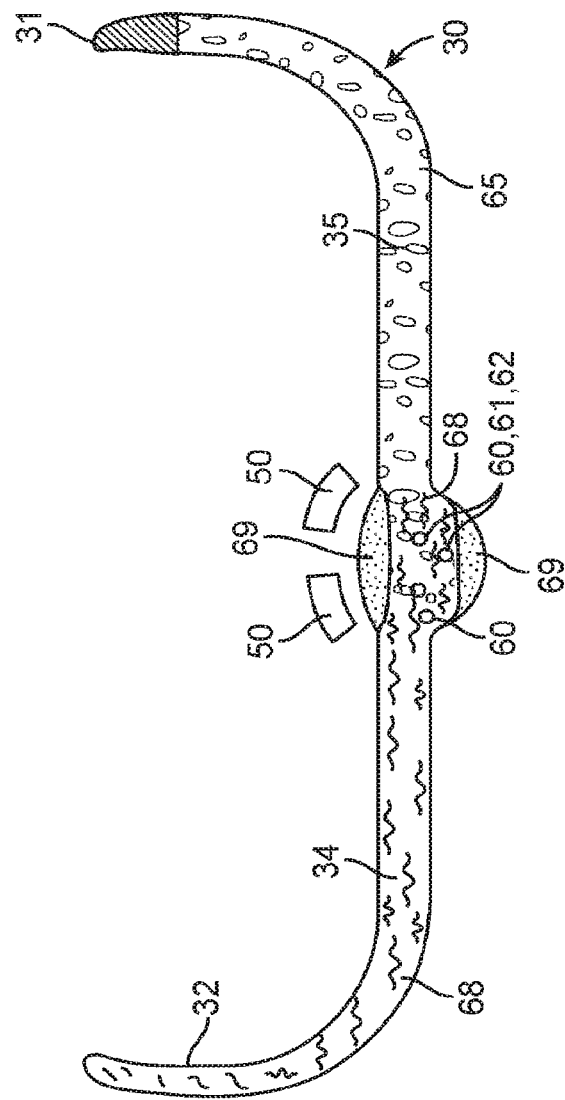
Figure 4C:
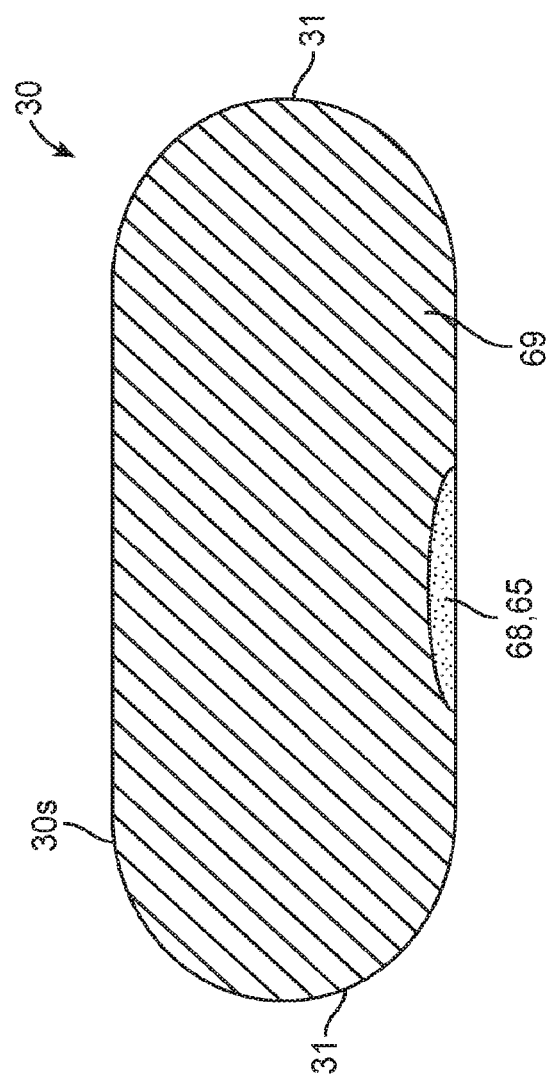

In yet another alternative embodiment, balloon 30 can comprise a multi-compartment balloon 30mc, that is formed or other constructed to have multiple compartments 30c. Typically, compartments 30c will include at least a first and a second compartment 34 and 35 which are separated by a separation valve 50 or other separation means 50 as is shown in the embodiment of FIG. 4A. In many embodiments, compartments 34 and 35 will have at least a small connecting section 36 between them which is where separation valve 50 will typically be placed. A liquid 68, typically water, can be disposed within first compartment 34 and one or more reactants 65 disposed in second compartment 35 (which typically are solid though liquid may also be used) as is shown in the embodiment of FIG. 4A. When valve 50 opens (e.g., from degradation caused by fluids within the small intestine) liquid 68 enters compartment 35 (or vice versa or both), the reactant(s) 65 mix with the liquid and produce a gas 69 such as carbon dioxide which expands balloon 30 which in turn can be used to expand one or more of balloons 60 and 72.

Reactants 65 will typically include at least a first and a second reactant, 66 and 67 for example, an acid such as citric acid and a base such as sodium bi-carbonate or potassium bicarbonate. As discussed herein, in various embodiments they may be placed in one or more of balloon 30 (including compartments 34 and 35 or halves 30' and 30") and balloon 60. Additional reactants, including other combinations of acids and bases which produce an inert gas by product are also contemplated. For embodiments using citric acid and sodium or carbonate, the ratio's between the two reactants (citric acid to potassium bicarbonate) can be in the range of about 1:1 to about 1:4, with a specific ratio of about 1:3. Desirably, solid reactants 65 have little or no absorbed water. Accordingly, one or more of the reactants, such as sodium bicarbonate or potassium bicarbonate can be pre-dried (e.g., by vacuum drying) before being placed within balloon 30. Other reactants 65 including other acids, e.g., ascetic acid and bases are also contemplated. The amounts of particular reactants 65, including combinations of reactants can be selected to produce particular pressures using known stoichiometric equations for the particular chemical reactions as well as the inflated volume of the balloon and the ideal gas law (e.g., $PV=nRT$). In particular embodiments, the amounts of reactants can be selected to produce a pressure selected one or more of balloons 30, 60 and 72 to i) achieve a particular penetration depth into the intestinal wall; ii) and produce a particular diameter for one or more of balloons 30, 60 and 72; and iii) exert a selected amount of force against intestinal wall IW. In particular embodiments, the amount and ratios of the reactants (e.g., citric acid and potassium bicarbonate) can be selected to achieve pressures in one more of the balloons 30, 60 and 72 in the range of 10 to 15 psi, with smaller and larger pressures contemplated. Again the amounts and ratios of the reactants to achieve these pressures can be determined using known stoichiometric equations.

In various embodiments of the invention using chemical reactants 65 to generate gas 69, the chemical reactants alone or in combination with the deployment balloon 30 can comprise a deployment engine for 80 deploying one or both of the aligner balloon 60 and delivery mechanism 70 including delivery balloon 72. Deployment engine 80 may also include embodiments using two deployment balloons 30 and 30" (a dual dome configuration as shown in FIG. 3B), or a multi compartment balloon 30mc as shown in FIG. 4A. Other forms of a deployment engine 80 are also contemplated by various embodiments of the invention such as use of expandable piezo-electric materials (that expand by application of a voltage), springs and other shape memory materials and various thermally expandable materials.

One or more of the expandable balloons 30, 60 and 72 will also typically include a deflation valve 59 which serves to deflate the balloon after inflation. Deflation valve 59 can comprise biodegradable materials which are configured to degrade upon exposure to the fluids in the small intestine and/or liquid in one of the compartments of the balloon so as to create an opening or channel for escape of gas within a particular balloon. Desirably, deflation valves 59 are configured to degrade at a slower rate than valve 50 to allow sufficient time for inflation of balloons, 30, 60 and 72 before the deflation valve degrades. In various embodiments, of a compartmentalized balloon 30, deflation valve 59 can correspond to a degradable section 39 positioned on an end portion 31 of the balloon as is shown in the embodiment of FIG. 4A. In this and related embodiments, when degradable section 39 degrades from exposure to the liquid, balloon wall 32 tears or otherwise comes apart providing for a high assurance of rapid deflation. Multiple degradable sections 39 can be placed at various locations within balloon wall 32.

In various embodiments of balloon 72, deflation valve 59 can correspond to a tube valve 73 attached to the end 72e of the delivery balloon 72 (opposite to the end which is coupled to the aligner balloon) as is shown in the embodiment of FIG. 3B. The tube valve 73 comprises a hollow tube 73t having a lumen that is obstructed at a selected location 731 with a material 73m such as maltose that degrades upon exposure to fluid such as the fluid in the small intestine. The location 731 of the obstructing material 73m in tube 73t is selected to provide sufficient time for the delivery balloon 72 to inflate and deliver the tissue penetrating members 40 into the intestinal wall IW before the obstructing material dissolves to open valve 73. Typically, this will be close to the end 73e of the tube 73t, but not quite so as to allow time for liquid to have to wick into the tube lumen before it reaches material 73m. According to one or more embodiments, once the deflation valve 73 opens, it not only serves to deflate the delivery balloon 72 but also the aligner balloon 60 and deployment balloon 30 since in many embodiments, all three are fluidically connected (aligner balloon being fluidically connected to delivery balloon 72 and the deployment balloon 30 being fluidically connected to aligner balloon 60). Opening of the deflation valve 73 can be facilitated by placing it on the end 72e of the delivery balloon 72 that is forced out of capsule 20 by inflation of the aligner balloon 60 so that the deflation valve has good exposure to liquids in the small intestine. Similar tube deflation valves 73 can also be positioned on one or both of aligner balloon 62 and the deployment balloon 30. In these later two cases, the obstructing material in the tube valve can be configured to degrade over a time period to allow sufficient time for inflation of delivery balloon 72 and advancement of tissue penetrating members 40 into the intestinal wall.

Additionally, as further backup for insured deflation, one or more puncture elements 82 (shown in FIG. 2A) can be attached to the inside surface 24 of the capsule such that when a balloon (e.g., balloon 30, 60, 72) fully inflates it contacts and is punctured by the puncture element 82. Puncture elements 82 can comprise short protrusions from surface 24 having a pointed tip. In another alternative or additional embodiment of a means for balloon deflation, one or more of the tissue penetrating members 40 can be directly coupled to the wall of 72w of balloon 72 and configured to tear away from the balloon when they detach, tearing the balloon wall in the process.

Figure 8A:
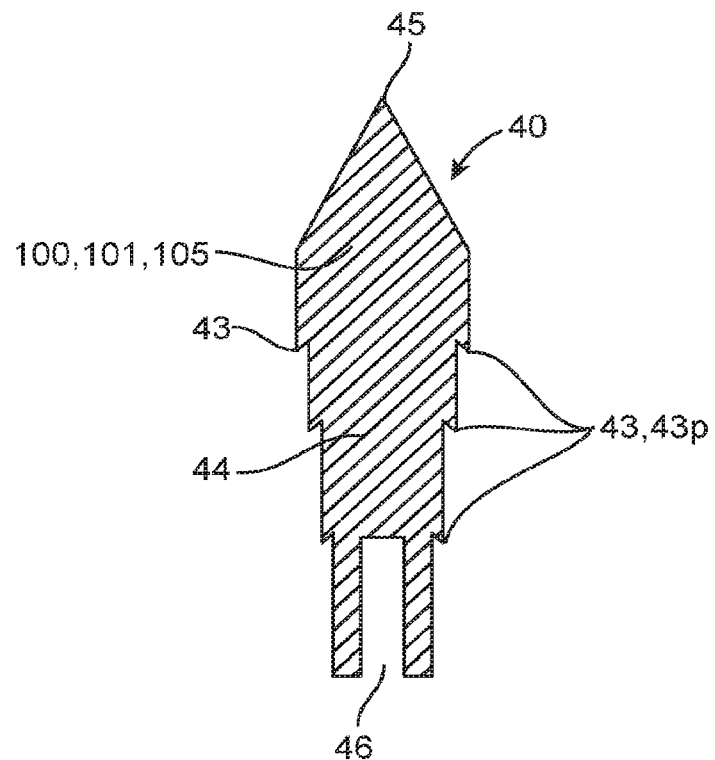
FIG. 8A is a side view of an embodiment of the tissue penetrating member.
Figure 8B:
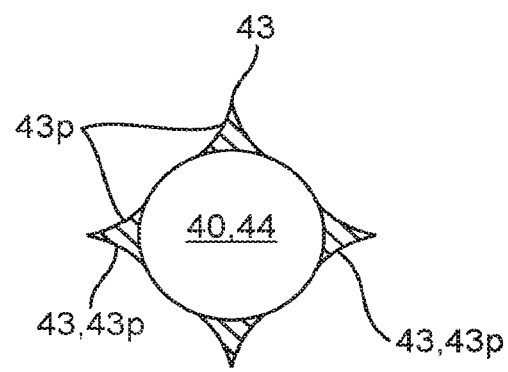
FIG. 8B is a bottom view of an embodiment of the tissue penetrating member illustrating placement of the tissue retaining features.
Figure 8C:
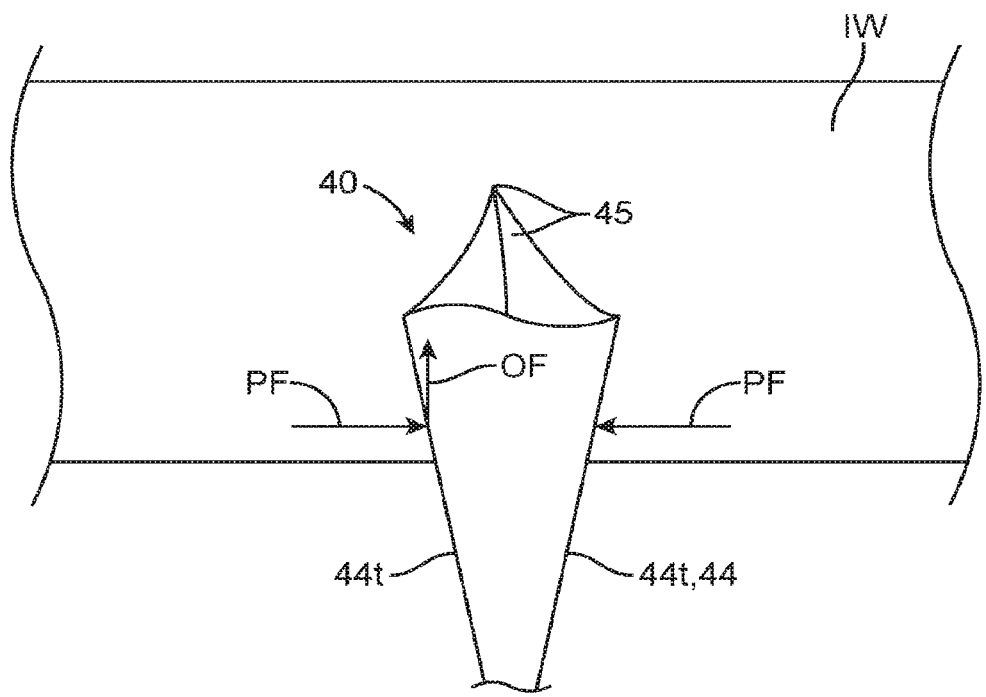
FIG. 8C is a side view of an embodiment of the tissue penetrating member having a trocar tip and inverted tapered shaft.

A discussion will now be presented of tissue penetrating members 40. Tissue penetrating member 40 can be fabricated from various drugs and other therapeutic agents 101, one or more pharmaceutical excipients (e.g., disintegrants, stabilizers, etc.) and one or more biodegradable materials which may be used to form the main structural components of tissue penetrating member 40 including shaft 44 and tip 45 discussed below. The later materials can be chosen to confer desired structural and material properties to the penetrating member (for example, column strength for insertion into the intestinal wall, or porosity and hydrophilicity for control the release of drug. Referring now to FIGS. 8A-8F, in many embodiments, the penetrating member 40 can be formed to have a shaft 44 and a needle tip 45 or other pointed tip 45 so as to readily penetrate tissue of the intestinal wall as shown in the embodiment of FIG. 8A. In preferred embodiments, tip 45 has a trocar shape as is shown in the embodiment of FIG. 8C. Tip 45 may comprise various degradable materials (within the body of the tip or as a coating), such as sucrose, maltose or other sugar which increase the hardness and tissue penetrating properties of the tip. Once placed in the intestinal wall, the penetrating member 40 is degraded by the interstitial fluids within the wall tissue so that the drug or other therapeutic agent 101 dissolves in those fluids and is absorbed into the blood stream. One or more of the size, shape and chemical composition of tissue penetrating member 40 can be selected to allow for dissolution and absorption of drug 101 in a matter of seconds, minutes or even hours. Rates of dissolution can be controlled through the use of various disintegrants known in the pharmaceutical arts. Examples of disintegrants include, but are not limited to various starches such as sodium starch glycolate and various cross linked polymers such as carboxymethyl cellulose. The choice of disintegrants can be specifically adjusted for the environment within the wall of the small intestine e.g., blood flow, average number of peristaltic contractions, etc.

Tissue penetrating member 40 will also typically include one or more tissue retaining features 43 such as a barb or hook to retain the penetrating member within the tissue of the intestinal wall IW after advancement. Retaining features 43 can be arranged in various patterns 43p to enhance tissue retention such as two or more barbs symmetrically or otherwise distributed around and along member shaft 44 as is shown in the embodiments of FIGS. 8A and 8B. Additionally, in many embodiments, penetrating member will also include a recess or other mating feature 46 for attachment to a coupling component on delivery mechanism 70.

Tissue penetrating member 40 is desirably configured to be detachably coupled to platform 75 (or other component of delivery mechanism 70), so that after advancement of the tissue penetrating member 40 into the intestinal wall, the penetrating member detaches from the balloon. Detachability can be implemented by a variety of means including: i) the snugness or fit between the opening 74 in platform 75 and the member shaft 44); ii) the configuration and placement of tissue retaining features 43 on penetrating member 40; and iii) the depth of penetration of shaft 44 into the intestinal wall. Using one or more of these factors, penetrating member 40 be configured to detach as a result of balloon deflation (where the retaining features 43 hold the penetrating member 40 in tissue as the balloon deflates or otherwise pulls back away from the intestinal wall) and/or the forces exerted on capsule 20 by a peristaltic contraction of the small intestine.

Figure 5A:
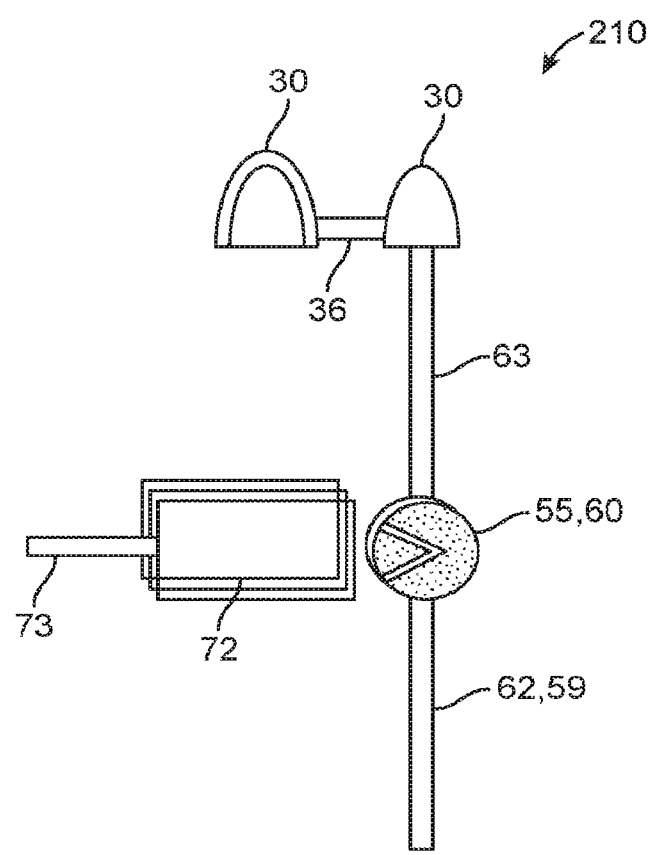
FIGS. 5A-5G are lateral views illustrating a method for folding of the multiple balloon assembly, the folding configuration in each figure applies to both single and dual dome configurations of the deployment balloon, with the exception that FIG. 5C, pertains to a folding step unique to dual dome configurations.
Figure 5B:
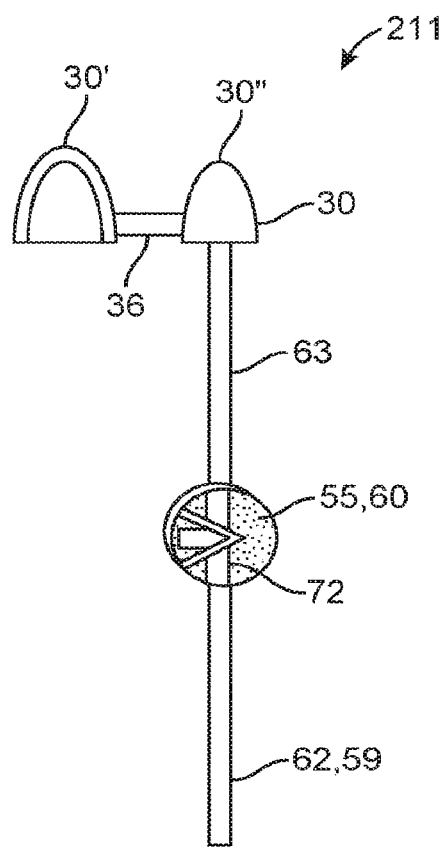
Figure 5C:
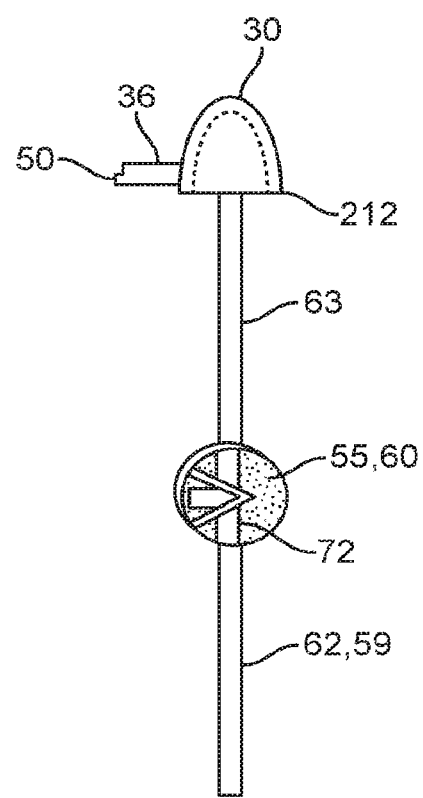
Figure 5D:
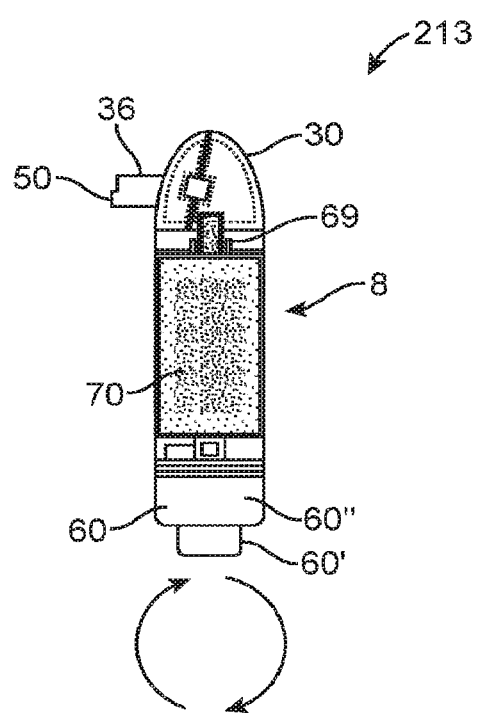
Figure 5E:
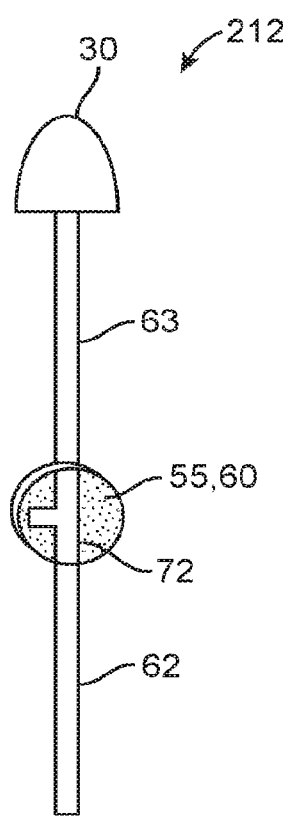
Figure 5F:
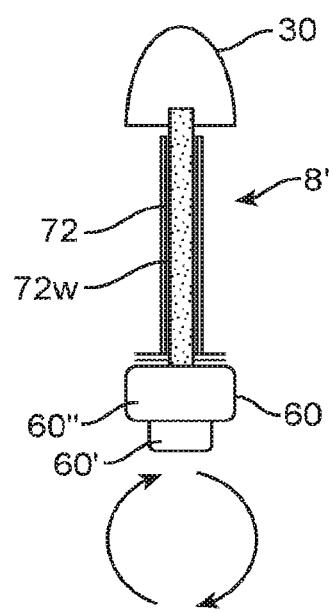
Figure 5G:
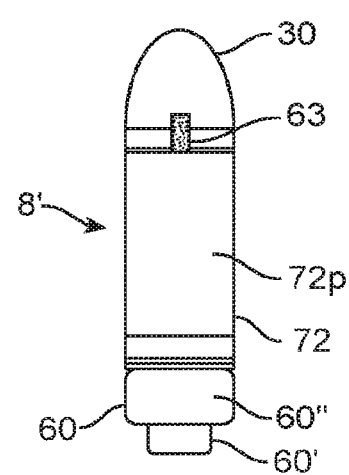

In a specific embodiment, the detachability and retention of tissue penetrating member 40 in the intestinal wall IW can be enhanced by configuring the tissue penetrating member shaft 44 to have an inverse taper 44t as is shown in the embodiment of FIG. 5C. The taper 44t on the shaft 44 is configured such that the application of peristaltic contractile forces from the intestinal wall on the shaft result in the shaft being forced inward 9 (e.g., squeezed inward). This is due to the conversion by shaft taper 44t of the laterally applied peristaltic force PF to an orthogonal force OF acting to force the shaft inward into the intestinal wall. In use, such inverse tapered shaft configurations serve to retain tissue penetrating member 40 within the intestinal wall so as to detach from platform 75 (or other component of delivery mechanism 70) upon deflation of balloon 72. Inverse tapers may also be used for embodiments of tissue penetrating member 40 which have any number of tip shapes 45 in addition to a trocar tip. In additional embodiments, tissue penetrating members 40 having an inverse tapered shaft may also include one or more retaining features 43 to further enhance the retention of the tissue penetrating member within intestinal wall IW once inserted.

As described above, in various embodiments, tissue penetrating member 40 can be fabricated from a number of drugs and other therapeutic agents 101. Also according to one or more embodiments, the tissue penetrating member may be fabricated entirely from drug 101 or may have other constituent components as well, e.g., various pharmaceutical excipients (e.g., binders, preservatives, disintegrants, etc.), polymers conferring desired mechanical properties, etc. Further, in various embodiments one or more tissue penetrating members 40 can carry the same or a different drug 101 (or other therapeutic agent) from other tissue penetrating members. The former configuration allows for the delivery of greater amounts of a particular drug 101, while the later, allows two or more different drugs to be delivered into the intestinal wall at about the same time to facilitate drug treatment regimens requiring substantial concurrent delivery of multiple drugs. In embodiments of device 10, have multiple delivery assemblies 78 (e.g., two, one on each face of balloon 72), a first assembly 78' can carry tissue penetrating members having a first drug 101 and a second assembly 78" can carry tissue penetrating members having a second drug 101.

Figure 8D:
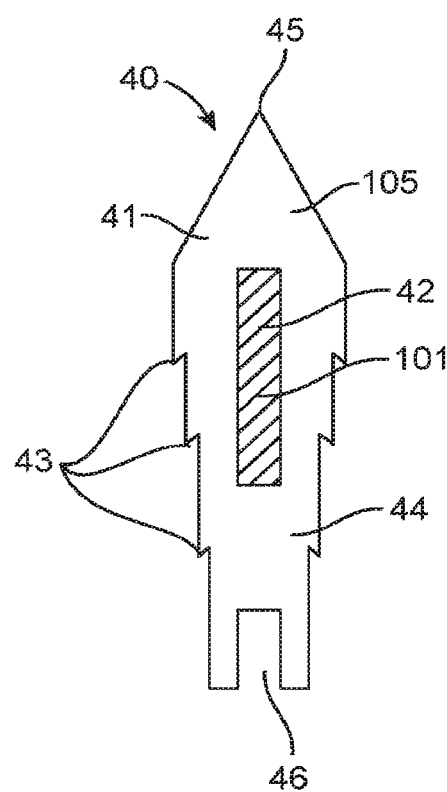
FIG. 8D is a side view of an embodiment of the tissue penetrating member having a separate drug containing section.
Figure 8E:
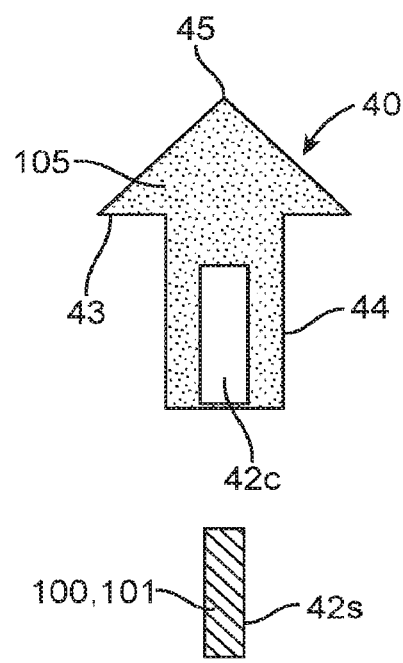
FIGS. 8E and 8F are side views showing assembly of an embodiment of a tissue penetrating member having a shaped drug containing section.
Figure 8F:
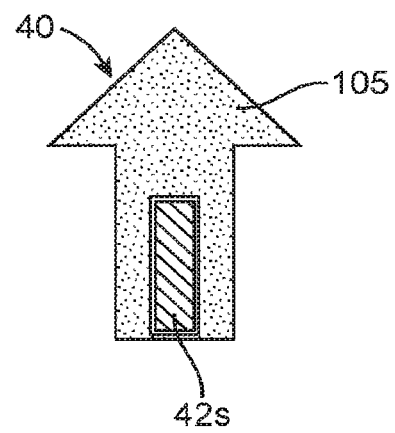

Typically, the drug or other therapeutic agent 101 carried by the tissue penetrating member 40 will be mixed in with a biodegradable material 105 to form tissue penetrating member 40. Material 105 may include one or more biodegradable polymers such as PLGA, cellulose, as well as sugars such as maltose or other biodegradable material described herein or known in the art. In such embodiments, the penetrating member 40 may comprise a substantially heterogeneous mixture of drug 101 and biodegradable material 105. Alternatively, the tissue penetrating member 40 may include a portion 41 formed substantially from biodegradable material 105 and a separate section 42 that is formed from or contains drug 101 as shown in the embodiment of FIG. 8D. In one or more embodiments, section 42 may correspond to a pellet, slug, cylinder or other shaped section 42s of drug 101. Shaped section 42s may be pre-formed as a separate section which is then inserted into a cavity 42c in tissue penetrating member 40 as is shown in the embodiments of FIGS. 8E and 8F. Alternatively section 42s may be formed by adding of drug preparation 100 to cavity 42c. In embodiments, where drug preparation 100 is added to cavity 42c, preparation may be added in as a powder, liquid, or gel which is poured or injected into cavity 42c. Shaped section 42s may be formed of drug 101 by itself or a drug preparation containing drug 101 and one or more binders, preservatives, disintegrates and other excipients. Suitable binders include polyethylene glycol (PEG) and other binders known in the art. In various embodiments, the PEG or other binder may comprise in the range of about 10 to 50% weight percent of the section 42s, with a preferred embodiment of about 30 weight percent. Other binders may include PLGA, Cyclodextrin, Cellulose, Methyl Cellulose, maltose, Dextrin, Sucrose, PGA.

In various embodiments, the weight of tissue penetrating member 40 can range between about 10 to 15 mg, with larger and smaller weights contemplated. For embodiments of tissue penetrating member 40 fabricated from maltose, the weight can range from about 11 to 14 mg. In various embodiments, depending upon the drug 101 and the desired delivered dose, the weight percent of drug in member 40 can range from about 0.1 to about 15%. The weight percent of drug 101 in member 40 can be adjusted depending upon the desired dose as well as to provide for structural and stoichiometric stability to the drug and also to achieve a desired elution profile of the drug. Table 1 lists the dose and weight percent range for a number of drugs which may be delivered by tissue penetrating member 40.

TABLE 1

| Drug | Dose Via Capsule** | % Weight of Drug in the needle |
|---|---|---|
| Insulin | 5-30 units | 2-15% |
| Exenatide | 10 ug | <1% |
| Liraglutide | 0.6 mg | 3-6% |
| Pramlintide | 15-120 ug | 0.1-1% |
| Growth Hormone | 0.2-1 mg | 2-10% |
| Somatostatin and Analogs | 50-600 ug | 0.3-8% |
| GnRH and Analogs | 0.3-1.5 mg | 2-15% |

TABLE 1-continued

| Drug | Dose Via Capsule** | % Weight of Drug in the needle |
|---|---|---|
| Vasopressin | 2-10 units | <1% |
| PTH and Analogues | 20 ug | 1-2% |
| Interferons and analogs | | |
| 1. For Multiple Sclerosis | 0.03-0.25 mg | 0.1-3% |
| 2. For Hep B and Hep C | 6-20 ug | 0.05-0.2% |
| Adalimumab | 2-4 mg/day | 8-12% |
| Infliximab | 5 mg/day | 8-12% |
| Etanercept | 3 mg/day | 8-12% |
| Natalizumab | 3 mg/day | 8-12% |

Tissue penetrating member 40 can be fabricated using one or more polymer and pharmaceutical fabrication techniques known in the art. For example, drug 101 (with or without biodegradable material 105) can be in solid form and then formed into the shape of the tissue penetrating member 40 using molding, compaction or other like method with one or more binding agents added. Alternatively, drug 101 and/or drug preparation 100 may be in solid or liquid form and then added to the biodegradable material 105 in liquid form with the mixture then formed into the penetrating member 40 using molding or other forming method known in the polymer arts.

Desirably, embodiments of the tissue penetrating member 40 comprising a drug or other therapeutic agent 101 and degradable material 105 are formed at temperatures which do not produce any substantial thermal degradation of the drug (or other therapeutic agent) including drugs such as various peptides and proteins. This can be achieved through the use of room-temperature curing polymers and room temperature molding and solvent evaporation techniques known in the art. In particular embodiments, the amount of thermally degraded drug or other therapeutic agent within the tissue penetrating member is desirably less than about 10% by weight and more preferably, less than 5% and still more preferably less than 1%. The thermal degradation temperature(s) for a particular drug are either known or can be determined using methods known in the art and then this temperature can be used to select and adjust the particular polymer processing methods (e.g., molding, curing, solvent evaporation methods etc.) to minimize the temperatures and associated level of drug thermal degradation.

A description will be provided of delivery mechanism 70. Typically, the mechanism will comprise a delivery assembly 78 (containing tissue penetrating members 40) that is attached to delivery balloon 72 as is shown in the embodiment of FIGS. 6A and 6B. Inflation of the delivery balloon provides a mechanical force for engaging delivery assembly 72 outwards from the capsule and into the intestinal wall IW so as to insert tissue penetrating members 40 into the wall. In various embodiments, the delivery balloon 72 can have an elongated shape with two relatively flat faces 72f connected by an articulated accordion-like body 72b. The flat faces 72f can be configured to press against the intestinal wall (IW) upon expansion of the balloon 72 so as to insert the tissue penetrating members (TPMs) 40 into the intestinal wall. TPMs 40 (either by themselves or as part of a delivery assembly 78 described below) can be positioned on one or both faces 72f of balloon 70 to allow insertion of drug containing TPMs 40 on opposite sides of the intestinal wall. The faces 72f of balloon 72 may have sufficient surface area to allow for placement of a number of drug containing TPMs 40 on each face.

Figure 9:
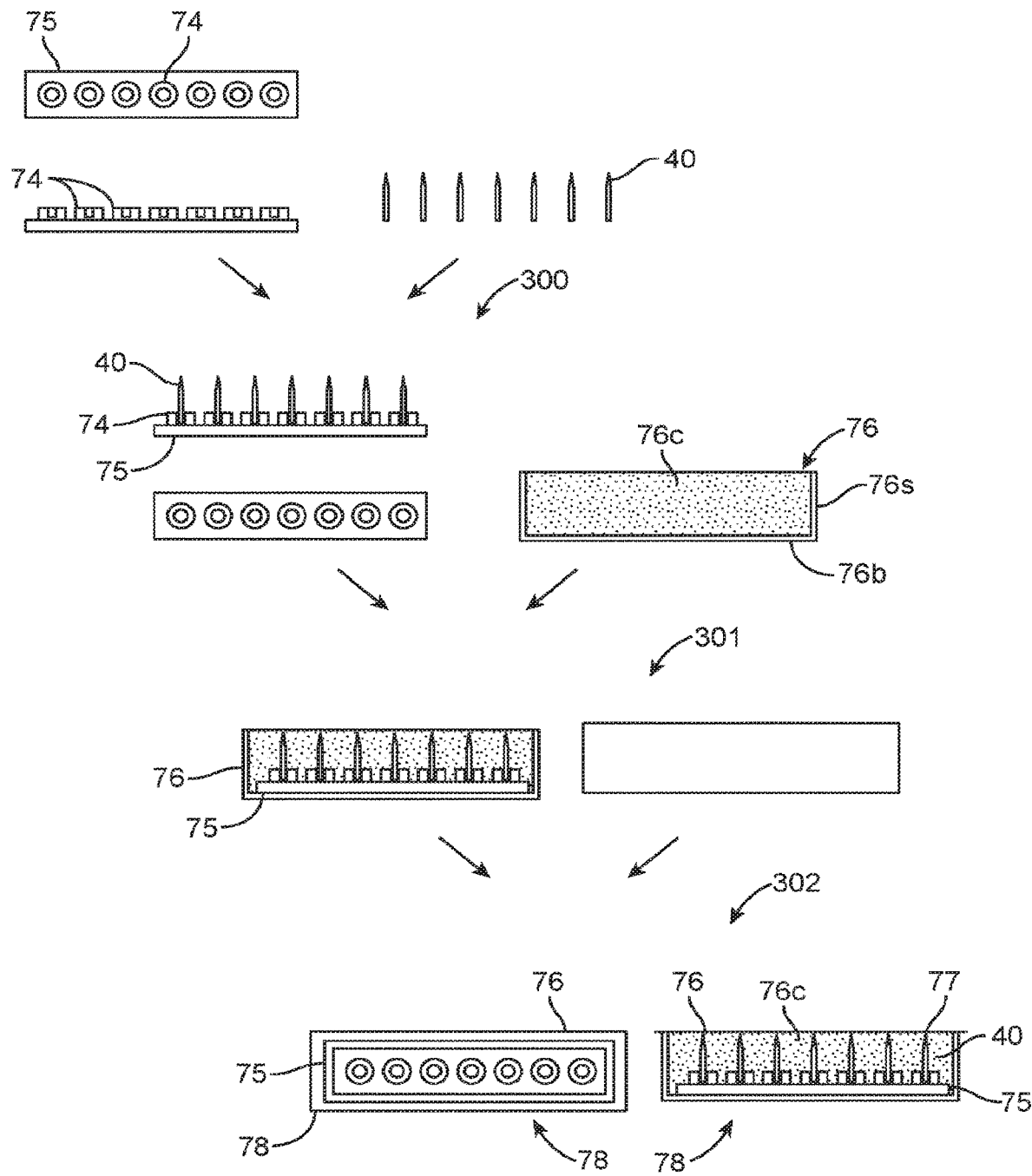
FIG. 9 provides assorted views of the components and steps used to assemble an embodiment of the delivery assembly.

Referring now to FIG. 9, a description will now be provided of assembly of delivery assembly 78. In a first step 300, one or more tissue penetrating members 40 can be detachably coupled to a biodegradable advancement structure 75 which may correspond to a support platform 75 (also known as platform 75). In preferred embodiments, platform 75 includes one or more openings 74 for insertion of members 40 as shown in step 300. Openings 74 are sized to allow for insertion and retention of members 40 in platform 75 prior to expansion of balloon 72 while allowing for their detachment from the platform upon their penetration into the intestinal wall. Support platform 75 can then be positioned within a carrying structure 76 as shown in step 301. Carrying structure 76 may correspond to a well structure 76 having side walls 76s and a bottom wall 76b which define a cavity or opening 76c. Platform 75 is desirably attached to inside surface of bottom wall 76b using adhesive or other joining methods known in the art. Well structure 76 can comprise various polymer materials and may be formed using vacuum forming techniques known in the polymer processing arts. In many embodiments, opening 760 can be covered with a protective film 77 as shown in step 302. Protective film 77 has properties selected to function as a barrier to protect tissue penetrating members 40 from humidity and oxidation while still allowing tissue penetrating members 40 to penetrate the film as is described below. Film 77 can comprise various water and/or oxygen impermeable polymers which are desirably configured to be biodegradable in the small intestine and/or to pass inertly through the digestive tract. It may also have a multi-ply construction with particular layers selected for impermeability to a given substance, e.g., oxygen, water vapor etc. In use, embodiments employing protective film 77 serve to increase the shelf life of therapeutic agent 101 in tissue penetrating members 40, and in turn, the shelf life of device 10. Collectively, support platform 75 attached tissue penetrating members 40, well structure 76, and film 77 can comprise a delivery assembly 78. Delivery assemblies 78 having one or more drugs or therapeutic agents 101 contained within tissue penetrating member 40 or other drug delivery means can be pre-manufactured, stored and subsequently used for the manufacture of device 10 at a later date. The shelf life of assembly 78 can be further enhanced by filling cavity 76c of the sealed assembly 78 with an inert gas such as nitrogen.

Referring back to FIGS. 6A and 6B, assemblies 78 can be positioned on one or both faces 72f of balloon 72. In preferred embodiments, assemblies 78 are positioned on both faces 72f (as shown in FIG. 6A) so as to provide a substantially equal distribution of force to opposite sides of the intestinal wall IW upon expansion of balloon 72. The assemblies 78 may be attached to faces 72f using adhesives or other joining methods known in the polymer arts. Upon expansion of balloon 72, TPMs 40 penetrate through film 77, enter the intestinal wall IW and are retained there by retaining elements 43 and/or other retaining features of tissue penetrating (e.g., an inverse tapered shaft 44t) such that they detach from platform 75 upon deflation of balloon 72.

In various embodiments, one or more of balloons 30, 60 and 72 can be packed inside capsule 20 in a folded, furled or other desired configuration to conserve space within the interior volume 24v of the capsule. Folding can be done using preformed creases or other folding feature or method known in the medical balloon arts. In particular embodiments, balloon 30, 60 and 72 can be folded in selected orientations to achieve one or more of the following: i) conserve space, ii) produce a desired orientation of a particular inflated balloon; and iii) facilitate a desired sequence of balloon inflations. The embodiments shown in FIGS. 5A-5F illustrate an embodiment of a method of folding and various folding arrangements. However, it should be appreciated that this folding arrangement and the resulting balloon orientations are exemplary and others may also be used. In this and related embodiments, folding can be done manually, by automated machine or a combination of both. Also in many embodiments, folding can be facilitated by using a single multi balloon assembly 7 (herein assembly 7) comprising balloons 30, 60, 70; valve chamber 58 and assorted connecting tubings 62 as is shown in the embodiments of FIGS. 3A and 3B. FIG. 3A shows an embodiment of assembly 7 having a single dome construction for balloon 30, while FIG. 3B shows the embodiment of assembly 7 having dual balloon/dome configuration for balloon 30. Assembly 7 can be fabricated using a thin polymer film which is vacuum-formed into the desired shape using various vacuum forming and other related methods known in the polymer processing arts. Suitable polymer films include polyethylene films having a thickness in the range of about 0.003 to about 0.010", with a specific embodiment of 0.005". In preferred embodiments, the assembly is fabricated to have a unitary construction so as to eliminate the need for joining one or more components of the assembly (e.g., balloons 30, 60, etc.). However, it is also contemplated for assembly 7 to be fabricated from multiple portions (e.g., halves), or components (e.g., balloons) which are then joined using various joining methods known in the polymer/medical device arts.

Referring now to FIGS. 5A-5F, 6A-B and 7A-7B, in a first folding step 210, balloon 60 is folded over onto valve fitting 58 with balloon 72 being flipped over to the opposite side of valve fitting 58 in the process (see FIG. 5A). Then in step 211, balloon 72 is folded at a right angle to the folded combination of balloon 60 and valve 58 (see FIG. 5B). Then, in step 212 for dual dome embodiments of balloon 30, the two halves 30' and 30" of balloon 30 are folded onto each other, leaving valve 50 exposed (see FIG. 5C, for single dome embodiments of balloon 30, is folded over onto itself see FIG. 5E). A final folding step 213 can be done whereby folded balloon 30 is folded over 180° to the opposite side of valve fitting 58 and balloon 60 to yield a final folded assembly 8 for dual dome configurations shown in the FIG. 5E and a final folded assembly 8' for single dome configurations shown in FIGS. 5E and 5F. One or more delivery assemblies 78 are then be attached to assembly 8 in step 214 (typically two the faces 72f of balloon 72) to yield a final assembly 9 (shown in the embodiments of FIGS. 6A and 6B) which is then inserted into capsule 20. After an insertion step 215, the final assembled version of device 10 with inserted assembly 9 is shown FIGS. 7A and 7B.

Figure 10A:
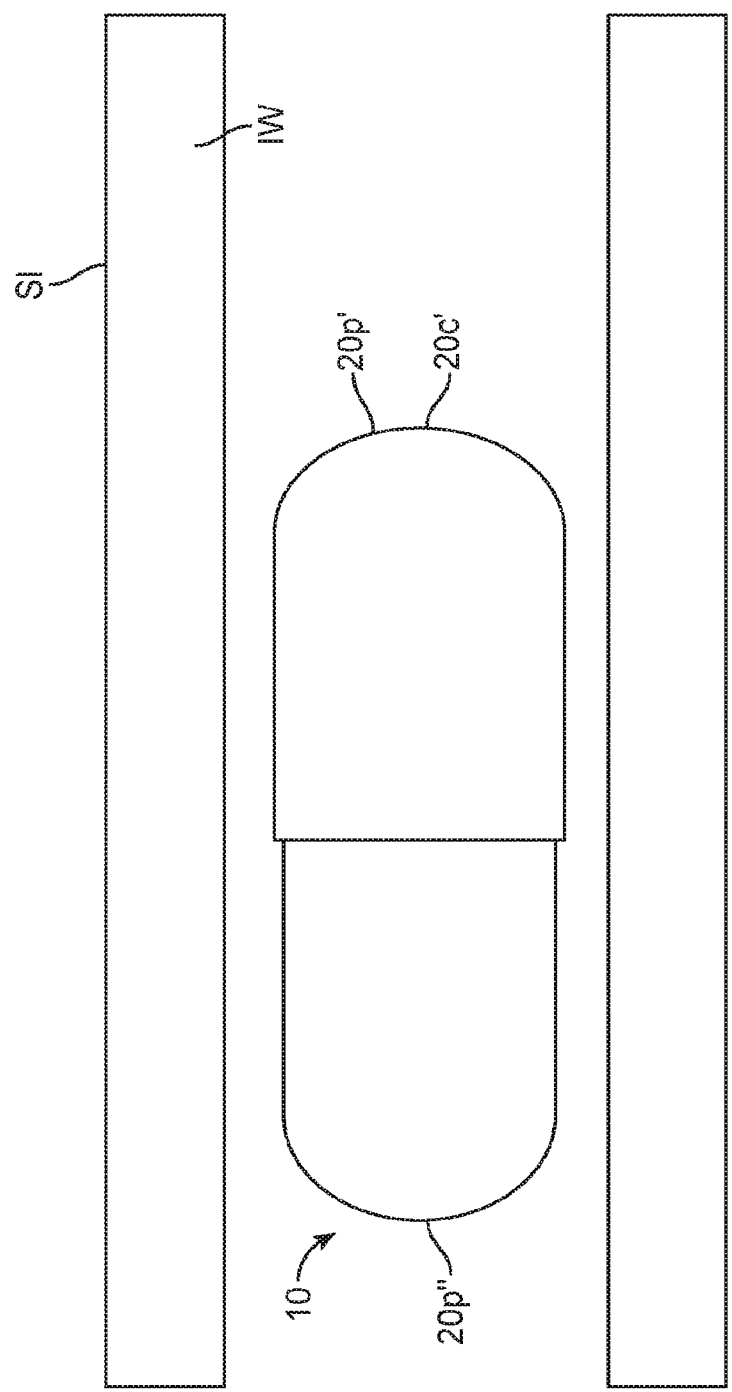
Figure 10C:
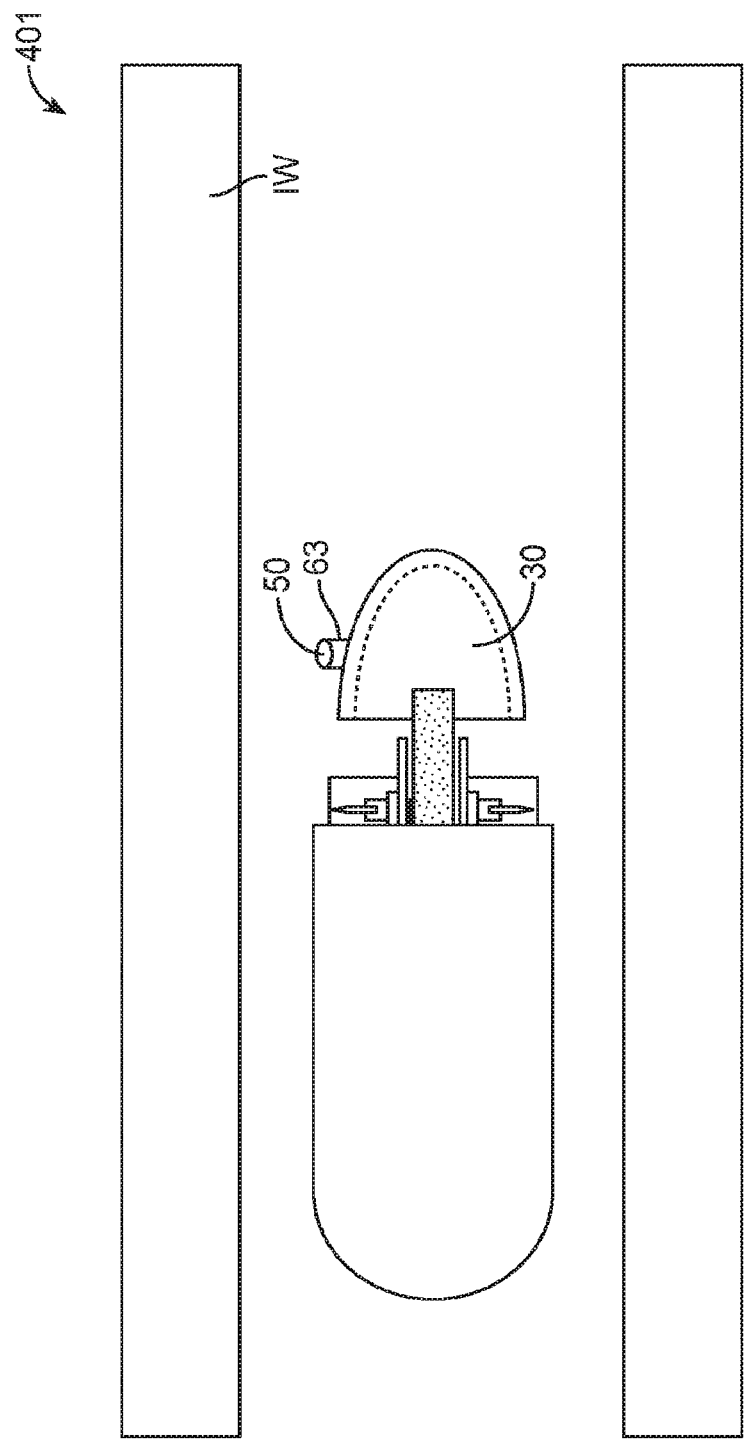
Figure 10D:
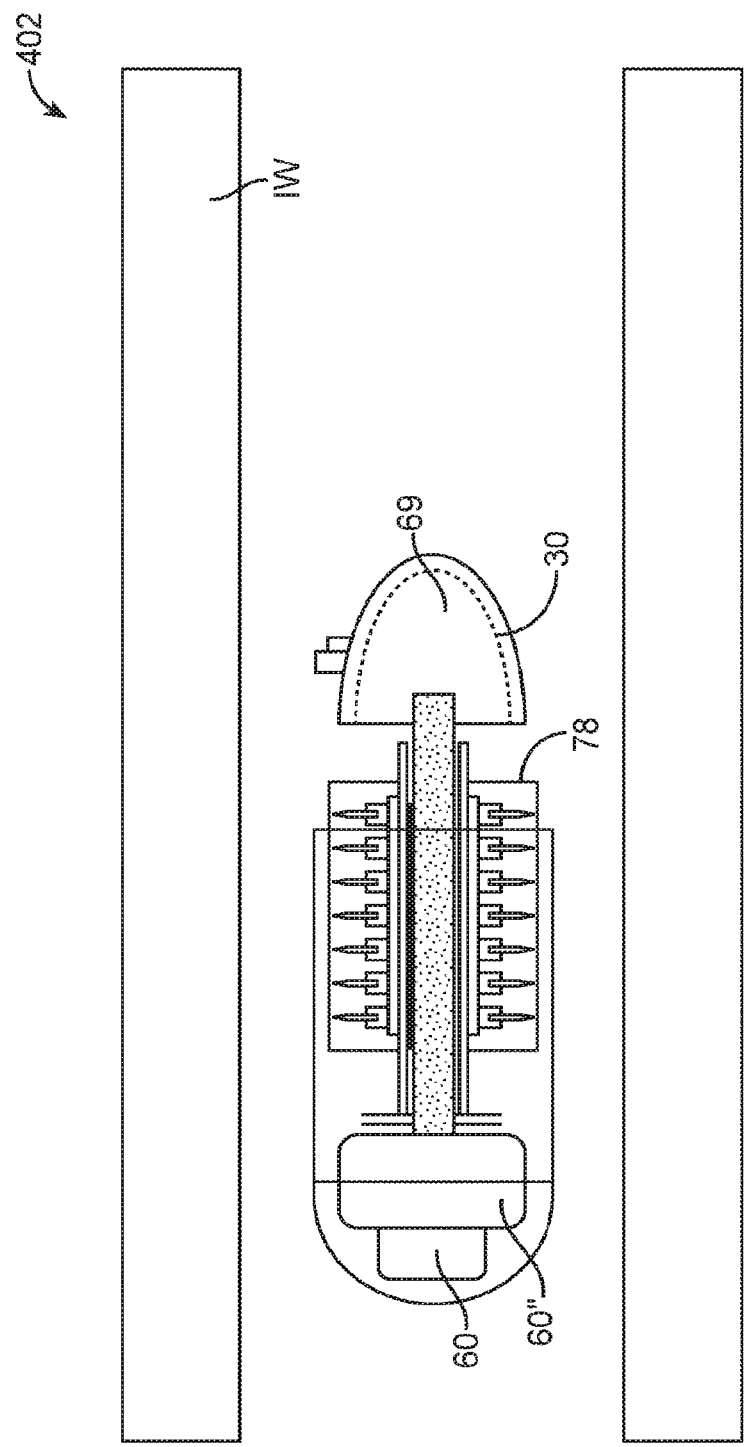
Figure 10F:
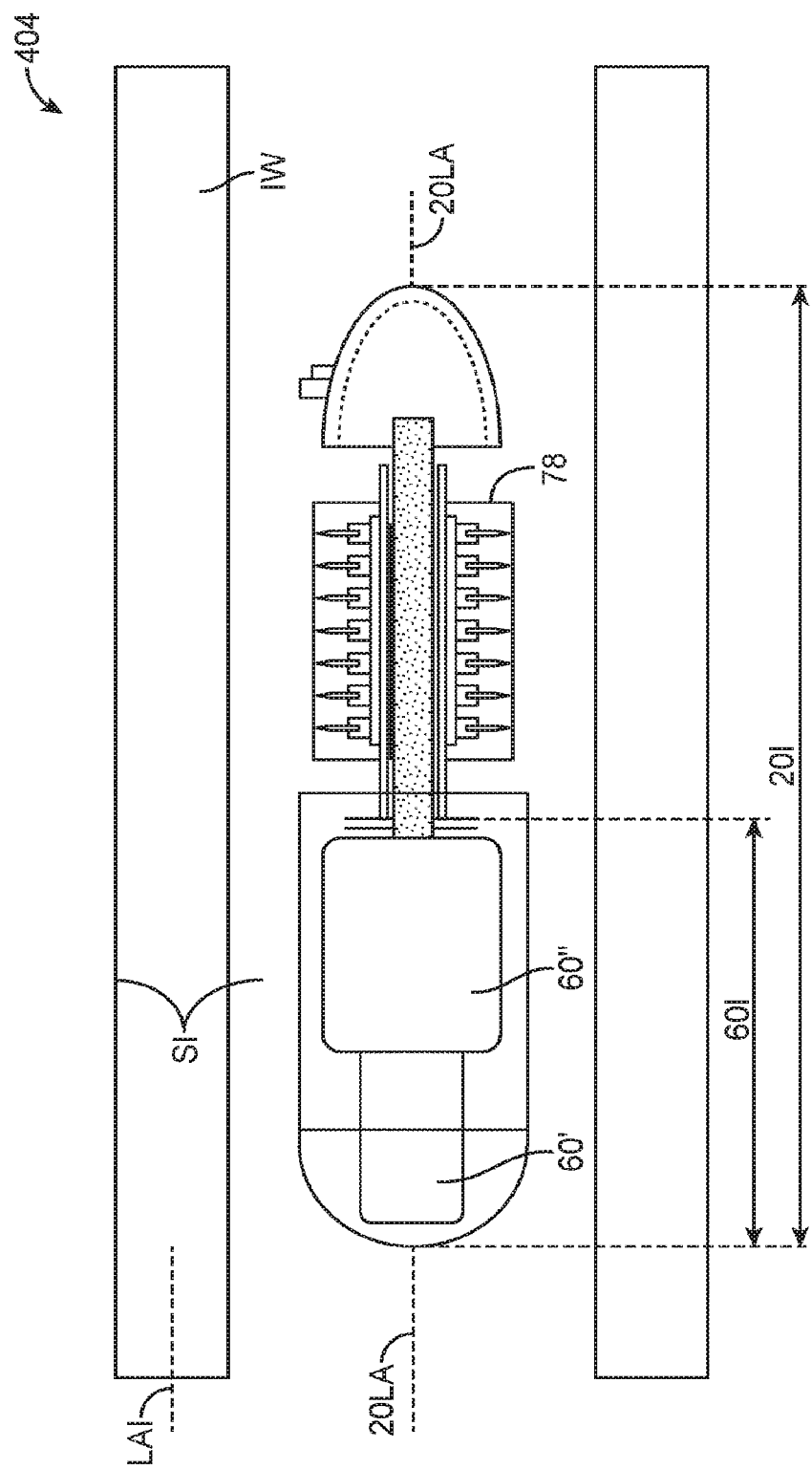
Figure 10G:
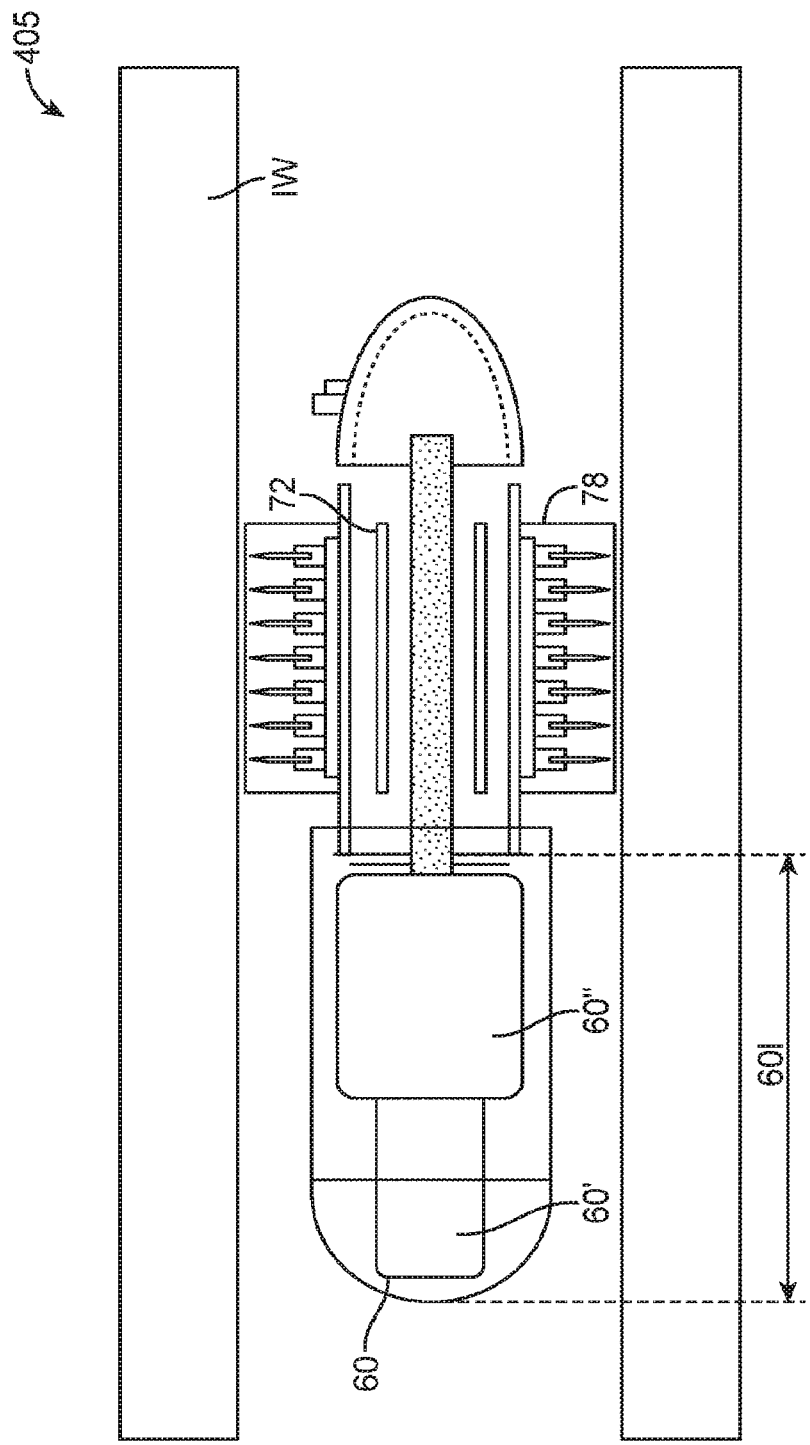
Figure 10H:
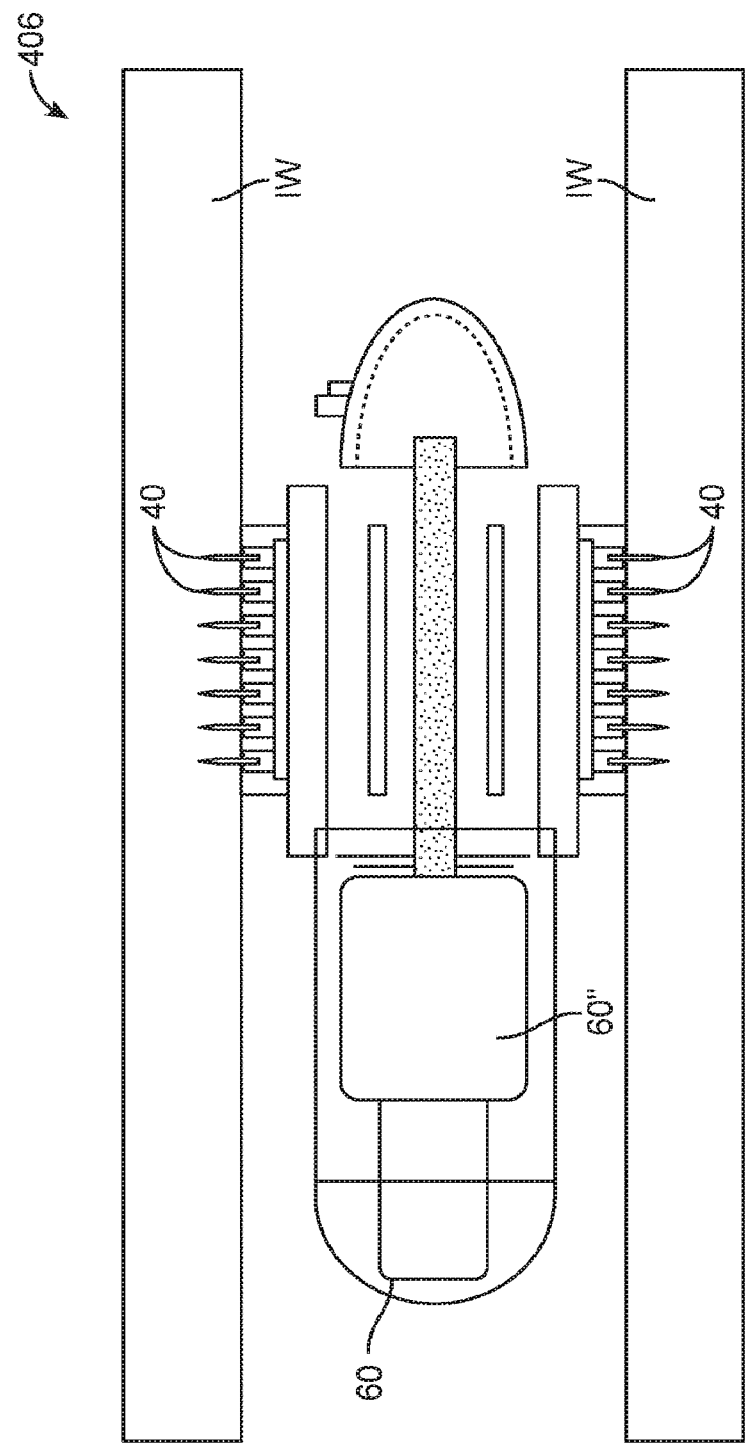
Figure 10I:
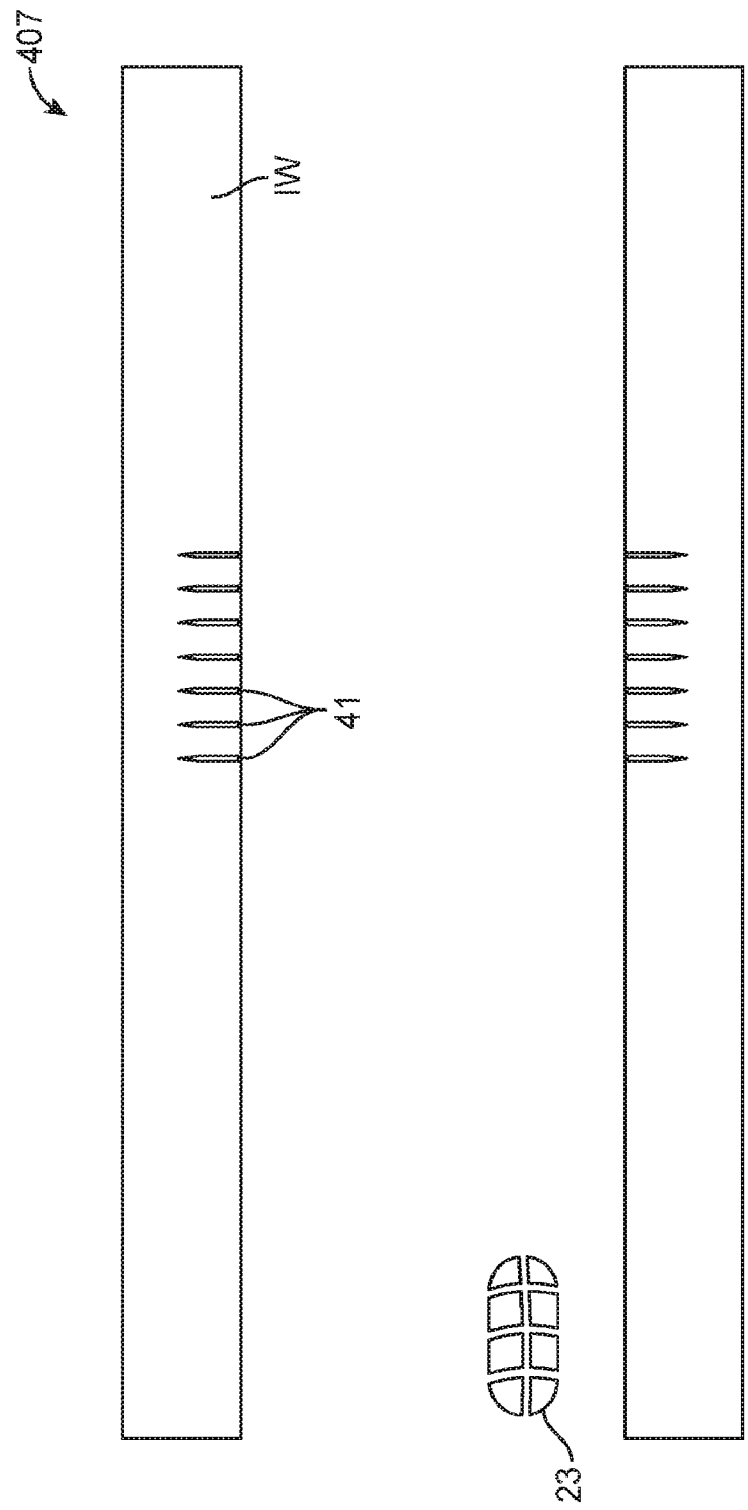

Referring now to FIGS. 10A-10I, a description will be provided of a method of using device 10 to deliver medication 101 to a site in the GI tract such as the wall of the small or large intestine. It should be appreciated that the steps and there order is exemplary and other steps and orders also contemplated. After device 10 enters the small intestine SI, the cap coating 20c' is degraded by the basic pH in the upper small intestine causing degradation of cap 20p' as shown in step 400 in FIG. 10B. Valve 50 is then exposed to fluids in the small intestine causing the valve to begin degrade as is shown in step 401 in FIG. 10C. Then, in step 402, balloon 30 expands (due to generation of gas 69) as shown in FIG. 10D. Then, in step 403, section 60' of balloon 60 begins to expand to start to push assembly 78 out of the capsule body as shown in FIG. 10E. Then, in step 404, sections 60' and 60" of balloon 60 become fully inflated to completely push assembly 78 out of the capsule body extending the capsule length 201 so as to serve to align capsule lateral axis 20AL with the lateral axis of the small intestine LAI as shown in FIG. 10F. During this time, valve 55 is beginning to fail from the increased pressure in balloon 60 (due to the fact that the balloon has fully inflated and there is no other place for gas 69 to go). Then, in step 405, valve 55 has completely opened, inflating balloon 72 which then pushes the now completely exposed assembly 78 (having been pushed completely out of body 20*p*″) radially outward into the intestinal wall IW as shown in FIG. 10G. Then, in step 406, balloon 72 continues to expand to now advance tissue penetrating members into the intestinal wall IW as shown in FIG. 10H. Then, in step 407, balloon 72, (along with balloons 60 and 30) has deflated pulling back and leaving tissue penetrating members retained in the intestinal wall IW. Also, the body portion 20*p*″ of the capsule has completely degraded (due to degradation of coating 20*c*″) along with other biodegradable portions of device 10. Any portion not degraded is carried distally through the small intestine by peristaltic contraction from digestion and is ultimately excreted.

Referring back to FIG. 1B, as an alternative or supplement to the use of pH sensitive degradable coatings and valves for inflation of one or more of balloons 30, 60, and 72 (and deployment of medication 100), in various embodiments the balloons can be expanded responsive to a sensor 97, such as a pH sensor 98 or other chemical sensor which detects the presence of the capsule in the small intestine. Sensor 97 can then send a signal to a controllable embodiment of isolation valve 50 or to an electronic controller 29*c* coupled to a controllable isolation valve 50 to open and thus expand balloon 30 as is described herein. Embodiments of a pH sensor 98 can comprise an electrode-based sensor or it can be a mechanically-based sensor such as a polymer which shrinks or expands upon exposure to a selected pH or other chemical conditions in the small intestine. In related embodiments, an expandable/contractible pH sensor 98 can also comprise the isolation valve 50 itself, by configuring the sensor to expand or contract about connector 63 and/or 36 so as to open a channel between balloons 30 and 60 and/or compartments 34 and 35.

According to another embodiment for detecting when device 10 is in the small intestine (or other location in the GI tract), sensor 97 can comprise pressure/force sensor such as strain gauge for detecting the number of peristaltic contractions that capsule 20 is being subject to within a particular location in the intestinal tract (in such embodiments capsule 20 is desirably sized to be gripped by the small intestine during a peristaltic contraction). Different locations within the GI tract have different number of peristaltic contractions. For example, the small intestine has between 12 to 9 contractions per minute with the frequency decreasing down the length of the intestine. Thus, according to one or more embodiments, detection of the number of peristaltic contractions can be used to not only determine if capsule 20 is in the small intestine, but the relative location within the intestine as well. In use, these and related embodiments allow for release of medication 100 at a particular location in the small intestine.

Still referring to FIG. 1B, as an alternative or supplement to internal activation of drug delivery by device 10 (e.g., using a pH sensitive coatings and/or sensor), in some embodiments, the user may externally send a signal to expand one or more of balloon 30, 60 and 72 to deliver medication 100 to the intestinal wall. The signal may be sent by means of RF, magnetic or other wireless signaling means known in the art. In various embodiments, external activation can be achieved by use of a controllable isolation valve 50 for example, an RF controlled miniature solenoid valve or other electro-mechanical control valve (not shown). In other embodiments, a controllable isolation valve 50 may correspond to a miniature magnetically valve such as a magnetically controlled miniature reed switch (not shown). Such electromechanical or magnetic-based valves can be fabricated using mems and other micro manufacturing methods. In these and related embodiments, the user can use a handheld communication device 13 (e.g., a hand held RF device such as a cell phone) as is shown in the embodiment of FIG. 1B, to send a receive signals 17 from device 10. In such embodiments, swallow able device may include a transmitter 28 such as an RF transceiver chip or other like communication device/circuitry. Handheld device 13 may not only includes signaling means, but also means for informing the user when device 10 is in the small intestine or other location in the GI tract. The later embodiment can be implemented through the use of logic resources 29 (e.g., a processor 29) coupled to transmitter 28 to signal to detect and singe to the user when the device is in the small intestine or other location (e.g., by signaling an input from the sensor). Logic resources 29 may include a controller 29*c* (either in hardware or software) to control one or more aspects of the process. The same handheld device can also be configured to alert the user when balloon 30 (as well as balloons 52 and 60) has been expanded and the selected medication 100 delivered (e.g., using processor 29 and transmitter 28). In this way, the user is provided confirmation that medication 100 has been delivered. This allows the user to take other appropriate drugs/therapeutic agents as well as make other related decisions (e.g., for diabetics to eat a meal or not and what foods should be eaten). The handheld device can also be configured to send a signal to swallowable device 10 to over-ride isolation valve 50 and so prevent, delay or accelerate the delivery of medication 100. In use, such embodiments allow the user to intervene to prevent, delay or accelerate the delivery of medication, based upon other symptoms and/or patient actions (e.g., eating a meal, deciding to go to sleep, exercise etc.). The user may also externally expand balloon 30 or expandable member 30 at a selected time period after swallowing the capsule. The time period can be correlated to a typical transit time or range of transit times for food moving through the user's GI tract to a particular location in the tract such as the small intestine.

Figure 11A:
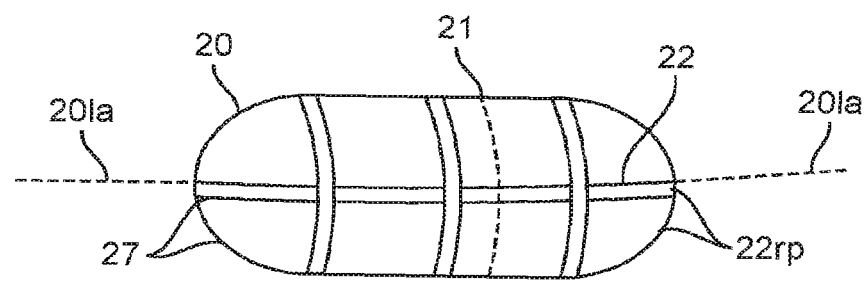
FIG. 11A shows an embodiment of a swallowable drug delivery device including a capsule having bio-degradable seams positioned to produce controlled degradation of the capsule in the GI tract.
Figure 11B:
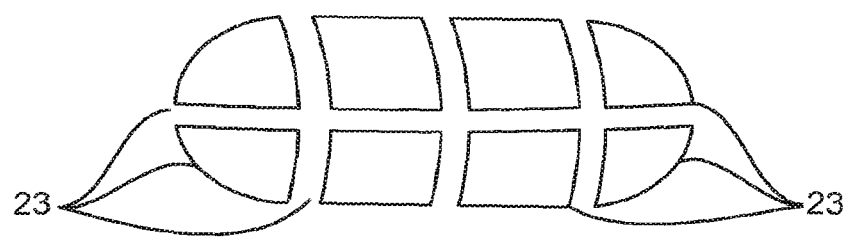
FIG. 11B shows the embodiment of FIG. 11A after having been degraded in the GI tract into smaller pieces.
Figure 16:
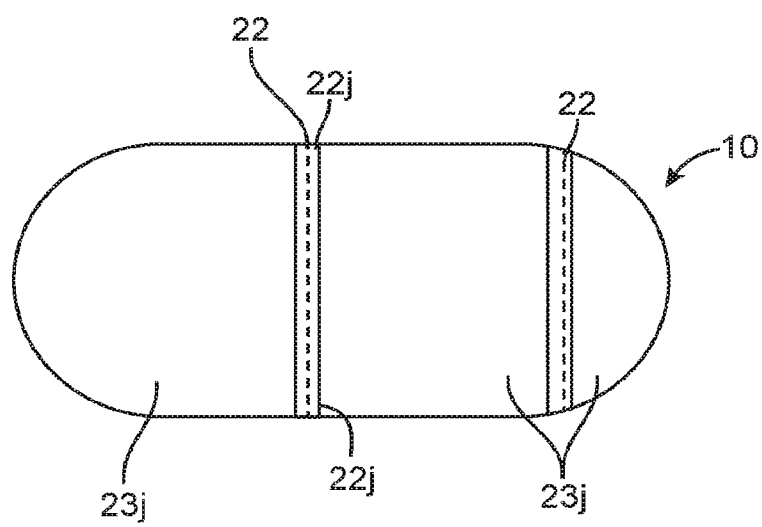
FIG. 16 shows an embodiment of a balloon tearable capsule fabricated from separate portions joined by seams, which can be torn by inflation of the expandable balloon.

Referring now to FIGS. 11A-11B and 16, in various embodiments, the capsule 20 can include seams 22 comprising biodegradable material which controllably degrade to produce capsule pieces 23 of a selectable size and shape to facilitate passage through the GI tract as is shown in the embodiment of FIGS. 11A and 11B. Seams 22 can also include pores or other openings 22*p* for ingress of fluids into the seam to accelerate biodegradation as is shown in the embodiment of FIG. 16. Other means for accelerating biodegradation of seams 22 can include pre-stressing the seam and/or including perforations 22*f* in the seam as is also shown in the embodiment of FIG. 16.

Figure 12A:
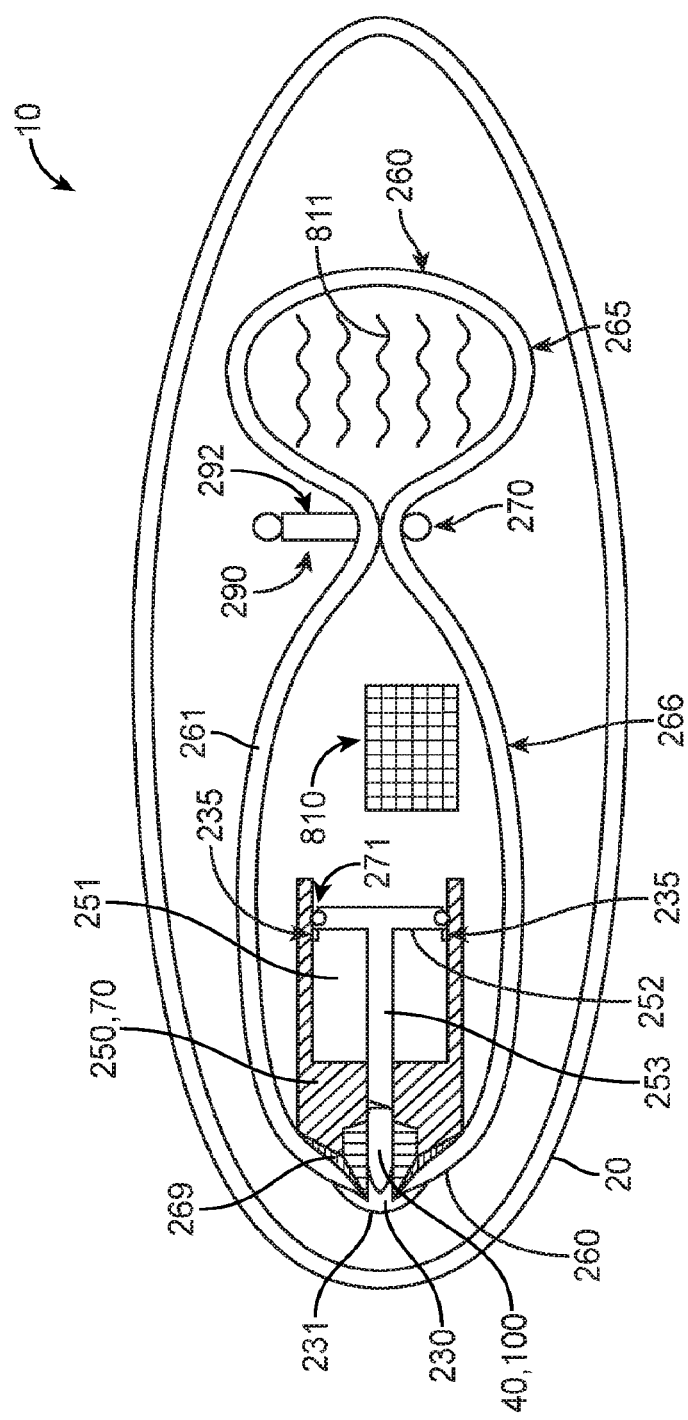
FIG. 12A-B show an embodiment of a capsule having a piston-cylinder assembly.
Figure 12B:
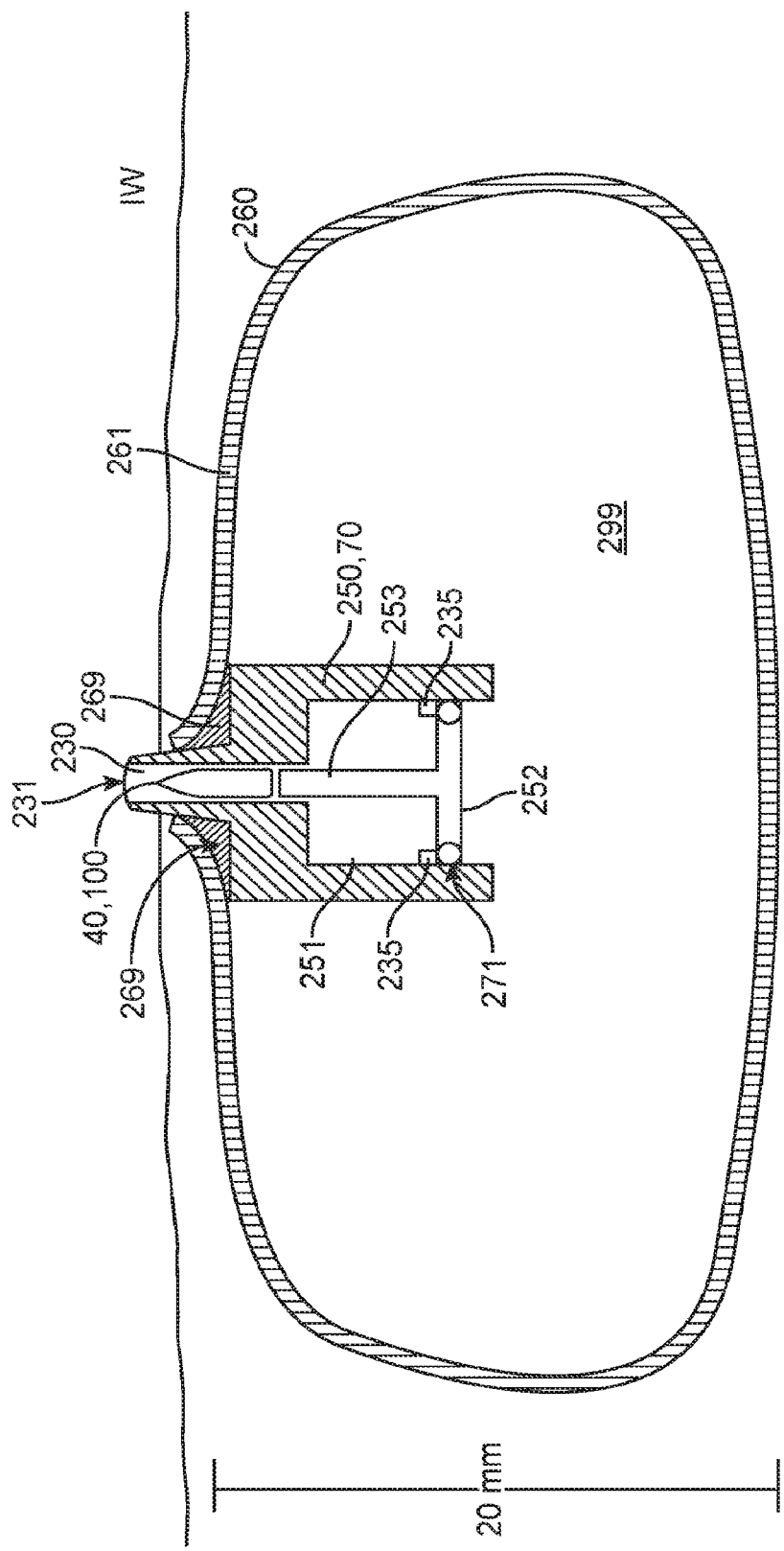
Figure 12C:
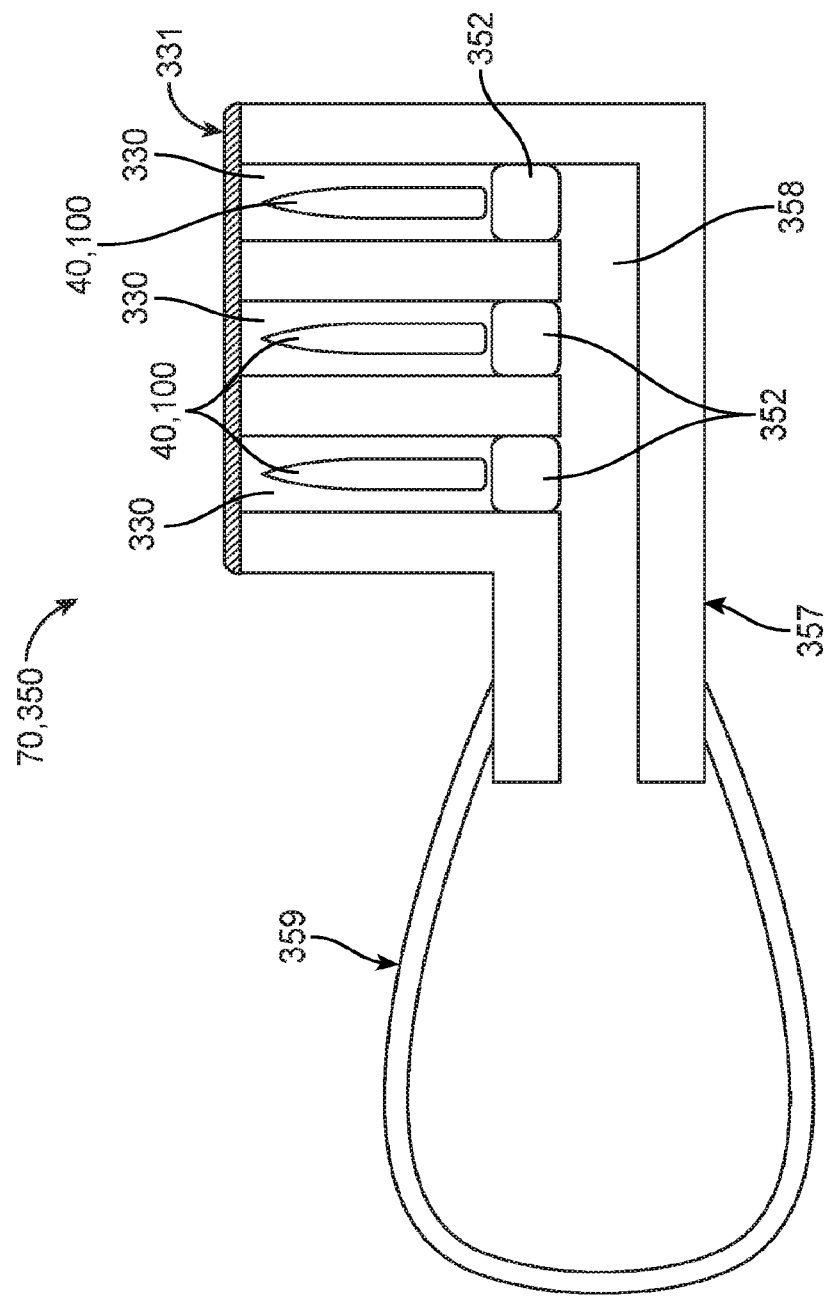
FIG. 12C shows an embodiment of a delivery mechanism having an array of piston-cylinder assemblies.

Referring now to FIGS. 12A-12C, in other embodiments of a swallow able drug delivery device 10, the device 10 may include one or more piston cylinder assemblies (PCA) 250 for delivering one or more needles or other tissue penetrating members (TPM) 40 into the intestinal wall. As such, in these and related embodiments, the piston cylinder assembly (PCA) comprises the delivery mechanism 70. Typically, the piston cylinder assembly (PCA) 250 will be positioned substantially inside a balloon such as balloon 260. However, they may be positioned partially or even completely outside of balloon 260 or other balloon described herein. In some embodiments the balloon 260 comprises multiple portions. As shown in FIG. 12A, the balloon 260 comprises two portions, the first portion comprises a first compartment 265 and the second portion comprises a second compartment 266 separated by a release valve assembly 290. One portion contains a solid reactant 810 such as potassium bicarbonate and the other portions contains a liquid reactant 811 such as citric acid which reacts with the solid reactant to produce a gas 299 such as $CO_2$. The valve assembly 290 comprises an O-ring 270 positioned over a dissolvable pinch valve 292 which pinches down and maintains a seal between the two portions 265 and 266 of the balloon 260. The dissolvable valve is fabricated from maltose or other material which dissolves upon contact with fluid in the small intestine. When that happens, fluid from one portion of the balloon mixes with the reactant in the other to generate the gas 299 to inflate the balloon 260.

Typically, the PCA 250 is positioned in the portion/compartment of the balloon 260 containing the solid reactants (second compartment 266) and is dimensioned accordingly. In one more dimensional embodiments, the balloon can have a vertical height between about 12 to 16 mm, with a preferred embodiment of 14 mm, while the inner diameter of the balloon 260 can be in the range of 18 to 22 mm with preferred embodiment of 20 mm. Other dimensions are also contemplated. In various embodiments, all or portion of the PCA 250 is fabricated from materials which can dissolvable materials such maltose, or methyl cellulose. It can also be fabricated from ABS and other polymers which are inert within the GI tract. In specific embodiments, the outer top portion of the piston can be made of silicone which is mounted on an inner structure, such as a pedestal structure which can be made of ABS.

As shown in FIG. 12A, when uninflated, the PCA 250 is positioned sideways (horizontally) within the balloon 260 (with respect to the lengthwise axis of the balloon), but when the balloon 260 is inflated the PCA 250 re-orients itself to a vertical position as shown in FIG. 12B. This reorientation can be achieved by virtue of conformation/shape changes once the balloon 260 is inflated as well as by means of an adhesive or other joint 269 attached the PCA 250 to the balloon wall 261 which can be configured to exert a force on the PCA 250 to bias it into a vertical orientation (i.e., the joint is made when the PCA 250 is in a vertical position and then the PCA is put into a horizontal position). The joint 269 may comprise various elastic materials known in the art including silicone. The PCA comprises a piston 252 and piston rod 253 which are positioned inside a cylinder 251 (aka piston cylinder). The needle or TPM 40 sits above the piston rod 253 within a needle lumen 230, which is continuous with the piston cylinder. The needle lumen can also include a covering 231 (herein needle lumen covering) which can comprise a foil or polymer film. The ratio in diameter between the piston and piston rod can be selected to result in desired pressure concentration effect (e.g., 2:1, 3:1, etc.) from the decrease in surface area. An O-ring 271 is positioned between the piston 252 and the piston cylinder 251 to maintain a seal between the piston 252 and the wall of the piston cylinder 251. Also, a pressure sensitive release 235 is positioned inside the cylinder 251 to keep the piston 252 in place until a desired pressure (also referred to as a pressure threshold) has built up (e.g., 5 to psi 20 psi, more preferably 8 to 10 psi) inside balloon 260. The release 235 may correspond to a tab, latch or an O-ring. In use, this release serves to assure that there is sufficient pressure within the balloon to drive the needle 40 a desired depth into the wall of the small intestine (IW).

When the valve separating the two portions (265 and 266) of the balloon 260 dissolves and the balloon begins to inflate, the PCA 250 re-orients itself from a horizontal to vertical orientation as described above. Then, when the pressure in the balloon 260 exceeds the release pressure of the release tab, the piston rod advances against the needle (or other TPM) to force the needle 40 out of the needle lumen 230 and into the wall of the small intestine. Once the needle passes through the needle lumen into the intestinal wall, the balloon 260 then deflates via the now open needle lumen. After needle deployment, the PCA 250 either dissolves or passes harmlessly through the GI tract.

In one or more embodiments, the delivery mechanism 70 can comprise an array 350 of the PCAs (multiple needle PCA) that can be configured for the delivery of multiple needles 40 (or other TPM) as shown in FIG. 12C. In these and related embodiments, the PCAs can include a common inflation manifold 357 coupled to multiple needle lumens 330 via central lumen 358 at one end and to the balloon 359 at the other. Various embodiments of a multiple needle PCA 350 can be configured to deliver from 2 to 6 needles or more. Each needle may contain the same or different drug or other therapeutic agent.

Figure 12D:
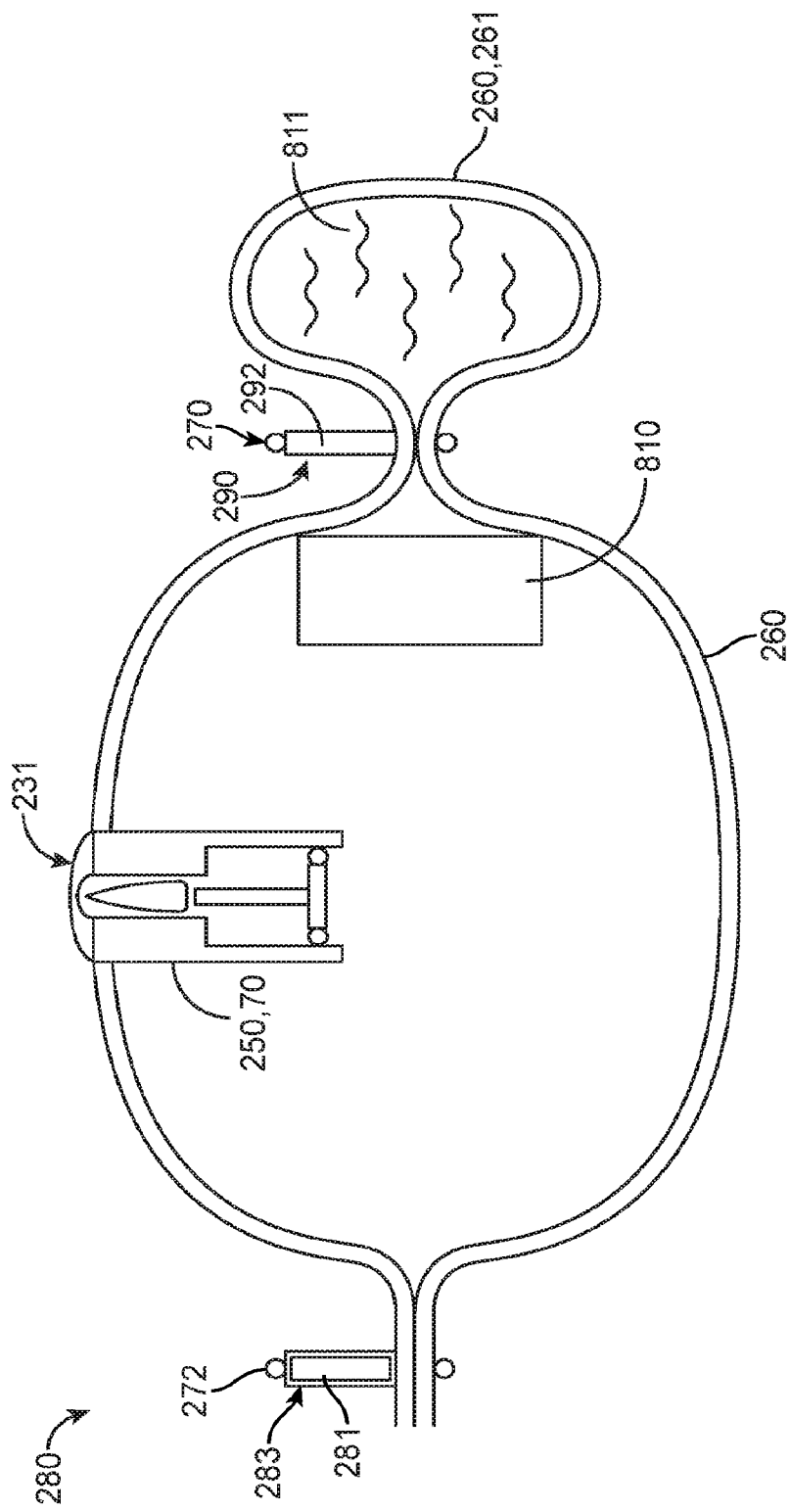
FIG. 12D shows an embodiment of a capsule having a piston-cylinder assembly and a deflation valve.

As described above, deflation of the delivery balloon 260 occurs through the needle lumen once the needle has been delivered into tissue with no additional means for balloon deflation needed. Referring now to FIG. 12D, in alternative embodiments, the delivery balloon 260 may also include a separate deflation valve assembly 280 which serves as backup or secondary means for deflation in addition to the needle lumen 230. As shown in FIG. 12D, the deflation valve assembly comprises an O-ring 272 positioned over a dissolvable pinch valve 281 which pinches down an open end of the delivery balloon 260. The valve includes a dis solvable body portion made of maltose or other similar material as the release valve and an outer coating such as methyl cellulose. The outer coating 283 is configured to take a substantially longer time to dissolve than the dissolvable valve in the release valve assembly such that the deflation valve is not actuated for periods of 10 minutes or longer (preferably 20) after the release valve is actuated. This is to assure that deflation valve is not actuated until well after the needle has been advanced into the intestinal wall.

Figure 13A:
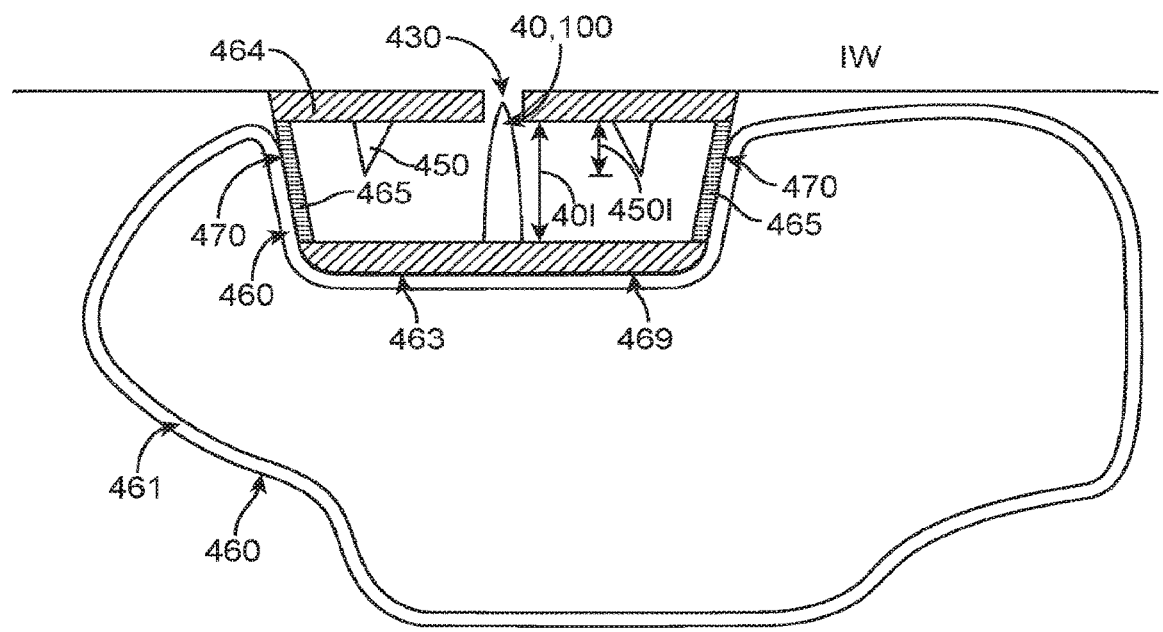
FIG. 13A shows an embodiment of a delivery mechanism having delivery balloon and a delivery compartment.
Figure 13B:
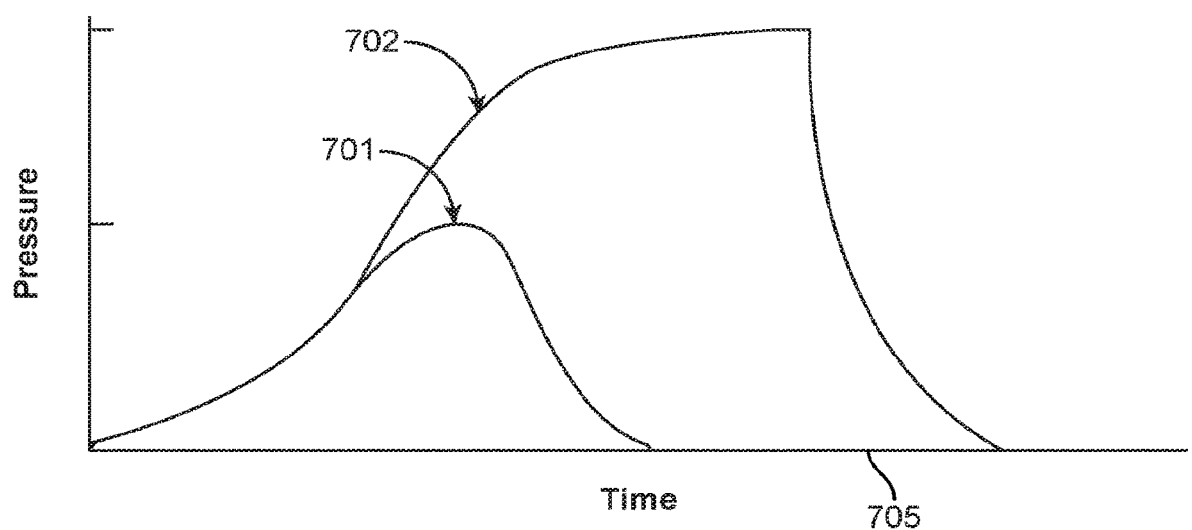
FIG. 13B depicts a balloon inflation pressure curve including a puncture pressure at which the puncture needles puncture the balloon.
Figure 14:
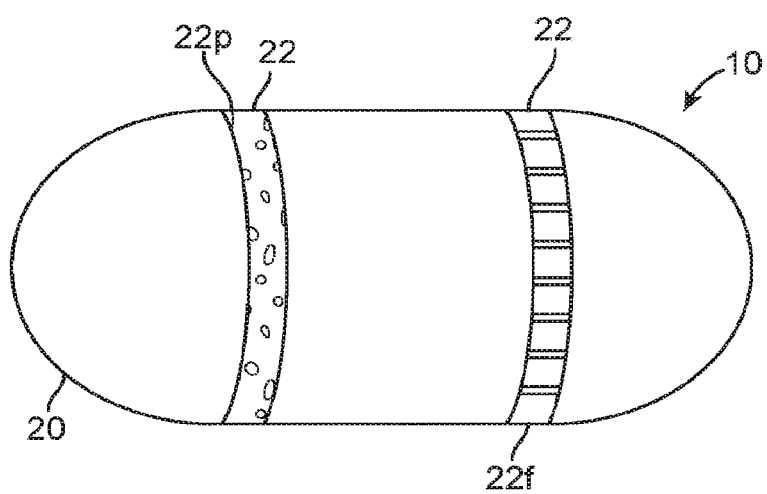
FIG. 14 shows an embodiment of a capsule having biodegradable seams including pores and/or perforations to accelerate biodegradation of the capsule.

Referring now to FIG. 13A-13B, in one or more embodiments of the swallowable device, the delivery balloon 460 can include an assembly configured to both control pressure at which the needle is advanced out of the balloon and into the intestinal wall as well as ass sure that balloon deflates by means of puncture. The assembly can include a lower portion 463 to which one or more TPMs (herein also referred to as drug needle) 40 are attached and an upper portion 464 to which one or more puncture needles (puncture members) 450 are attached. The upper portion may include an aperture 430 or opening for the drug needle to be advanced out of the assembly and into the intestinal wall. Upper portion 464 and lower portion 463 may be joined by sidewalls 465. Sidewalls 465 may be collapsible to permit portions 464 and 463 to come together. Sidewalls 465 may have enough rigidity to keep the upper portion 464 and lower 463 apart while balloon 460 is not inflating. Sidewalls 465 collapse, collapse however under the balloon pressure. The sidewalls may be weakly bonded to the balloon 460 with weak adhesive 470 such that the sidewalls conform to the balloon until the balloon 460 inflates. Upon inflation of balloon 460, the sidewalls 465 separate from the balloon 460. Lower portion 463 may also be bonded to the balloon, but with stronger adhesive 469 The entire assembly is positioned between the balloon and the intestinal wall IW as shown in in FIG. 13A.

Upon inflation of the delivery balloon 460, the puncture needles 450 are configured to penetrate and puncture the lower portion 463 of the delivery assembly and the delivery balloon 460 in order to rupture the delivery balloon. Preferably, the drug needles 40 have a length 401 sufficiently longer than the length of the puncture needles 4501 such that the drug needle(s) 40 is already on its way out of the assembly and even into the intestinal wall before the puncture needles 450 make contact with the lower portion 463 and the balloon 460. According to one or more embodiments, the drug needle is between 25 to 300% longer than puncture needles with specific embodiments of 50, 75, 100, 150, 200 and 250%.

According to one or more embodiments, the lower portion 463 is fabricated from a material which does not allow the puncture needle to penetrate until a desired pressure is reached (e.g., 4 to 20 psi, more preferably 8 to 12 psi). This in turn keeps the drug needle from being completely advanced out into the intestinal wall until that desired pressure is reached. Once the puncture needles 450 penetrate the lower portion 463, they allow the drug needle 40 to be completely advanced out, while simultaneously puncturing the inflated balloon 460 to ensure deflation. These and related embodiments provide the benefit of both controlling the pressure at which the drug needle 40 is assuring that the balloon is deflated.

FIG. 13B shows the Balloon Inflation Pressure (BIP) 702 and the puncture needle pressure (PNP) 701, the pressure used to advance the puncture needles to penetrate balloon 460 and lower portion 463, as time progresses. The PNP rises and peaks as the puncture needles begin to penetrate the lower portion 463. Once penetration of the lower portion 463 and balloon 460 is complete PNP drops to zero. After the drug needle 40 has been fully inserted into the intestinal wall the gas inside the balloon 460 is able to escape out of aperture 430 and BIP drops to zero as the balloon 460 deflates. In various embodiments, the entire assembly can be fabricated from various biodegradable or inert polymers know in the art. The pressure at which the lower portion 463 is penetrated can be controlled by one or more of the thickness and materials for the lower portion 463. In various embodiments, the lower portion 463 can be fabricated from a polymer film including various inert (acrylonitrile butadiene styrene (ABS)) and/or biodegradable polymers films known in the art (e.g., methylcellulose).

According to one or more embodiments, the drug needle or other tissue penetrating member 40 can be fabricated from methyl cellulose polymers. Such methyl cellulose polymers can include hydroxy methyl cellulose, carboxy methyl cellulose and various polymer thereof. The advantages of the use of such methyl cellulose polymers for fabrication of the drug needle (or other tissue penetrating member) compared to maltose based drug needles include little or no sensitivity to humidity during storage, reduced wall thickness, smaller needle size with the same drug payload, and ability to process the needle after fabrication including processing such as grinding, sharpening, sanding and other related processes. In one or more embodiments, a methyl cellulose based drug needle may have a wall thickness in the range of 0.05 to 0.15 mms with a specific embodiment of 0.1 mms. Also in one more embodiments, the methyl cellulose based drug needle may carry between 25-150% more drug versus a same sized maltose-based drug needle. In a specific embodiment of a drug needle having an outer diameter of 1.5 mm, the methyl cellulose needle can carry 100% more drug versus a maltose-based needle.

Figure 15:
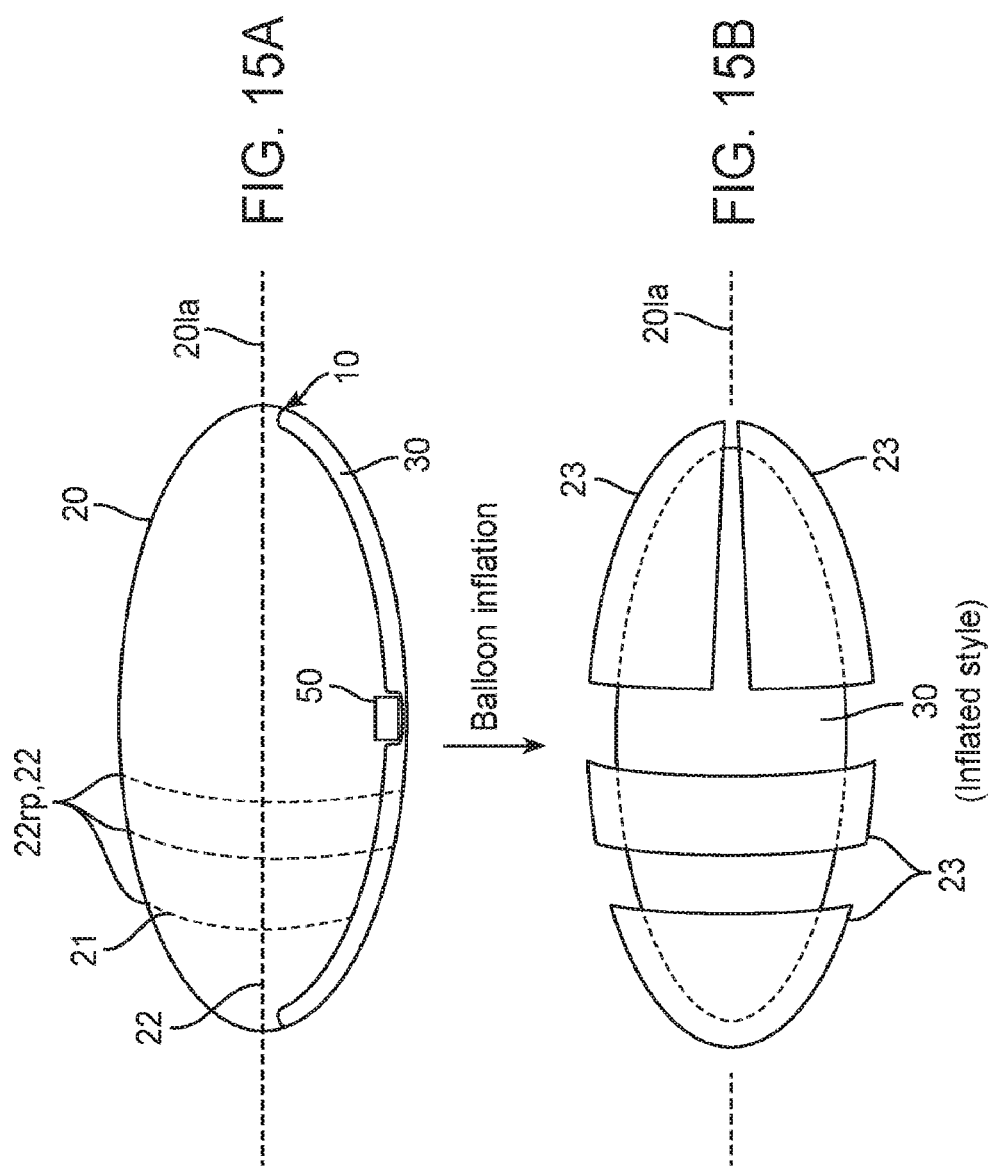
FIGS. 15A-15B show an embodiment of a capsule having tearable seams arranged in a radial or lateral pattern for tearing of the capsule by inflation of the expandable balloon.

Referring now to FIGS. 15A-15B and 16, in many embodiments seams 22 can also be configured and arranged so as to allow capsule 20 to be broken into smaller pieces by the inflation of balloon 30 or other expandable member 30. In particular embodiments, seams 22 can be oriented with respect to capsule radial perimeter 21, including having a radial pattern 22rp so as to have the capsule break into halves or other fractional pieces along its perimeter. Seams 22 may also be longitudinally-oriented with respect to capsule lateral access 201a to have the capsule break up into lengthwise pieces.

As an alternative or additional approach for breaking up capsule 20 by balloon inflation (or expansion of other expandable member 30), capsule 20 can be fabricated from two or more separate joinable pieces 23j (e.g., radial halves) that are joined at a joint 22j formed by seams 22 (which function as an adhesive joint) as shown in the embodiment of FIG. 16. Alternatively, joinable pieces 23j may be merely joined by a mechanical fit such as a snap or press fit.

Suitable materials for seams 22 can include one or more biodegradable materials described herein such as PLGA, glycolic acid etc. Seams 22 can be attached to capsule 20 using various joining methods known in the polymer arts such as molding, hot melt junctions, etc. Additionally for embodiments of capsule 20 which are also fabricated from biodegradable materials, faster biodegradation of seam 22 can be achieved by one or more of the following: i) fabricating the seam from a faster biodegrading material, ii) pre-stressing the seam, or iii) perforating the seam. The concept of using biodegradable seams 22 to produce controlled degradation of a swallowable device in the GI tract can also be applied to other swallow able devices such as swallowable cameras (or other swallowable imaging device) to facilitate passage through the GI tract and reduce the likelihood of such a device becoming stuck in the GI tract. Accordingly, embodiments of biodegradable seam 22 can be adapted for swallowable imaging and other swallowable devices.

In still other embodiments, seam 22 can be constructed of materials and/or have a structure which is readily degraded by absorption of ultrasound energy, e.g. high frequency ultrasound—(HIFU), allowing the capsule to be degraded into smaller pieces using externally or endoscopically (or other minimally invasive method) administered ultrasound.

Another aspect of the invention provides methods for the delivery of drugs and other therapeutic agents (in the form of medication 100) into the walls of the GI tract using one or more embodiments of swallowable drug delivery device 10. An exemplary embodiment of such a method will now be described. The described embodiment of drug delivery occurs in the small intestine SI. However, it should be appreciated that this is exemplary and that embodiments of the invention can be used for delivering drug in a number of locations in the GI tract including the stomach and the large intestine. For ease of discussion, the swallowable drug delivery device 10 will sometimes be referred to herein as a capsule. As described above, in various embodiments device 10 may be packaged as a kit 14 within sealed packaging 12 that includes device 10 and a set of instructions for use 15. If the patient is using a handheld device 13, the patient may be instructed to enter data into device 13 either manually or via a bar code 18 (or other identifying indicia 18) located on the instructions 15 or packaging 12. If a bar code is used, the patient would scan the bar code using a bar code reader 19 on device 13. After opening packaging 12, reading the instructions 15 and entering any required data, the patient swallows an embodiment of the swallowable drug delivery device 10. Depending upon the drug, the patient may take the device 10 in conjunction with a meal (before, during or after) or a physiological measurement such as a blood glucose measurement. Capsule 20 is sized to pass through the GI tract and travels through the patient's stomach S and into the small intestine SI through peristaltic action as is embodied in device 10 shown in the embodiment of FIG. 1E. Once the capsule 10 is in the small intestine, coatings 20c' and 20c" are degraded by the basic pH in the small intestine (or other chemical or physical condition unique to the small intestine) causing expansion of balloon 30, 60 and 72 or deliver medication 100 into the wall of the small intestine SI according to one or more embodiments of the invention.

After medication delivery, device 10 then passes through the intestinal tract including the large intestine LI and is ultimately excreted. For embodiments having a tearable capsule, the capsule may immediately be broken into smaller pieces by inflation of balloon 30. For embodiments of the capsule 20 having biodegradable seams 22 or other biodegradable portions, the capsule is degraded in the intestinal tract into smaller pieces, to facilitate passage through and excretion from the intestinal tract. In particular embodiments having biodegradable tissue penetrating needles/members 40, should the needle get stuck in the intestinal wall, the needle biodegrades releasing the capsule 20 from the wall.

For embodiments of device 10 including a sensor 97, expansion of balloon 30 or other expandable member 30 can be effectuated by the senor sending a signal to a controllable embodiment of isolation valve 50 and/or a processor 29/controller 29c coupled to the isolation valve 50. For embodiments of device 10 including external actuation capability, the user may externally expand balloon 30 (as well as balloons 52 and 60) at a selected time period after swallowing the capsule. The time period can be correlated to a typical transit time (e.g., 30 minutes) or range of transit times (e.g., 10 minutes to 2 hrs.) for food moving through the user's GI tract to a particular location in the tract such as the small intestine.

One or more embodiments of the above methods can be used for the delivery of preparations 100 containing therapeutically effective amounts of a variety of drugs and other therapeutic agents 101 to treat a variety of diseases and conditions. These include a number of large molecule peptides and proteins which would otherwise require injection due to chemical breakdown in the stomach, e.g., growth hormone, parathyroid hormone, insulin, interferons and other like compounds. Suitable drugs and other therapeutic agents which can be delivered by embodiments of the invention to include various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents (e.g., furosemide), antimigraine medication (sumatriptan), immune suppression agents (e.g., cyclosporine) and anti-parasitic agents such as various anti-malarial agents. The dosage of the particular drug can be titrated for the patient's weight, age or other parameter. Also the drug 101 to achieve a desired or therapeutic effect (e.g., insulin for blood glucose regulation, furosemide for anti-seizure) can be less than the amount required should the drug have been delivered by conventional oral delivery (e.g., a swallowable pill that is digested in the stomach and absorbed through the wall of the small intestine). This is due to the fact that there is no degradation of the drug by acid and other digestive fluids in the stomach and the fact that all, as opposed to only a portion of the drug is delivered into the wall of the small intestine (or other lumen in the gastro-intestinal tract, e.g., large intestine, stomach, etc.). Depending upon the drug 101, the dose 102 delivered in preparation 100 can be in the range from 100 to 5% of a dose delivered by conventional oral delivery means to achieve a desired therapeutic effect (e.g., blood glucose regulation, seizure regulation, etc.) with even lower amounts contemplated. The particular dose reduction can be titrated based upon the particular drug, the condition to be treated, and the patient's weight, age and condition. For some drugs (with known levels of degradation in the intestinal tract) a standard dose reduction can be employed (e.g., 10 to 20%). Larger amounts of dose reduction can be used for drugs which are more prone to degradation and poor absorption. In this way, the potential toxicity and other side effects (e.g., gastric cramping, irritable bowel, hemorrhage, etc.) of a particular drug or drugs delivered by device 10 can be reduced because the ingested dose is lowered. This in turn, improves patient compliance because the patient has reduction both in the severity and incidence of side effects. Additional benefits of embodiments employing dose reduction of drug 101 include a reduced likelihood for the patient to develop a tolerance to the drug (requiring higher doses) and, in the case of antibiotics, for the patient to develop resistant strains of bacteria. Also, other levels of dose reduction can be achieved for patients undergoing gastric bypass operations and other procedures in which sections of the small intestine have been removed or its working (e.g., digestive) length effectively shortened.

In addition to delivery of a single drug, embodiments of swallowable drug delivery device 10 and methods of their use can be used to deliver a plurality of drugs for the treatment of multiple conditions or for the treatment of a particular condition (e.g., protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream, at about the same time. Due to difference in chemical makeup, molecular weight, etc., drugs can be absorbed through the intestinal wall at different rates, resulting in different pharmacokinetic distribution curves. Embodiments of the invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations 100 including drugs and therapeutic agents 101 to provide treatment for a number of medical conditions and diseases. The medical conditions and diseases which can be treated with embodiments of the invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia's (both atrial and ventricular), coronary ischemia anemia or other like condition. Still other conditions and diseases are also contemplated.

In many embodiments, the treatment of the particular disease or condition can be performed without the need for injecting the drug or other therapeutic agent (or other non-oral form of delivery such as suppositories) but instead, relying solely on the therapeutic agent(s) that is delivered into the wall of the small intestine or other portion of the GI tract. For example, diabetes or another glucose regulation disorder can be treated (e.g., by controlling blood glucose levels) solely through the use of insulin that is delivered into the wall of the small intestine without the need for the patient to ever inject insulin. Similarly, the patient need not take conventional oral forms of a drug or other therapeutic agent, but again rely solely on delivery into the wall of the small intestine using embodiments of the swallowable capsule. In other embodiments, the therapeutic agent(s) delivered into the wall of the small intestine can be delivered in conjunction with an injected dose of the agent(s). For example, the patient may take a daily dose of insulin or compound for blood glucose regulation using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods can be used to determine the appropriate dosages). Also, for embodiments using therapeutic agents that can be delivered by conventional oral means, the dose delivered using embodiments of the swallow able capsule can be titrated below the dosage normally given for oral delivery of the agent since there is little or no degradation of the agent within the stomach or other portion of the intestinal tract (herein again standard dose response curve and other pharmacokinetic methods can be applied).

Various groups of embodiments of preparation 100 containing one or more drugs or other therapeutic agents 101 for the treatment of various diseases and conditions will now be described with references to dosages. It should be appreciated that these embodiments, including the particular therapeutic agents and the respective dosages are exemplary and the preparation 100 can comprise a number of other therapeutic agents described herein (as well as those known in the art) that are configured for delivery into a luminal wall in the intestinal tract (e.g., the small intestinal wall) using various embodiments of device 10. The dosages can be larger or smaller than those described and can be adjusted using one or more methods described herein or known in the art. In one group of embodiments, therapeutic agent preparation 100 can comprise a therapeutically effective dose of insulin for the treatment of diabetes and other glucose regulation disorders. The insulin can be human or synthetically derived as is known in the art. In one embodiment, preparation 100 can contain a therapeutically effective amount of insulin in the range of about 1-10 units (one unit being the biological equivalent of about 45.5 μg of pure crystalline insulin), with particular ranges of 2-4, 3-9, 4-9, 5-8 or 6-7. The amount of insulin in the preparation can be titrated based upon one or more of the following factors (herein, then "glucose control titration factors"): i) the patient's condition (e.g., type I vs. type II diabetes; ii) the patient's previous overall level of glycemic control; iii) the patient's weight; iv) the patient's age; v) the frequency of dosage (e.g., once vs. multiple times a day); vi) time of day (e.g., morning vs. evening); vii) particular meal (breakfast vs. dinner); viii) content/glycemic index of a particular meal (e.g., meals having a high fat/lipid and sugar content (which tend to cause a rapid rise in blood sugar and thus have a higher glycemic index) vs. low fat and sugar content that do not (and thus have a lower glycemic index)); and ix) content of the patient's overall diet (e.g., amount of sugars and other carbohydrates, lipids and protein consumed daily).

In another group of embodiments, therapeutic agent preparation 100 can comprise a therapeutically effective dose of one or more incretins for the treatment of diabetes and other glucose regulation disorders. Such incretins can include glucagon-like peptides I (GLP-1) and their analogues, and Gastric inhibitory peptide (GIP). Suitable GLP-1 analogues include exenatide, liraglutide, albiglutide and taspoglutide as well as their analogues, derivatives and other functional equivalents. In one embodiment preparation 100 can contain a therapeutically effective amount of exenatide in the range of about 1-10 μg, with particular ranges of 2-4, 4-6, 4-8 and 8-10 μg respectively. In another embodiment, preparation 100 can contain a therapeutically effective amount of liraglutide in the range of about 1-2 mg (milligrams), with particular ranges of 1.0 to 1.4, 1.2 to 1.6 and 1.2 to 1.8 mg respectively. One or more of the glucose control titration factors can be applied to titrate the dose ranges for exenatide, liraglutide or other GLP-1 analogue or incretin.

In yet another group of embodiments, therapeutic agent preparation 100 can comprise a combination of therapeutic agents for the treatment of diabetes and other glucose regulation disorders. Embodiments of such a combination can include therapeutically effective doses of incretin and biguanide compounds. The incretin can comprise one or more GLP-1 analogues described herein, such as exenatide and the biguanide can comprise metformin (e.g., that available under the Trademark of GLUCOPHAGE manufactured by Merck Sante S.A.S.) and its analogues, derivatives and other functional equivalents. In one embodiment, preparation 100 can comprise a combination of a therapeutically effective amount of exenatide in the range of about 1-10 μg and a therapeutically effective amount of metformin in a range of about 1 to 3 grams. Smaller and larger ranges are also contemplated with one or more of the glucose control titration factors used to titrate the respective dose of exenatide (or other incretin) and metformin or other biguanide. Additionally, the dosages of the exenatide or other incretin and metformin or other biguanide can be matched to improve the level of glucose control for the patient (e.g., maintenance of blood glucose within normal physiological levels and/or a reduction in the incidence and severity of instances of hyperglycemia and/or hypoglycemia) for extended periods of time ranging from hours (e.g., 12) to a day to multiple days, with still longer periods contemplated. Matching of dosages can also be achieved by use of the glucose control regulation factors as well as monitoring of the patient's blood glucose levels for extended periods using glycosylated hemoglobin (known as hemoglobin Ale, HbAlc, AIC, or Hblc) and other analytes and measurements correlative to long term average blood glucose levels.

In still yet another group of embodiments, therapeutic agent preparation 100 can comprise a therapeutically effective dose of growth hormone for the treatment of one or more growth disorders, as well as wound healing. In one embodiment, preparation 100 can contain a therapeutically effective amount of growth hormone in the range of about 0.1-4 mg, with particular ranges of 0.1-1, 1-4, 1-2 and 2-4, with still larger ranges contemplated. The particular dose can be titrated based on one or more of the following: i) the particular condition to be treated and its severity (e.g., stunted growth, vs. wound healing); ii) the patient's weight; iii) the patient's age; and iv) the frequency of dosage (e.g., daily vs. twice daily).

In still yet another group of embodiments, therapeutic agent preparation 100 can comprise a therapeutically effective dose of parathyroid hormone for the treatment osteoporosis or a thyroid disorder. In one embodiment, preparation 100 can contain a therapeutically effective amount of parathyroid hormone in the range of about 1-40 µg, with particular ranges of 10-20, 20-30, 30-40 and 10-40 µg, with still larger ranges contemplated. The particular dose can be titrated based on one or more of the following: i) the particular condition to be treated and its severity (e.g., the degree of osteoporosis as determined by bone density measurements); ii) the patient's weight; iii) the patient's age; and iv) the frequency of dosage (e.g., daily vs. twice daily).

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method of delivering a therapeutic agent preparation into a gastrointestinal (GI) wall of a patient, the method comprising:
   administering, by swallowing by a patient, a swallowable device sized to pass through a GI tract, wherein the device comprises a capsule, the therapeutic agent preparation disposed within the capsule, an aligner, and a delivery mechanism for advancing the therapeutic agent preparation from the capsule into the GI wall, wherein the delivery mechanism comprises an expandable member and a piston-cylinder assembly operably coupled to the expandable member, wherein the piston-cylinder assembly comprises a piston slidably disposed in a cylinder, and wherein the piston-cylinder assembly is at least partially disposed in the expandable member;
   wherein, upon swallowing of the device, the piston-cylinder assembly is oriented relative to the GI wall via the aligner such that a long axis of the piston-cylinder assembly is perpendicular to a surface of the GI wall; and
   wherein the expandable member causes the piston to advance through the cylinder to deliver the therapeutic agent preparation into the GI wall.

2. The method of claim 1, wherein the therapeutic agent preparation is formed as a tissue penetrating member disposed in the capsule and configured to be advanced into the GI wall by the piston-cylinder assembly.

3. The method of claim 1, wherein the therapeutic agent preparation is disposed in a cavity of a tissue penetrating member, and wherein the tissue penetrating member is disposed in the capsule and is configured to be advanced into the GI wall by the piston-cylinder assembly.

4. The method of claim 1, wherein the expandable member comprises a first compartment and a second compartment separated by a releasable valve which releases upon exposure to fluid in the GI tract.

5. The method of claim 4, wherein the piston-cylinder assembly is oriented relative to the GI wall in response to the releasable valve releasing.

6. The method of claim 4, wherein the expandable member further comprises a first reactant contained in one of the first or second compartments and a second reactant contained in the other of the first or second compartments, wherein, when the releasable valve releases, the first and second reactants mix to produce a gas.

7. The method of claim 6, wherein the first and second reactant comprise an acid and a base, respectively.

8. The method of claim 6, wherein the first reactant comprises potassium bicarbonate and the second reactant comprises citric acid.

9. The method of claim 1, wherein the piston-cylinder assembly comprises a pressure sensitive release that prevents the piston from advancing through the cylinder until the expandable member generates a threshold force.

10. The method of claim 9, wherein the pressure sensitive release comprises a tab, a latch, or an O-ring.

11. The method of claim 1, wherein the capsule comprises a capsule wall, wherein at least a portion of the capsule wall degrades upon exposure to a selected pH in an intestine while protecting the capsule wall from degradation in a stomach of the patient.

12. The method of claim 1, wherein delivering the therapeutic agent preparation into the GI wall comprises delivering the therapeutic agent preparation past a mucosal or submucosal layer of the GI wall.

13. The method of claim 1, wherein the GI wall is a wall of an intestine.

14. The method of claim 1, wherein the aligner comprises a joint configured to exert a force on the piston-cylinder assembly to bias the piston-cylinder assembly into a vertical orientation.

15. The method of claim 1, wherein the aligner comprises an aligner balloon.

16. The method of claim 1, wherein the therapeutic agent preparation comprises a growth hormone, parathyroid hormone, an antibody, a chemotherapeutic agent, insulin, one or more glucagon-like peptides, an immune suppression agent, a vaccine, or an anti-parasitic agent.

17. A swallowable device for delivering a therapeutic agent preparation into a gastrointestinal (GI) wall of a patient, the device comprising:
   a capsule sized to pass through a GI tract;
   the therapeutic agent preparation disposed within the capsule;
   an aligner; and
   a delivery mechanism for advancing the therapeutic agent preparation from the capsule into the GI wall, wherein the delivery mechanism comprises:
      an expandable member; and
      a piston-cylinder assembly operably coupled to the expandable member, wherein the piston-cylinder assembly comprises a piston slidably disposed in a cylinder, and wherein the piston-cylinder assembly is at least partially disposed in the expandable member;

wherein, upon swallowing the device, the piston-cylinder assembly is aligned relative to the GI wall via the aligner such that a long axis of the piston-cylinder assembly is oriented perpendicular to a surface of the GI wall; and wherein the expandable member causes the piston to advance through the cylinder to deliver the therapeutic agent preparation into the GI wall.

18. The swallowable device of claim 17, wherein the aligner comprises a joint configured to exert a force on the piston-cylinder assembly to bias it into a vertical orientation or an aligner balloon.

19. A swallowable device for delivering a therapeutic agent preparation into a gastrointestinal (GI) wall of a patient, the device comprising:
   a capsule sized to pass through a GI tract;
   the therapeutic agent preparation disposed within the capsule; and
   a delivery mechanism for advancing the therapeutic agent preparation from the capsule into the GI wall, wherein the delivery mechanism comprises:
      an expandable member comprising an aligner; and
      a piston-cylinder assembly operably coupled to the expandable member, wherein the piston-cylinder assembly comprises a piston slidably disposed in a cylinder, and wherein the piston-cylinder assembly is at least partially disposed in the expandable member;
   wherein, upon swallowing the device, the piston-cylinder assembly is aligned relative to the GI wall via the aligner such that a long axis of the piston-cylinder assembly is oriented perpendicular to a surface of the GI wall; and
   wherein the expandable member causes the piston to advance through the cylinder to deliver the therapeutic agent preparation into the GI wall.

20. The swallowable device of claim 19, wherein the aligner comprises a pre-stressed portion of the expandable member.

* * * * *